United States Patent
Watanabe et al.

(10) Patent No.: US 9,614,165 B2
(45) Date of Patent: Apr. 4, 2017

(54) PHOTOELECTRIC CONVERSION ELEMENT, DYE-SENSITIZED SOLAR CELL, METAL COMPLEX DYE, DYE SOLUTION, DYE-ADSORBED ELECTRODE AND METHOD OF PRODUCING DYE-SENSITIZED SOLAR CELL

(71) Applicant: FUJIFILM Corporation, Minato-ku, Tokyo (JP)

(72) Inventors: Kousuke Watanabe, Kanagawa (JP); Kouitsu Sasaki, Kanagawa (JP); Katsumi Kobayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 113 days.

(21) Appl. No.: 14/740,827

(22) Filed: Jun. 16, 2015

(65) Prior Publication Data

US 2015/0280145 A1     Oct. 1, 2015

Related U.S. Application Data

(63) Continuation of application No. PCT/JP2013/083660, filed on Dec. 16, 2013.

(30) Foreign Application Priority Data

Dec. 17, 2012 (JP) .................. 2012-275139
Dec. 13, 2013 (JP) .................. 2013-258323

(51) Int. Cl.
*H01L 51/00* (2006.01)
*C09B 62/343* (2006.01)
(Continued)

(52) U.S. Cl.
CPC ........ *H01L 51/0086* (2013.01); *C07D 213/55* (2013.01); *C07D 213/79* (2013.01);
(Continued)

(58) Field of Classification Search
None
See application file for complete search history.

(56) References Cited

U.S. PATENT DOCUMENTS

2012/0073660 A1    3/2012   Chi et al.

FOREIGN PATENT DOCUMENTS

| JP | 60-106859 A | 6/1985 |
| JP | 2000-190641 A | 7/2000 |

(Continued)

OTHER PUBLICATIONS

International Search Report for PCT/JP2013/083660 dated Feb. 25, 2014 [PCT/ISA/210].
(Continued)

*Primary Examiner* — Catherine S Branch
(74) *Attorney, Agent, or Firm* — Sughrue Mion, PLLC

(57) ABSTRACT

A photoelectric conversion element including a photoconductor layer, wherein the photoconductor layer contains semiconductor fine particles carrying a metal complex dye of Formula (I); a metal complex dye, a dye solution, a dye-adsorbed electrode, a dye-sensitized solar cell, and a method for producing the solar cell:

$$M(LD)(LA) \cdot (CI) \quad \text{Formula (I)}$$

wherein M represents a metal ion; LD represents a tridentate ligand of formulas (DL-1) to (DL-4); LA represents a specific tridentate ligand; and CI represents a counter ion:

Formula (DL-1)

(Continued)

-continued

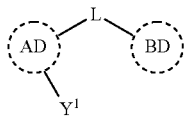

Formula (DL-2)

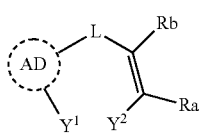

Formula (DL-3)

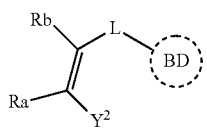

Formula (DL-4)

$Y^1$ and $Y^2$ represent an oxygen, sulfur, nitrogen, or phosphorus atom; AD and BD represent a hydrocarbon or hetero ring; L represents a linking group of formulas (L-1) to (L-4); and Ra and Rb represent a substituent,

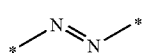
Formula (L-1)

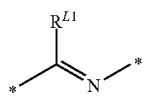

Formula (L-2)

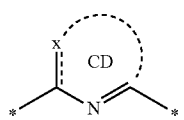

Formula (L-3)

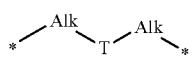

Formula (L-4)

X represents a nitrogen or carbon atom; CD represents hetero ring; T represents —O—, —S—, —NR$^{L2}$— or —PR$^{L3}$; R$^{L1}$ to R$^{L3}$ represent a hydrogen atom or a substituent; and Alk represents an alkylene group.

23 Claims, 6 Drawing Sheets

(51) Int. Cl.
| | |
|---|---|
| H01G 9/20 | (2006.01) |
| C09B 62/355 | (2006.01) |
| C09B 62/36 | (2006.01) |
| C09B 62/20 | (2006.01) |
| C07D 401/14 | (2006.01) |
| C07D 213/79 | (2006.01) |
| C07D 231/38 | (2006.01) |
| C07D 401/04 | (2006.01) |
| C07D 409/04 | (2006.01) |
| C07D 409/14 | (2006.01) |
| C07D 417/14 | (2006.01) |
| C07D 213/55 | (2006.01) |
| C09B 57/10 | (2006.01) |
| C09B 23/01 | (2006.01) |
| C09B 23/04 | (2006.01) |
| C09B 23/10 | (2006.01) |
| C09B 29/01 | (2006.01) |
| C09B 29/036 | (2006.01) |
| C09B 29/12 | (2006.01) |
| C09B 57/00 | (2006.01) |
| C07F 15/00 | (2006.01) |
| H01M 14/00 | (2006.01) |
| C09B 45/14 | (2006.01) |
| C09B 45/22 | (2006.01) |
| C09B 55/00 | (2006.01) |

(52) U.S. Cl.
CPC ......... *C07D 231/38* (2013.01); *C07D 401/04* (2013.01); *C07D 401/14* (2013.01); *C07D 409/04* (2013.01); *C07D 409/14* (2013.01); *C07D 417/14* (2013.01); *C07F 15/0053* (2013.01); *C09B 23/005* (2013.01); *C09B 23/0025* (2013.01); *C09B 23/0058* (2013.01); *C09B 23/0066* (2013.01); *C09B 23/04* (2013.01); *C09B 23/105* (2013.01); *C09B 29/0003* (2013.01); *C09B 29/0037* (2013.01); *C09B 29/12* (2013.01); *C09B 45/14* (2013.01); *C09B 45/22* (2013.01); *C09B 55/00* (2013.01); *C09B 57/007* (2013.01); *C09B 57/10* (2013.01); *C09B 62/205* (2013.01); *C09B 62/3435* (2013.01); *C09B 62/355* (2013.01); *C09B 62/365* (2013.01); *H01G 9/2031* (2013.01); *H01G 9/2059* (2013.01); *H01M 14/005* (2013.01); *Y02E 10/542* (2013.01); *Y02E 10/549* (2013.01); *Y02P 70/521* (2015.11)

(56) References Cited

FOREIGN PATENT DOCUMENTS

| JP | 2006-306070 A | 11/2006 |
| JP | 2009-067976 A | 4/2009 |
| JP | 2012-036237 A | 2/2012 |
| WO | 91/16719 A1 | 10/1991 |
| WO | 2011/032269 A1 | 3/2011 |

OTHER PUBLICATIONS

Chun-Cheng Chou et al., "Dye-Sensitized Solar Cells: Ruthenium(II) Sensitizers with Heteroleptic Tridentate Chelates for Dye-Sensitized Solar Cells", Angew. Chem. Int. Ed, vol. 50, pp. 2054-2058, (2011). DOI: 10.1002/anie.201006629.

Communication dated Nov. 13, 2015, from the European Patent Office in counterpart European Application No. 13865285.4.

PHOTOELECTRIC CONVERSION ELEMENT, DYE-SENSITIZED SOLAR CELL, METAL COMPLEX DYE, DYE SOLUTION, DYE-ADSORBED ELECTRODE AND METHOD OF PRODUCING DYE-SENSITIZED SOLAR CELL

CROSS-REFERENCE TO RELATED APPLICATIONS

This application is a Continuation of PCT International Application No. PCT/JP2013/083660 filed on Dec. 16, 2013, which claims priority under 35 U.S.C. §119 (a) to Japanese Patent Application No. 2012-275139 filed on Dec. 17, 2012 and Japanese Patent Application No. 2013-258323 filed on Dec. 13, 2013. Each of the above applications is hereby expressly incorporated by reference, in its entirety, into the present application.

TECHNICAL FIELD

The present invention relates to a photoelectric conversion element, a dye-sensitized solar cell, a metal complex dye, a dye solution, a dye-adsorbed electrode and a method of producing the dye-sensitized solar cell.

BACKGROUND ART

Photoelectric conversion elements are used in various photosensors, copying machines, solar cells, and the like. These photoelectric conversion elements have adopted various systems to be put into use, such as elements utilizing metals, elements utilizing semiconductors, elements utilizing organic pigments or dyes, or combinations of these elements. In particular, solar cells that make use of non-exhaustive solar energy do not necessitate fuels, and full-fledged practicalization of solar cells as an inexhaustible clean energy is being highly expected. Among these, research and development of silicon-based solar cells have long been in progress. Many countries also support policy-wise considerations, and thus dissemination of silicon-based solar cells is still in progress. However, silicon is an inorganic material, and has its own limitations in terms of improving throughput and cost, and the like.

Under such circumstances, research is being vigorously carried out on dye-sensitized solar cells. Especially, to have built momentum toward such research is research results by Graetzel et al. of École Polytechnique Fédérale de Lausanne in Switzerland (see Patent Literature 1). They employed a structure in which a dye formed from a ruthenium complex was fixed at the surface of a porous titanium oxide thin film, and realized a conversion efficiency that was comparable to that of amorphous silicon. Thus, the dye-sensitized solar cells that can be produced even without using an expensive vacuum apparatus instantly attracted the attention of researchers all over the world.

Hitherto, as metal complex dyes to be used in photoelectric conversion elements, dyes generally called as N3, N719, Z907, and J2 have been developed.

Meanwhile, recently, a ruthenium metal complex dye having a bidentate or tridentate ligand having a specific aromatic-ring anion at the coordination atom of a ligand, is being suggested (see Patent Literature 2 or 3). In addition, a ruthenium metal complex dye having a specific ligand combination using (pyridylazo)resorcinol, and the like, as a bidentate ligand, is also known (see Patent Literature 1). However, the improvements of durability and photoelectric conversion efficiency in a long wavelength range of 900 nm or more are not always satisfactory.

CITATION LIST

Patent Literatures

Patent Literature 1: WO 91/16719
Patent Literature 2: US 2012/0073660 A1
Patent Literature 3: JP-A-2009-67976 ("JP-A" means unexamined published Japanese patent application)

SUMMARY OF INVENTION

Technical Problem

In view of the above situation, the present invention aims to provide a photoelectric conversion element and a dye-sensitized solar cell which are excellent in durability as well as improved with the photoelectric conversion efficiency by increasing the optical absorption in a long wavelength range in the absorption properties of the metal complex dye so as to improve the spectral sensitivity characteristics in the long wavelength range. In addition, the present invention also aims to provide a metal complex dye, a dye solution and a dye-adsorbed electrode, and a method for producing dye-sensitized solar cell.

Solution to Problem

The present inventors have conducted various investigations to improve the spectral sensitivity characteristics, namely the quantum yield (IPCE), in a long wavelength range, especially sensitivity characteristics in 900 nm to 1000 nm, since conventional metal complex dyes do not always have sufficient spectral sensitivity characteristics in a long wavelength range.

As a result, the present inventors found that, in a ligand that is used along with a ligand having a function capable of being adsorbed onto the surfaces of semiconductor fine-particles, a tridentate ligand having unshared electron pair at a coordination atom has excellent spectral sensitivity characteristic and durability. Therefore, the present inventors completed the present invention.

That is, the tasks of the present invention can be achieved by the following means.

(1) A photoelectric conversion element, having an electrically conductive support, a photoconductor layer containing an electrolyte, a charge transfer layer containing an electrolyte, and a counter electrode, wherein the photoconductor layer contains semiconductor fine particles carrying a metal complex dye represented by the following Formula (I):

M(LD)(LA)·(CI)        Formula (I)

wherein, in the formula, M represents a metal ion;
LD represents a tridentate ligand represented by any one of the following formulas (DL-1) to (DL-4);
LA represents a tridentate ligand represented by the following formula (AL); and
CI represents a counter ion necessary to neutralize an electric charge:

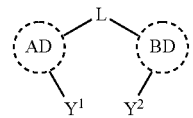

Formula (DL-1)

Formula (DL-2)

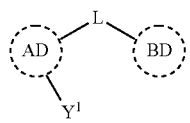

Formula (DL-3)

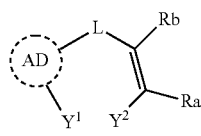

Formula (DL-4)

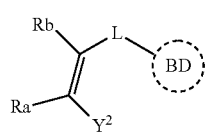

Formula (AL)

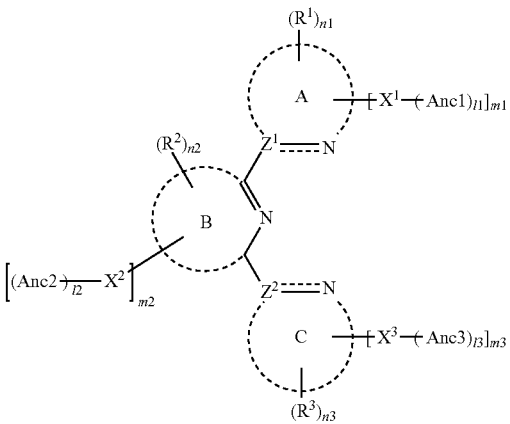

wherein, in the formulas, $Y^1$ and $Y^2$ each independently represent an oxygen atom, a sulfur atom, a substituted or unsubstituted nitrogen atom, or a substituted or unsubstituted phosphorus atom, each of which coordinates with the metal ion M; the ring AD and the ring BD each independently represents a hydrocarbon ring or a hetero ring; L represents a linking group represented by any one of the following formulas (L-1) to (L-4); and Ra and Rb each independently represent a substituent, Formula (L-1)

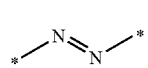

Formula (L-2)

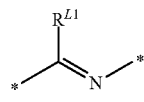

Formula (L-3)

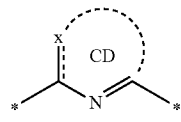

Formula (L-4)

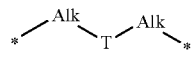

wherein, in the formulas, $R^{L1}$ represents a hydrogen atom or a substituent; X represents a nitrogen atom or a carbon atom; the ring CD represents a nitrogen-containing hetero ring containing X; the bond between X and the carbon atom bonded with X and N may be a single bond or a double bond; the ring CD may have a substituent; T represents —O—, —S—, —$NR^{L2}$ or —$PR^{L3}$—; $R^{L2}$ and $R^{L3}$ each independently represent a hydrogen atom or a substituent; and Alk represents an alkylene group, which may have a substituent, wherein, in the formulas, the ring A, the ring B, and the ring C each independently represent a nitrogen-containing aromatic hetero ring; herein, the bond between $Z^1$ and N and the bond between $Z^2$ and N may be a single bond or a double bond; $Z^1$ and $Z^2$ each independently represent a carbon atom or a nitrogen atom;

Anc1 to Anc3 each independently represent —$CO_2H$, —$SO_3H$, —$PO_3H_2$, —OH, —SH or a salt thereof; $X^1$, $X^2$ and $X^3$ each independently represent a single bond or a linking group; l1 to l3 each independently represent an integer of 1 to 5; m1 and m3 each independently represent an integer of 0 to 4; m2 represent an integer of 0 to 3; a total of m1 to m3 is 1 or more;

$R^1$ to $R^3$ each independently represent a substituent other than Anc1 to Anc3; n1 and n3 each independently represent an integer of 0 to 2; and n2 represents 0 or 1.

(2) The photoelectric conversion element described in item (1), wherein M represents $Fe^{2+}$, $Ru^{2+}$ or $Os^{2+}$.

(3) The photoelectric conversion element described in item (1) or (2), wherein LD represents a tridentate ligand represented by formula (DL-1) or formula (DL-2); and L in formula (DL-1) or formula (DL-2) is a linking group represented by formula (L-1) or formula (L-3).

(4) The photoelectric conversion element described in any one of items (1) to (3), wherein the ring CD in formula (L-3) is a pyridine ring, a pyrimidine ring, or a triazine ring.

(5) The photoelectric conversion element described in any one of items (1) to (4), wherein the ring AD and the ring BD in formulas (DL-1) to (DL-4) is a benzene ring, a pyrazole ring, or a triazole ring.

(6) The photoelectric conversion element described in item (1) or (2), wherein L represents a linking group represented by formula (L-1) or a linking group represented by formula (L-3); and when L is formula (L-1), in formula (DL-1), the ring AD and the ring BD each independently represent a benzene ring, a pyrazole ring, or an imidazole ring; $Y^1$ and $Y^2$ each independently represent —$O^-$, —$S^-$, or —$NR^-$ (R represents a hydrogen atom or a substituent); in formula (DL-2), the ring AD represents a benzene ring, and the ring BD represents a benzene ring, a pyrazole ring, an imidazole ring, or a triazole ring; $Y^1$ represents —$O^-$, —$S^-$, or —$NR^-$ (R represents a hydrogen atom or a substituent);

in formula (DL-3), the ring AD represents a benzene ring; and $Y^1$ and $Y^2$ each independently represent —O$^-$, —S$^-$, or —NR$^-$ (R represents a hydrogen atom or a substituent); and when L is formula (L-3), in formula (DL-1), the ring AD and the ring BD each represent a benzene ring; $Y^1$ and $Y^2$ each independently represent —O$^-$, —S$^-$, or —NR$^-$ (R represents a hydrogen atom or a substituent);

in formula (DL-2), the ring AD represents a benzene ring, and the ring BD represents a benzene ring, a pyrazole ring, an imidazole ring, or a triazole ring; and Y1 represents —O$^-$, —S$^-$, or —NR$^-$ (R represents a hydrogen atom or a substituent).

(7) The photoelectric conversion element described in any one of items (1) to (6), wherein the ring A, the ring B and the ring C in the formula (AL) each represent a pyridine ring, a pyrimidine ring, or a thiazole ring.

(8) The photoelectric conversion element described in any one of items (1) to (7), wherein the formula (AL) is the following formula (AL-1) or formula (AL-2):

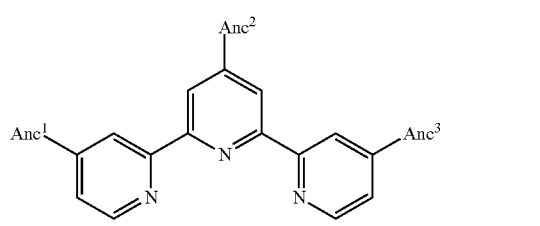

Formula (AL-1)

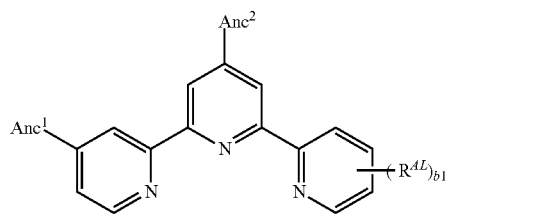

Formula (AL-2)

wherein, in the formulas, Anc$^1$ to Anc$^3$ each independently represent —CO$_2$H, —SO$_3$H, —PO$_3$H$_2$ or a salt thereof; R$^{AL}$ represents a substituent other than Anc$^1$ to Anc$^3$; and b1 represents an integer of 0 to 4.

(9) The photoelectric conversion element described in item (8), wherein the formula (AL) is the formula (AL-1).

(10) The photoelectric conversion element described in item (8), wherein the formula (AL) is the formula (AL-2).

(11) The photoelectric conversion element described in any one of items (1) to (7), wherein the formula (AL) is the following formula (AL-3) or formula (AL-4):

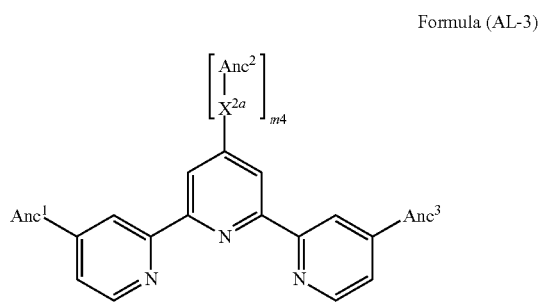

Formula (AL-3)

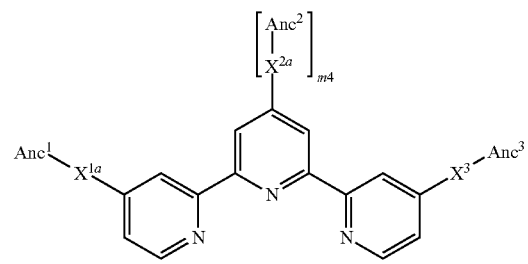

Formula (AL-4)

wherein, in the formulas, Anc$^1$ to Anc$^3$ each independently represent —CO$_2$H, —SO$_3$H, —PO$_3$H$_2$ or a salt thereof; X$^{2a}$ represents —O—, —S—, —NR'—, a divalent saturated aliphatic group, a divalent aromatic hydrocarbon ring group, a divalent non-aromatic hydrocarbon ring group, a divalent aromatic hetero ring group, a divalent non-aromatic hetero ring group, or a linking group formed by any combination of these; herein R' represents a hydrogen atom or a substituent; X$^{1a}$ represents a linking group; X$^3$ represents a single bond or a linking group; and m4 represents 0 or 1.

(12) The photoelectric conversion element described in any one of items (1) to (11), wherein a co-adsorbent having one or more acidic groups is carried on the semiconductor fine-particles.

(13) The photoelectric conversion element described in item (12), wherein the co-adsorbent is represented by the following formula (CA):

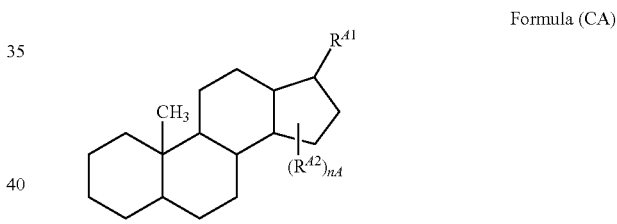

Formula (CA)

wherein, in the formula, R$^{A1}$ represents a substituent having an acidic group; R$^{A2}$ represents a substituent; and nA represents an integer of 0 or more.

(14) A dye-sensitized solar cell, containing the photoelectric conversion element described in any one of items (1) to (13).

(15) A metal complex dye, which is represented by the following formula (I):

M(LD)(LA)·(CI)　　　Formula (I)

wherein, in the formula, M represents a metal ion;

LD represents a tridentate ligand represented by any one of the following formulas (DL-1) to (DL-4);

LA represents a tridentate ligand represented by the following formula (AL); and CI represents a counter ion necessary to neutralize an electric charge:

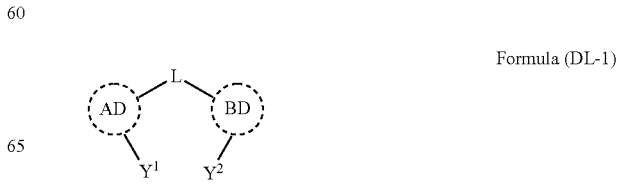

Formula (DL-1)

-continued

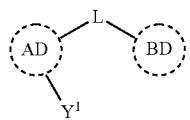
Formula (DL-2)

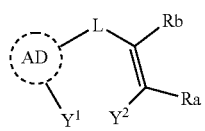
Formula (DL-3)

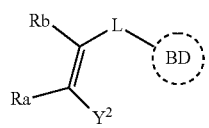
Formula (DL-4)

wherein, in the formulas, $Y^1$ and $Y^2$ each independently represent an oxygen atom, a sulfur atom, a substituted or unsubstituted nitrogen atom, or a substituted or unsubstituted phosphorus atom, each of which coordinates with the metal ion M; the ring AD and the ring BD each independently represents a hydrocarbon ring or a hetero ring; L represents a linking group represented by any one of the following formulas (L-1) to (L-4); and Ra and Rb each independently represent a substituent,

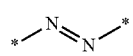
Formula (L-1)

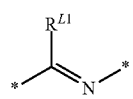
Formula (L-2)

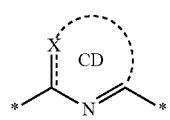
Formula (L-3)

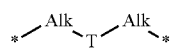
Formula (L-4)

wherein, in the formulas, $R^{1-1}$ represents a hydrogen atom or a substituent; X represents a nitrogen atom or a carbon atom; the ring CD represents a nitrogen-containing hetero ring containing X; the bond between X and the carbon atom bonded with X and N may be a single bond or a double bond; the ring CD may have a substituent; T represents —O—, —S—, —$NR^{L2}$— or —$PR^{L3}$—; $R^{L2}$ and $R^{L3}$ each independently represent a hydrogen atom or a substituent; and Alk represents an alkylene group, which may have a substituent,

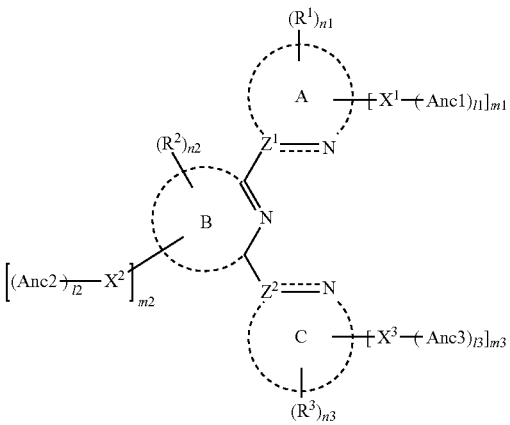
Formula (AL)

wherein, in the formula, the ring A, the ring B, and the ring C each independently represent a nitrogen-containing aromatic hetero ring; herein, the bond between $Z^1$ and N and the bond between $Z^2$ and N may be a single bond or a double bond; $Z^1$ and $Z^2$ each independently represent a carbon atom or a nitrogen atom;

Anc1 to Anc3 each independently represent —$CO_2H$, —$SO_3H$, —$PO_3H_2$, —OH, —SH or a salt thereof; $X^1$, $X^2$ and $X^3$ each independently represent a single bond or a linking group; l1 to l3 each independently represent an integer of 1 to 5; m1 and m3 each independently represent an integer of 0 to 4; m2 represent an integer of 0 to 3; a total of m1 to m3 is 1 or more;

$R^1$ to $R^3$ each independently represent a substituent other than Anc1 to Anc3; n1 and n3 each independently represent an integer of 0 to 2; and n2 represents 0 or 1.

(16) The metal complex dye described in item (15), wherein
L represents a linking group represented by formula (L-1) or a linking group represented by formula (L-3); and
when L is formula (L-1),
in formula (DL-1), the ring AD and the ring BD each independently represent a benzene ring, a pyrazole ring, or an imidazole ring; $Y^1$ and $Y^2$ each independently represent —$O^-$, —$S^-$, or —$NR^-$ (R represents a hydrogen atom or a substituent);
in formula (DL-2), the ring AD represents a benzene ring, and the ring BD represents a benzene ring, a pyrazole ring, an imidazole ring, or a triazole ring; $Y^1$ represents —$O^-$, —$S^-$, or —$NR^-$ (R represents a hydrogen atom or a substituent);
in formula (DL-3), the ring AD represents a benzene ring; and $Y^1$ and $Y^2$ each independently represent —$O^-$, —$S^-$, or —$NR^-$ (R represents a hydrogen atom or a substituent); and
when L is formula (L-3),
in formula (DL-1), the ring AD and the ring BD each represent a benzene ring; $Y^1$ and $Y^2$ each independently represent —$O^-$, —$S^-$, or —$NR^-$ (R represents a hydrogen atom or a substituent);
in formula (DL-2), the ring AD represents a benzene ring, and the ring BD represents a benzene ring, a pyrazole ring, an imidazole ring, or a triazole ring; and $Y^1$ represents —$O^-$, —$S^-$, or —$NR^-$ (R represents a hydrogen atom or a substituent).

(17) The metal complex dye described in item (15) or (16), wherein the formula (AL) is any one of the following formulas (AL-1) to (AL-4):

Formula (AL-1)

Formula (AL-2)

Formula (AL-3)

Formula (AL-4)

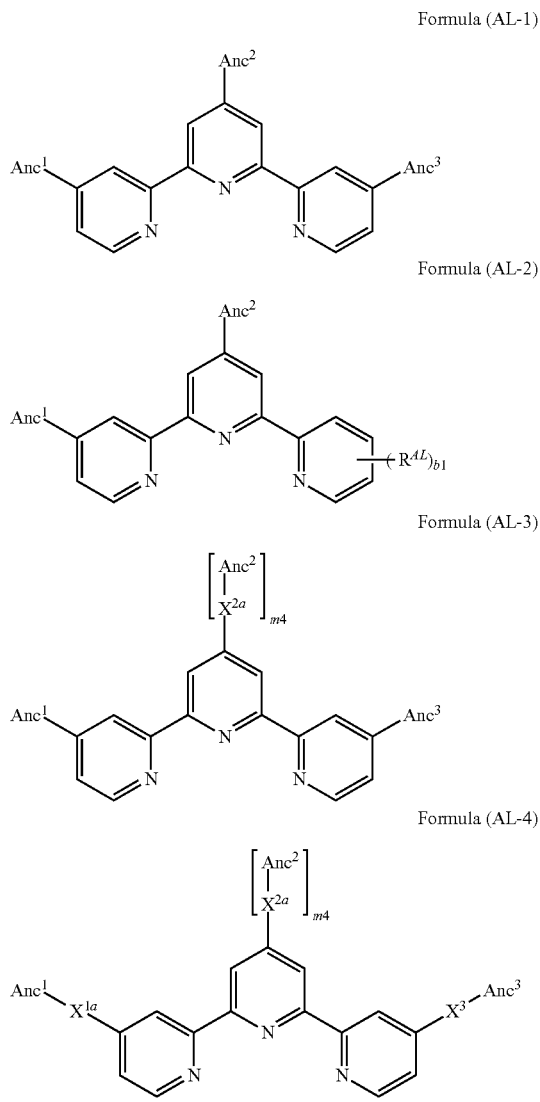

wherein, in the formulas, $Anc^1$ to $Anc^3$ each independently represent —$CO_2H$, —$SO_3H$, —$PO_3H_2$ or a salt thereof; $R^{AL}$ represents a substituent other than $Anc^1$ to Anc3; b1 represents an integer of 0 to 4; $X^{2a}$ represents —O—, —S—, —NR'—, a divalent saturated aliphatic group, a divalent aromatic hydrocarbon ring group, a divalent non-aromatic hydrocarbon ring group, a divalent aromatic hetero ring group, a divalent non-aromatic hetero ring group, or a linking group formed by any combination of these; herein R' represents a hydrogen atom or a substituent; $X^{1a}$ represents a linking group; $X^3$ represents a single bond or a linking group; and m4 represents 0 or 1.

(18) A dye solution, dissolved therein the metal complex dye described in any one of items (15) to (17).
(19) The dye solution described in item (18), wherein, in an organic solvent, the metal complex dye is contained in an amount of from 0.001 to 0.1% by mass, and water is limited to 0.1% by mass or less.
(20) The dye solution described in item (18) or (19), further containing a co-adsorbent.
(21) The dye solution described in item (20), wherein the co-adsorbent is represented by the following formula (CA):

Formula (CA)

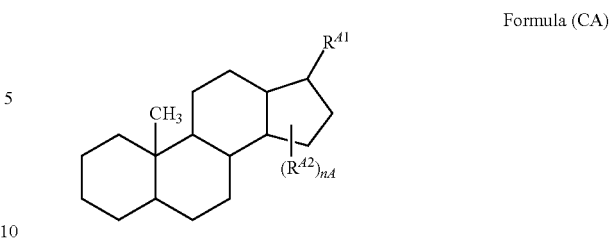

wherein, in the formula, $R^{A1}$ represents a substituent having an acidic group; $R^{A2}$ represents a substituent; and nA represents an integer of 0 or more.
(22) A dye-adsorbed electrode for a dye-sensitized solar cell, having a photoconductor layer which is formed by applying a composition obtained from the dye solution described in any one of items (18) to (21) on an electrically-conductive support provided with a semiconductor, and then, curing the composition after being applied.
(23) A method of producing a dye-sensitized solar cell, the method including assembling the dye-adsorbed electrode described in item (22) and materials to be an electrolyte and a counter electrode.

In the present specification, unless otherwise specified, with respect to the carbon-carbon double bond, in a case where the E configuration or the Z configuration exists in the molecule, it may be either one of the two configurations or a mixture thereof. When there are two or more substituents, linking groups, ligands or the like (hereinafter referred to as substituents or the like) represented by a specific symbol, or when two or more substituents or the like are defined at the same time or alternatively, each of the substituents or the like may be the same or different from one another, unless otherwise specified. This also applies to definition of the number of substituents or the like. Further, when a plurality of substituents or the like are close to one another (particularly adjacent to each other), they may be linked to one another to form a ring, unless otherwise specified. Further, a ring, for example, an aliphatic ring, an aromatic ring, or a heterocycle, may be ring-fused to form a fused ring.

In the present invention, each substituent may be further substituted with another substituent, unless otherwise specified.

Advantageous Effects of Invention

According to the present invention, among the absorption characteristics of the metal complex dye, an optical absorption of a long wavelength range is increased, and also, a spectral sensitivity characteristic in the long wavelength range is improved, thereby it is possible to provide a photoelectric conversion element and a dye-sensitized solar cell having excellent photoelectric conversion efficiency and durability, and a metal complex dye, a dye solution, and a dye-adsorbed electrode, which are used for the element and solar cell, and a method of producing the dye-sensitized solar cell.

Other and further features and advantages of the invention will appear more fully from the following description, appropriately referring to the accompanying drawings.

DESCRIPTION OF EMBODIMENTS

<<Photoelectric Conversion Element and Dye-Sensitized Solar Cell>>

Figure 1:
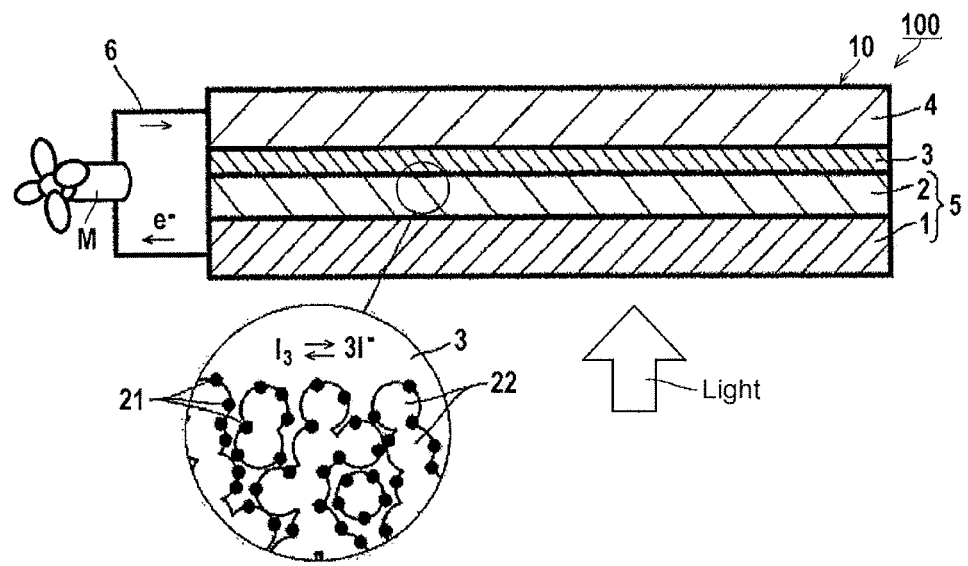
FIG. 1 is a cross-sectional view schematically showing one embodiment of the photoelectric conversion element of the present invention, including an enlarged view of the circled portion in the layer thereof.

In the photoelectric conversion element of the present invention, for example, as shown in FIG. 1, the photoelectric conversion element 10 is composed of: an electrically-conductive support 1; a photoconductor layer 2 containing semiconductor fine-particles which has been sensitized by a dye (metal complex dye) 21; a charge-transfer layer 3 which is a hole-transport layer, and a counter electrode 4. In the present invention, it is preferred that a co-adsorbent has been adsorbed, together with the dye (metal complex dye) 21, onto semiconductor fine-particles 22. The electrically conductive support 1 in which the photoconductor layer 2 has been provided functions as a working electrode in the photoelectric conversion element 10. In this embodiment, the photoelectric conversion element 10 is shown as a system 100 utilizing a dye-sensitized solar cell, in which the photoelectric conversion element 10 is made to usable for a cell purpose which makes an operation means M to work via an external circuit 6.

In this embodiment, a light-receiving electrode 5 is formed of an electrically conductive support 1, and a photoconductor layer 2 containing semiconductor fine particles to which the dye (metal complex dye) 21 has been adsorbed. The photoconductor layer 2 is designed according to the intended purpose, and it may have a single-layer structure or a multilayer structure. The dye (metal complex dye) 21 in one photoconductor layer may be a single species or a mixture, but as at least one of them, the above-described metal complex dye of the present invention is used. Light incident to the photoconductor layer 2 excites the dye (metal complex dye) 21. The excited dye has electrons having high energy, and these electrons are transferred from the dye (metal complex dye) 21 to a conduction band of the semiconductor fine particles 22, and further reach the electrically conductive support 1 by diffusion. At this time, the dye (metal complex dye) 21 is in an oxidized form. The electrons on the electrode, while working in an external circuit 6, return through the counter electrode 4 to the photoconductor layer 2 in which the oxidized form of the dye (metal complex dye) 21 and the electrolyte exist, to function as the solar cell.

In the present invention, regarding materials for use in the photoelectric conversion element and the dye-sensitized solar cell, and a method of producing each member, ordinary ones in this kind may be adopted, unless otherwise specified, and reference can be made to, for example, U.S. Pat. Nos. 4,927,721, 4,684,537, 5,084,365, 5,350,644, 5,463,057, 5,525,440, JP-A-7-249790, JP-A-2004-220974 or JP-A-2008-135197.

Hereinafter, an outline of main members will be described.

<Photoconductor Layer>

The photoconductor layer is a layer that contains an electrolyte described later and semiconductor fine-particles carrying a sensitizing dye including the following metal complex dye of the present invention.

<<Metal Complex Dye>>

A metal complex dye according to the present invention is represented by the following formula (I).

M(LD)(LA)·(CI)     formula (I)

In formula (I), M represents a metal ion.

LD represents a tridentate ligand represented by any one of the following formulas (DL-1) to (DL-4).

LA represents a tridentate ligand represented by the following formula (AL).

CI represents a counter ion necessary to neutralize an electric charge.

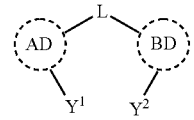

Formula (DL-1)

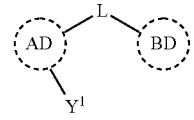

Formula (DL-2)

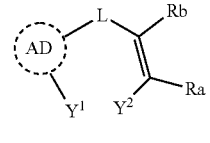

Formula (DL-3)

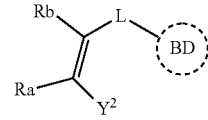

Formula (DL-4)

In the formulas, $Y^1$ and $Y^2$ each independently represent an oxygen atom, a sulfur atom, a substituted or unsubstituted nitrogen atom, or a substituted or unsubstituted phosphorus atom, each of which coordinates with the metal ion M. The ring AD and the ring BD each independently represents a hydrocarbon ring or a hetero ring. L represents a linking group represented by any one of the following formulas (L-1) to (L-4). Ra and Rb each independently represent a substituent.

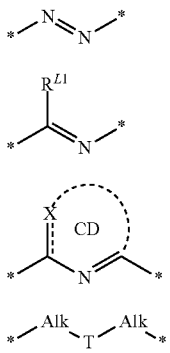

Formula (L-1)

Formula (L-2)

Formula (L-3)

Formula (L-4)

In the formulas, $R^{L1}$ represents a hydrogen atom or a substituent. X represents a nitrogen atom or a carbon atom; the ring CD represents a nitrogen-containing hetero ring containing X. The bond between X and the carbon atom bonded with X and N may be a single bond or a double bond. The ring CD may have a substituent. T represents —O—, —S—, —$NR^{L2}$— or —$PR^{L3}$—; $R^{L2}$ and $R^{L3}$ each independently represent a hydrogen atom or a substituent. Alk represents an alkylene group, which may have a substituent.

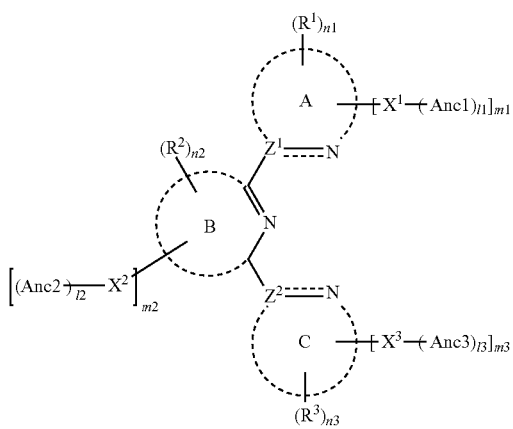

Formula (AL)

In the formula, the ring A, the ring B, and the ring C each independently represent a nitrogen-containing aromatic hetero ring. Herein, the bond between $Z^1$ and N and the bond between $Z^2$ and N may be a single bond or a double bond. $Z^1$ and $Z^2$ each independently represent a carbon atom or a nitrogen atom.

Anc1 to Anc3 each independently represent —$CO_2H$, —$SO_3H$, —$PO_3H_2$, —OH, —SH or a salt thereof. $X^1$, $X^2$ and $X^3$ each independently represent a single bond or a linking group. l1 to l3 each independently represent an integer of 1 to 5. m1 and m3 each independently represent an integer of 0 to 4. m2 represent an integer of 0 to 3. The total of m1 to m3 is 1 or more.

$R^1$ to $R^3$ each independently represent a substituent other than Anc1 to Anc3. n1 and n3 each independently represent an integer of 0 to 2. n2 represents 0 or 1.

—Metal Ion M—

M represents a central metal ion of the metal complex dye, and such a metal may be element numbers 6 to 12 on the long-form periodic table of the elements.

Examples of such elements include Ru, Fe, Os, Cu, W, Cr, Mo, Ni, Pd, Pt, Co, Ir, Rh, Re, Mn and Zn.

In the present invention, M is preferably $Os^{2+}$, $Ru^{2+}$, or $Fe^{2+}$, and particularly preferably $Ru^{2+}$ among them.

In addition, in a state of being incorporated in the photoelectric conversion element, the valence of M may be changed by the redox reaction with the surrounding material.

—Ligand LD—

In the present invention, the ligand LD is classified into a donor ligand, and is preferably a ligand which does not have an adsorptive group that adsorbs onto the surface of semiconductor fine particles.

In this connection, even if a group corresponding to the adsorptive group is contained in the ligand, it is contained as a group that bonds to the metal ion and does not adsorb onto the surface of semiconductor fine particles.

In addition, the adsorptive group that adsorbs onto the surface of semiconductor fine particles is a group represented by Anc1 to Anc3 in a ligand LA described later or a group including any of these groups.

In the present invention, the ligand LD is a tridentate ligand represented by any one of the aforementioned formulas (DL-1) to (DL-4).

$Y^1$ and $Y^2$ each independently represent an oxygen atom, a sulfur atom, a substituted or unsubstituted nitrogen atom, or a substituted or unsubstituted phosphorus atom, each of which coordinates with the metal ion M. In these, the nitrogen atom may have a hydrogen atom or a substituent on the nitrogen atom, and the phosphorus atom may have a hydrogen atom or a substituent.

Herein, the substituent which the nitrogen atom and the phosphorus atom may have includes substituent T described later. For the nitrogen atom, an electron-withdrawing substituent is preferable. Examples thereof include an alkyl- or aryl-sulfonyl group, an acyl group, an alkoxycarbonyl group, a carbamoyl group, a sulfamoyl group, and the like, and among them, an alkyl- or aryl-sulfonyl group is preferable, and an alkylsulfonyl group is more preferable. The number of carbon atoms of the substituent is preferably 1 to 10, more preferably 1 to 4, and particularly preferably 1 or 2.

Meanwhile, in the case of the phosphorus atom, a trivalent phosphorus atom may have one substituent; and a five valence phosphorus atom may have oxo group (=O) and at least one substituent, or when an oxo group is not included, the phosphorus atom is substituted with up to three substituents. The substituent that the phosphorus atom may have includes the substituent T described later. A preferred substituent of the phosphorus atom may be an alkyl group, an aryl group, and an alkoxy group. In addition, in the case of the phosphorus atom, a trivalent phosphorus atom is preferred.

$Y^1$ binding to the ring AD and $Y^2$ binding to the ring BD each may preferably be positioned at an adjacent atom (an ortho position) to the site (atom) to which L is bonded to either of these rings.

$Y^1$ and $Y^2$ preferably represent an oxygen atom, a sulfur atom, or a substituted or unsubstituted nitrogen atom, and particularly preferably an oxygen atom.

The hydrocarbon ring for the ring AD and the ring BD may be an aromatic ring, a non-aromatic unsaturated ring, or an alicyclic ring having no unsaturated bond in its ring structure. The hydrocarbon ring is preferably a 5-membered ring or a 6-membered ring, more preferably an aromatic ring, and still more preferably a benzene ring. In addition, in the case of the non-aromatic unsaturated ring, those having a double bond and an oxo group (=O) in the ring are preferable, and as an example, a cyclopentadienone ring may be mentioned. In addition, the hydrocarbon ring may form a fused ring with a hydrocarbon ring or a hetero ring, or may have a substituent. As the substituent, substituent T described below can be mentioned.

The hetero ring for the ring AD and the ring BD preferably includes at least one of nitrogen atom, oxygen, and a sulfur atom as a ring-constituting atom, and a 5-membered ring or a 6-membered ring is preferable. The hetero ring may be an aromatic ring or a non-aromatic ring, and is preferably an aromatic ring or an unsaturated ring having >C(=O), >S(=O), and/or >SO$_2$ as a ring-constituting part structure. Among them, a hetero aromatic ring is preferable, and a nitrogen-containing hetero aromatic ring is particularly preferable. The hetero ring may form a fused-ring with a hydrocarbon ring or another hetero ring. Further, the hetero ring may have a substituent, and such a substituent includes substituent T described below.

Examples of the hetero ring include a pyrrole ring, a pyrazole ring, an imidazole ring, a triazole ring, a tetrazole ring, an oxazole ring, a thiazole ring, an isothiazole ring, a thiadiazole ring, an oxadiazole ring, a 1,2,4-thiadiazole ring, a 1,2,4-oxadiazole ring, a pyridine ring, a pyrazine ring, a pyrimidine ring, a triazine ring, an indole ring, an indazole ring, a benzimidazole ring, a benzoxazole ring, a benzothiazole ring, a pyrazolone ring, a 2-pyridone ring, an uracil ring, a thiophene-1,1-dioxide ring.

Among these hetero rings, preferred are a pyrazole ring, a pyrazolone ring, a 2-pyridone ring, an uracil ring, a triazole ring, a pyrrole ring, an indole ring, an imidazole ring, a benzimidazole ring, and thiophene-1,1-dioxide ring; and more preferred are a pyrazole ring, an imidazole ring, and a triazole ring.

The ring AD and the ring BD preferably represent a benzene ring, a pyrazole ring, an imidazole, or a triazole ring, more preferably a benzene ring, a pyrazole ring, or a triazole ring, and particularly preferably a benzene ring or a pyrazole ring.

In formula (DL-3) and formula (DL-4), Ra and Rb represent a substituent. Such a substituent includes substituent T described below.

Ra preferably represents an alkyl group or an aryl group.

Rb is preferably an electron-withdrawing group; and examples thereof include an acyl group, an alkoxycarbonyl group, an alkyl- or aryl-sulfonyl group, a carbamoyl group, a sulfamoyl group, and a cyano group.

Ra and Rb may be bonded to each other to form a ring, and in this case, it is preferable that, in a partial structure of the ring derived from Rb, a ring-constituting group adjacent to the double bond includes *—C(=O)—. Herein, * is a part bonded to the double bond. In addition, the ring to be formed is preferably a 6-membered ring.

L represents a linking group represented by any one of the aforementioned formulas (L-1) to (L-4).

$R^{L1}$ represents a hydrogen atom or a substituent, and such a substituent includes substituent T described later. $R^{L1}$ preferably represents a hydrogen atom, an alkyl group, an aryl group, or a hetero ring group, more preferably a hydrogen atom, an alkyl group or an aryl group, furthermore preferably a hydrogen atom or an alkyl group, and particularly preferably a hydrogen atom.

X represents a nitrogen atom or a carbon atom, and the ring CD represents a nitrogen-containing hetero ring that contains X.

The nitrogen-containing hetero ring includes at least one nitrogen atom as a ring-constituting atom, and also, preferably includes an oxygen atom and/or a sulfur atom as other hetero atom, and a 5-membered ring or a 6-membered ring is preferable. The hetero ring may be an aromatic ring or a non-aromatic ring, and preferably an aromatic ring.

The nitrogen-containing hetero ring may have a substituent, and such a substituent includes substituent T described later.

As a nitrogen-containing hetero ring for the ring CD, among the examples described for the ring AD and the ring BD, those having a nitrogen atom as a ring-constituting atom can be mentioned.

As the ring CD, a pyridine ring, an imidazole ring, an oxazole ring, a thiazole ring, a thiadiazole ring (for example, a 1,2,4-thiadiazole ring, a 1,3,4-thiadiazole ring), an oxadiazole ring (for example, a 1,2,4-oxadiazole ring, a 1,3,4-oxadiazole ring), a triazine ring (for example, a 1,3,5-triazine ring, a 1,2,4-triazine ring), a pyrimidine ring and a pyrazine ring are preferable; a pyridine ring, a pyrimidine ring, a pyrazine ring, and a triazine ring are more preferable; a pyridine ring, a pyrimidine ring and a triazine ring are still more preferable; a pyridine ring and a triazine ring are particularly preferable; and a triazine ring is most preferable. The ring CD may have a substituent, and as the substituent of the ring CD, the substituent T described later can be used; and an alkyl group, an aryl group, a hetero ring group, an alkoxy group, and an amino group are preferable, and a thiophene ring group and a diarylamino group are more preferable. These substituents may further have a substituent, and such a substituent includes substituent T described later.

T represents —O—, —S—, —NR$^{L2}$— or —PR$^{L3}$—; and R$^{L2}$ and R$^{L3}$ represent a hydrogen atom or a substituent. Such a substituent includes substituent T described later.

R$^{L2}$ preferably represents a hydrogen atom, an alkyl group, or an aryl group, more preferably an alkyl group or an aryl group, and furthermore preferably an aryl group.

R$^{L3}$ preferably represents an oxo group (=O), an alkyl group, an aryl group, a hydroxyl group, an alkoxy group, an aryloxy group, an alkylthio group, an arylthio group, or the like, more preferably an alkyl group or an aryl group, and furthermore preferably an aryl group.

T preferably represents —NR$^{L2}$— or —PR$^{L3}$—.

Alk represents an alkylene group, and the alkylene group may have a substituent. Such a substituent includes substituent T described later, and among them, an alkyl group is preferable.

The number of carbon atoms of the alkylene group is preferably 1 to 10, more preferably 1 to 4, furthermore preferred are methylene, ethylene, and propylene, still preferred are methylene and ethylene, and particularly preferred is methylene.

As L, among the formulas (L-1) to (L-4), the formulas (L-1) to (L-3) are preferred, and the formula (L-1) or (L-3) is more preferred.

In the present invention, when L is formula (L-1) in formulas (DL-1) to (DL-4) representing the ligand LD, the following ligands are preferable as the ligand LD.

(1) A ligand represented by formula (DL-1), in which both of the ring AD and the ring BD are benzene rings, and both of the benzene rings have a substituent other than Y$^1$ and Y$^2$.

Especially, substituents including one or more carbon atoms are preferable. Among them, the case where one of the ring AD and the ring BD has an electron-donating substituent or an electron-withdrawing substituent and the other of the ring AD and the ring BD is unsubstituted; the case where one of the ring AD and the ring BD has an electron-donating substituent and the other of the ring AD and the ring BD has an electron-withdrawing substituent; the case where both of the ring AD and the ring BD have an electron-donating substituent; and the case where both of the ring AD and the ring BD have an electron-withdrawing substituent can be mentioned. The case where one of the ring AD and the BD has an electron-donating substituent or an electron-withdrawing substituent, and the other of the ring AD and the ring BD is unsubstituted; the case where one of the ring AD and the ring BD has an electron-donating substituent and the other of the ring AD and the ring BD has an electron-withdrawing substituent; and the case where both of the ring AD and the ring BD have an electron-donating substituent are preferable. The case where one of the ring AD and the ring BD has an electron-donating substituent or an electron-withdrawing substituent and the other of the ring AD and the ring BD is unsubstituted and the case where both of the ring AD and the ring BD have an electron-donating substituent are more preferable. As the electron-donating substituent, a substituted or unsubstituted alkyl group, a substituted or unsubstituted aryl group, and a substituted or unsubstituted hetero aryl group are more preferable. As the substituent, the substituent T described later can be mentioned.

(2) A ligand represented by formula (DL-1), in which at least one of the ring AD and the ring BD is not a benzene ring, and the ring other than benzene ring has a dissociable hydrogen atom and coordinates to M by dissociation of the hydrogen atom.

(3) A ligand represented by formula (DL-2), in which the ring AD is a benzene ring having, other than $Y^1$, a substituent having the molecular weight of 20 or more, and the ring BD is a nitrogen-containing hetero aromatic ring.

(4) A ligand represented by formula (DL-2), in which the ring BD coordinates to the metal ion M through an anion of a ring-constituting atom of the hydrocarbon ring or the hetero ring.

(5) A ligand represented by formula (DL-2), in which the ring AD is a hetero ring.

(6) A ligand represented by formula (DL-3)

(7) A ligand represented by formula (DL-4)

Further, when L is formula (L-3) in formulas (DL-1) to (DL-4) representing the ligand LD, the following ligands are preferable as the ligand LD.

(1) A ligand represented by formula (DL-1), in which both of the ring AD and the ring BD are benzene rings, and both of the benzene rings have a substituent other than $Y^1$ and $Y^2$.

Especially, substituents including one or more carbon atoms are preferable. Among them, the case where one of the ring AD and the ring BD has an electron-donating substituent or an electron-withdrawing substituent and the other of the ring AD and the ring BD is unsubstituted; the case where one of the ring AD and the ring BD has an electron-donating substituent and the other of the ring AD and the ring BD has an electron-withdrawing substituent; the case where both of the ring AD and the ring BD have an electron-donating substituent; and the case where both of the ring AD and the ring BD have an electron-withdrawing substituent can be mentioned. The case where one of the ring AD and the BD has an electron-donating substituent or an electron-withdrawing substituent, and the other of the ring AD and the ring BD is unsubstituted; the case where one of the ring AD and the ring BD has an electron-donating substituent and the other of the ring AD and the ring BD has an electron-withdrawing substituent; and the case where both have an electron-donating substituent are preferable. The case where one of the ring AD and the ring BD has an electron-donating substituent or an electron-withdrawing substituent and the other of the ring AD and the ring BD is unsubstituted and the case where both have an electron-donating substituent are more preferable. As the electron-donating substituent, a substituted or unsubstituted alkyl group, a substituted or unsubstituted aryl group, and a substituted or unsubstituted hetero aryl group are more preferable. As the substituent, the substituent T described later can be mentioned.

(2) A ligand represented by formula (DL-2), in which the ring AD and the ring BD are any one of a benzene ring, a pyrazole ring, an imidazole ring, and a triazole ring, the ring BD has a dissociable hydrogen atom and bonds to M by dissociation of the hydrogen atom, and at least one of the ring AD and the ring BD has a substituent other than $Y^1$ and $Y^2$.

Especially, the substituents including one or more carbon atoms are preferable. Among them, the case where one of the ring AD and the ring BD has an electron-donating substituent or an electron-withdrawing substituent and the other of the ring AD and the ring BD is unsubstituted; the case where one of the ring AD and the ring BD has an electron-donating substituent and the other of the ring AD and the ring BD has an electron-withdrawing substituent; the case where both of the ring AD and the ring BD have an electron-donating substituent; and the case where both of the ring AD and the ring BD have an electron-withdrawing substituent can be mentioned. The case where one of the ring AD and the BD has an electron-donating substituent or an electron-withdrawing substituent, and the other of the ring AD and the ring BD is unsubstituted; the case where one of the ring AD and the ring BD has an electron-donating substituent and the other of the ring AD and the ring BD has an electron-withdrawing substituent; and the case where both have an electron-donating substituent are preferable. The case where one of the ring AD and the ring BD has an electron-donating substituent or an electron-withdrawing substituent and the other of the ring AD and the ring BD is unsubstituted, and the case where both have an electron-donating substituent are more preferable. As the electron-donating substituent, a substituted or unsubstituted alkyl group, a substituted or unsubstituted aryl group, and a substituted or unsubstituted hetero aryl group are more preferable. As the substituent, the substituent T described later can be mentioned.

(3) A ligand represented by formula (DL-3)

(4) A ligand represented by formula (DL-4)

In the present invention, the ligand LD is preferably a ligand, in which L is formula (L-1) or formula (L-3). When L is formula (L-1), preferred are the cases wherein, in formula (DL-1), the ring AD and the ring BD each independently represent a benzene ring, a pyrazole ring, or an imidazole ring, $Y^1$ and $Y^2$ each independently represent —O⁻, —S⁻, or —NR⁻ (R represents a hydrogen atom or a substituent); in formula (DL-2), the ring AD is a benzene ring, the ring BD is a benzene ring, a pyrazole ring, an imidazole ring, or a triazole ring, $Y^1$ each independently represent —O⁻, —S⁻, or —NR⁻ (R represents a hydrogen atom or a substituent); in formula (DL-3), the ring AD is a benzene ring, and $Y^1$ and $Y^2$ each independently represent —O⁻, —S⁻, or —NR⁻ (R represents a hydrogen atom or a substituent). When L is formula (L-3), preferred are the cases wherein, in formula (DL-1), the ring AD and the ring BD are benzene rings, $Y^1$ and $Y^2$ each independently represent —O⁻, —S⁻, or —NR⁻ (R represents a hydrogen atom or a substituent); and in formula (DL-2), the ring AD is a benzene ring, the ring BD is a benzene ring, a pyrazole ring, an imidazole ring, or a triazole ring, and $Y^1$ represents —O⁻, —S⁻, or —NR⁻ (R represents a hydrogen atom or a substituent). The ligand LD is more preferably a ligand, in which L is formula (L-3), and, in formula (DL-1), the ring AD and the ring BD are benzene rings, $Y^1$ and $Y^2$ each independently represent —O⁻, —S⁻, or —NR⁻ (R represents a hydrogen atom or a substituent); and in formula (DL-2), the ring AD is a benzene ring, the ring BD is a benzene ring, a pyrazole ring, an imidazole ring, or a triazole ring, and $Y^1$ represents —O⁻, —S⁻, or —NR⁻ (R represents a hydrogen atom or a substituent). The ligand LD is further more preferably a ligand, in which L is formula (L-3), and, in formula (DL-2), the ring AD is a benzene ring, the ring BD is a benzene ring, a pyrazole ring, an imidazole ring, or a triazole ring, and $Y^1$ represents —O⁻, —S⁻, or —NR⁻ (R represents a hydrogen atom or a substituent).

Specific examples of the ligand LD are shown below, but the present invention is not limited to these.

In addition, "*" in the below-shown Chemical Structure indicates the site bonded with L, and "—" in the Chemical Structure represented by L indicates a single bond.

Here, $Y^1$ in the ring AD and $Y^2$ in the ring BD are shown as "—O", "—S", or "—N—SO₂CH₃", and coordinates to the metal ion M, but these are "—O⁻", "—S⁻", and "—N⁻—SO₂CH₃" when consider the ligand itself.

Ligand Represented by Formula (DL-1)

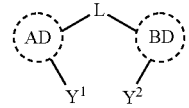

Formula (DL-1)

Ring AD-L-Ring BD

| LD No. | Ring AD | L | Ring BD |
|---|---|---|---|
| DL-1-1 | ⌬–* (O) | —N=N— | *–⌬ (O) |
| DL-1-2 | ⌬–* (O) | —N=N— | pentyl-phenyl-*–O |
| DL-1-3 | pentyl-phenyl-*–O | —N=N— | pentyl-phenyl-*–O |
| DL-1-4 | tert-butyl-phenyl-*–O | —N=N— | tert-butyl-phenyl-*–O |
| DL-1-5 | ⌬–* (O) | —N=N— | CF₃-phenyl-*–O |

-continued
| LD No. | Ring AD | L | Ring BD |
|---|---|---|---|
| DL-1-6 | 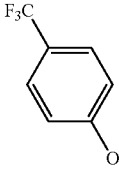 | —N=N— | 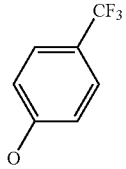 |
| DL-1-7 | 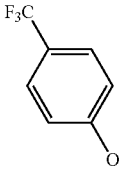 | —N=N— | 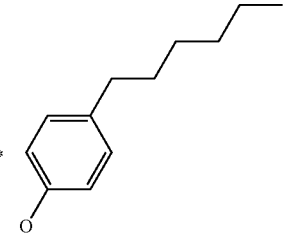 |
| DL-1-8 | 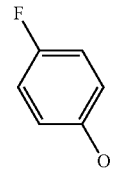 | —N=N— | 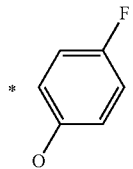 |
| DL-1-9 | 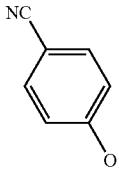 | —N=N— | 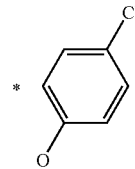 |
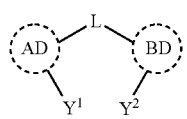
Formula (DL-1)
Ring AD-L-Ring BD
| LD No. | Ring AD | L | Ring BD |
|---|---|---|---|
| DL-1-10 | 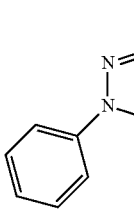 | —N=N— | 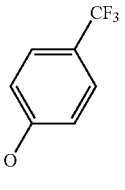 |
| DL-1-11 | 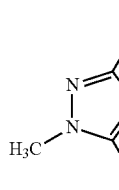 | —N=N— | 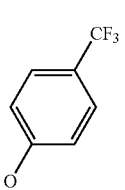 |
-continued
| LD No. | Ring AD | L | Ring BD |
|---|---|---|---|
| DL-1-12 | 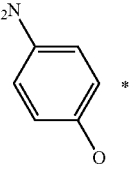 | —N=N— | 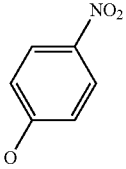 |
| DL-1-13 | 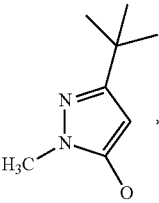 | —N=N— | 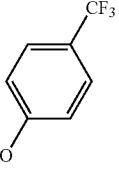 |
| DL-1-14 | 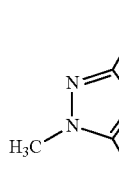 | —N=N— | 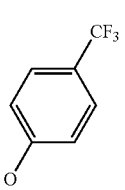 |

-continued

| LD No. | Ring AD | L | Ring BD |
|---|---|---|---|
| DL-1-15 | 1,2-dimethylpyrazolidine-3,5-dione (H₃C-N, N-CH₃, with two C=O) * | —N=N— | 4-(trifluoromethyl)phenyl with O * |
| DL-1-16 | 1,2-diphenylpyrazolidine-3,5-dione * | —N=N— | 4-(trifluoromethyl)phenyl with O * |
| DL-1-17 | 3-cyano-4-methyl-1-methyl-6-oxo-pyridin-2(1H)-one * | —N=N— | 4-(trifluoromethyl)phenyl with O * |

-continued

| LD No. | Ring AD | L | Ring BD |
|---|---|---|---|
| DL-1-18 | 1,3-dimethylpyrimidine-2,4,6-trione * | —N=N— | 4-(trifluoromethyl)phenyl with O * |

Formula (DL-1)

Ring AD—L—Ring BD

| LD No. | Ring AD | L | Ring BD |
|---|---|---|---|
| DL-1-19 | 1,3-dioxo-indene * | —N=N— | 4-(trifluoromethyl)phenyl with O * |
| DL-1-20 | 1,1-dioxo-benzothiophen-3-ol * | —N=N— | 4-(trifluoromethyl)phenyl with O * |
| DL-1-21 | phenol * | —N=CH— | phenol * |
| DL-1-22 | phenol * | —N=CH— | 4-hexylphenol * |

-continued
| LD No. | Ring AD | L | Ring BD |
|---|---|---|---|
| DL-1-23 | 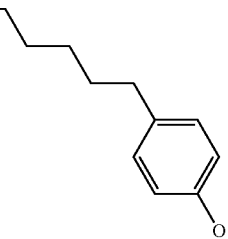 | —N=CH— | 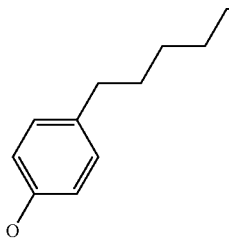 |
| DL-1-24 | 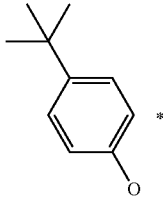 | —N=CH— | 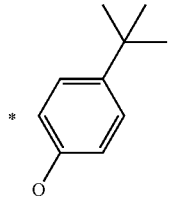 |
| DL-1-25 | 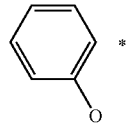 | —N=CH— | 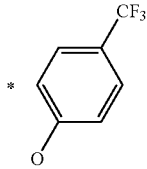 |
| DL-1-26 | 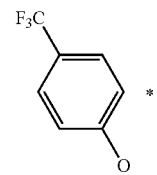 | —N=CH— | 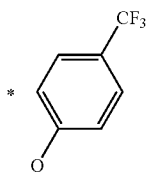 |
| DL-1-27 | 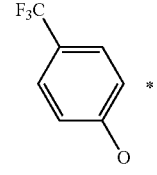 | —N=CH— | 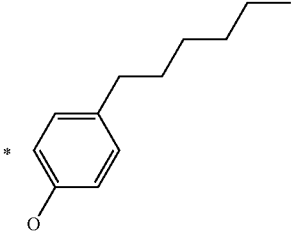 |
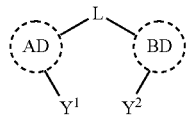
Formula (DL-1)
Ring AD-L-Ring BD
| LD No. | Ring AD | L | Ring BD |
|---|---|---|---|
| DL-1-28 | 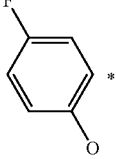 | —N=CH— | 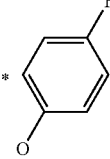 |

-continued
| LD No. | Ring AD | L | Ring BD |
|---|---|---|---|
| DL-1-29 | 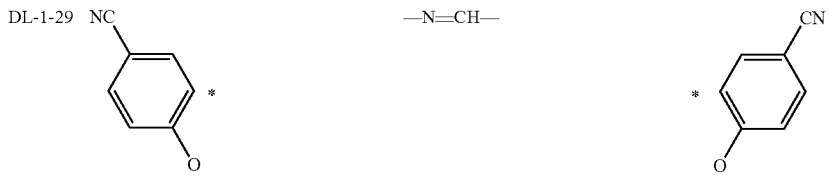 | —N=CH— | |
| DL-1-30 | 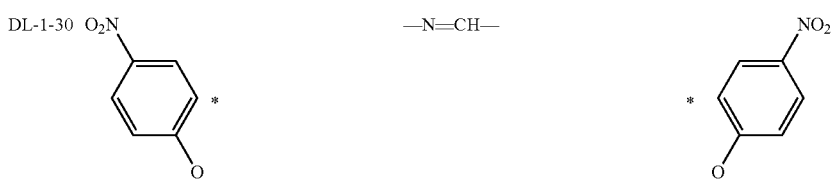 | —N=CH— | |
| DL-1-31 | 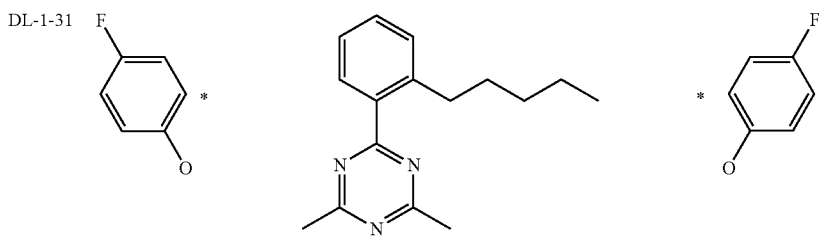 | | |
| DL-1-32 | 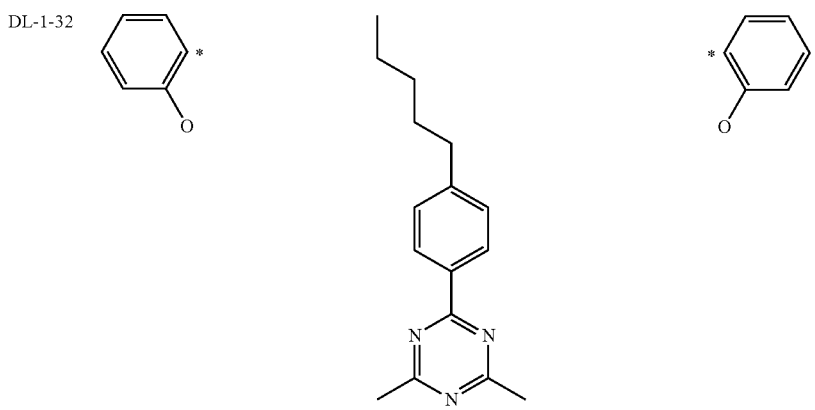 | | |
| DL-1-33 | 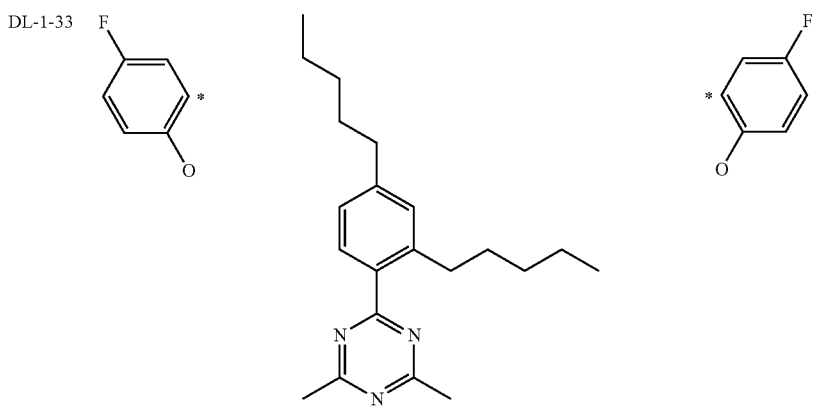 | | |

| LD No. | Ring AD | L | Ring BD |
|---|---|---|---|
| DL-1-34 | 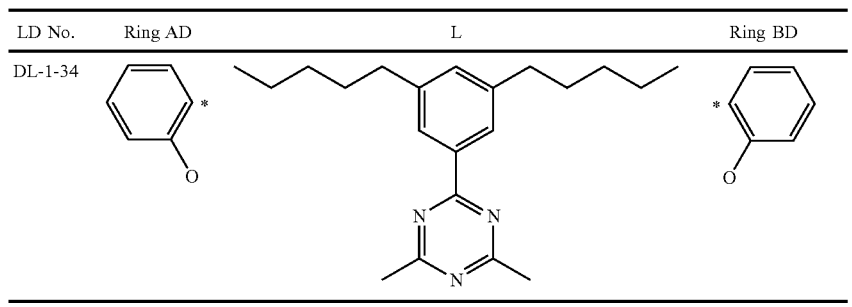 | | |
Formula (DL-1)
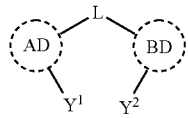
Ring AD-L-Ring BD
| LD No. | Ring AD | L | Ring BD |
|---|---|---|---|
| DL-1-35 | 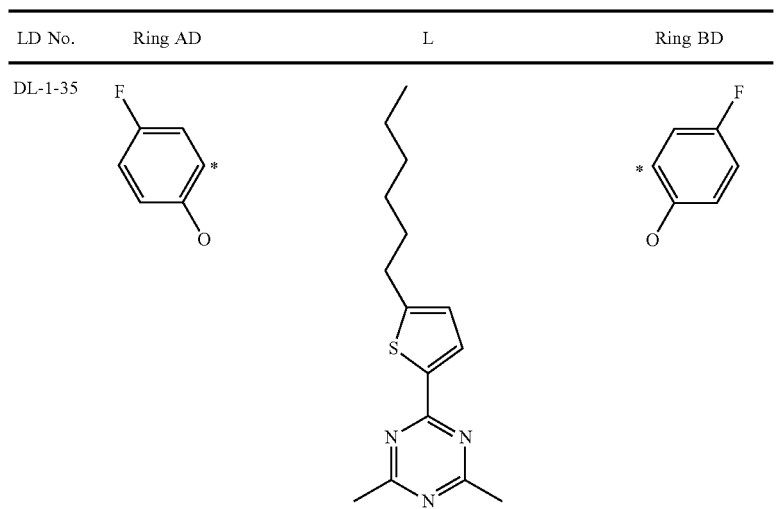 | | |
| DL-1-36 | 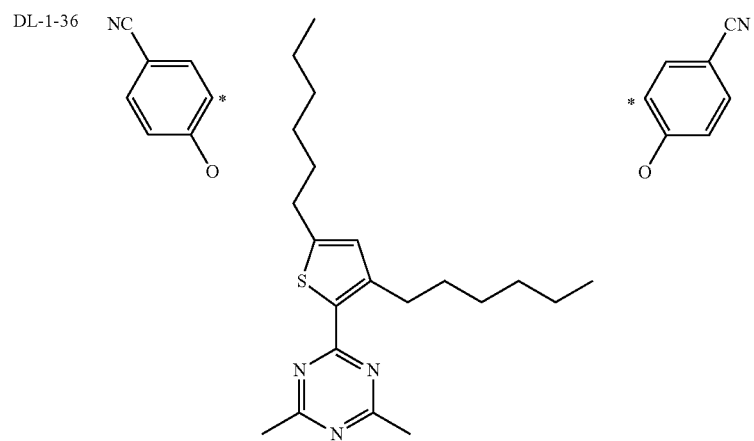 | | |

| LD No. | Ring AD | L | Ring BD |
|---|---|---|---|
| DL-1-37 | 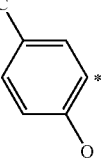 | 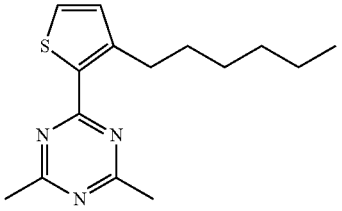 | 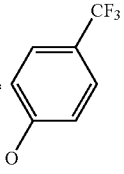 |
| DL-1-38 | 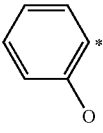 | 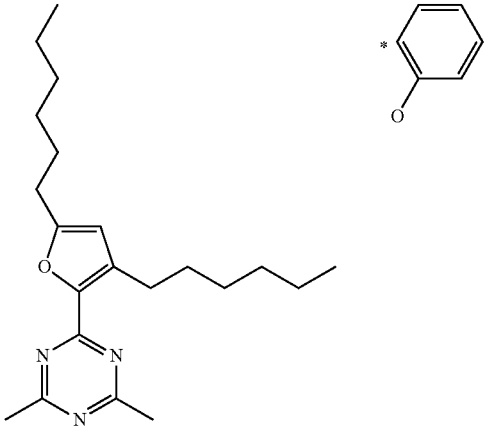 | 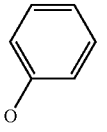 |
| DL-1-39 | 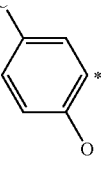 | 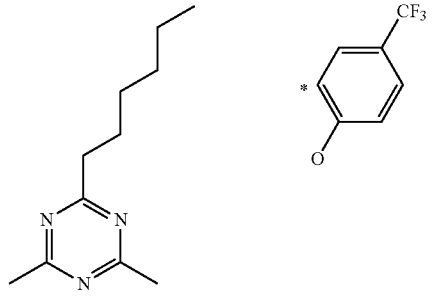 | 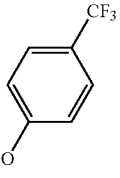 |
| DL-1-40 | 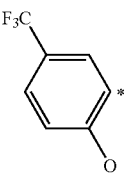 | 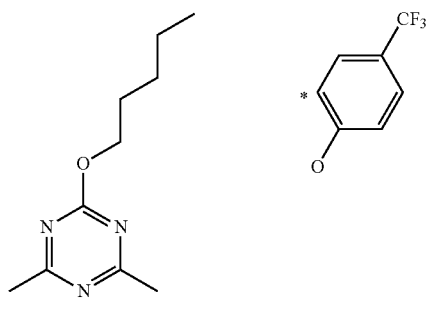 | 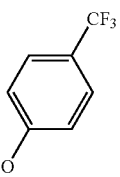 |
| DL-1-41 | 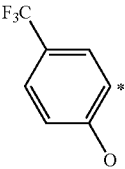 | 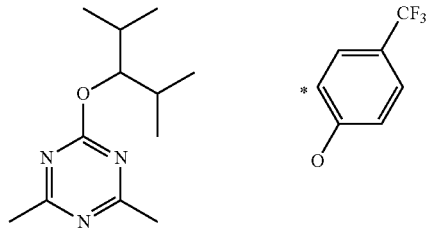 | 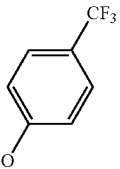 |

Fomula (DL-1)
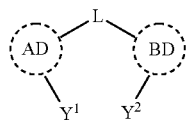
Ring AD-L-Ring BD
| LD No. | Ring AD | L | Ring BD |
|---|---|---|---|
| DL-1-42 | | | |
| DL-1-43 | | | |
| DL-1-44 | | | |
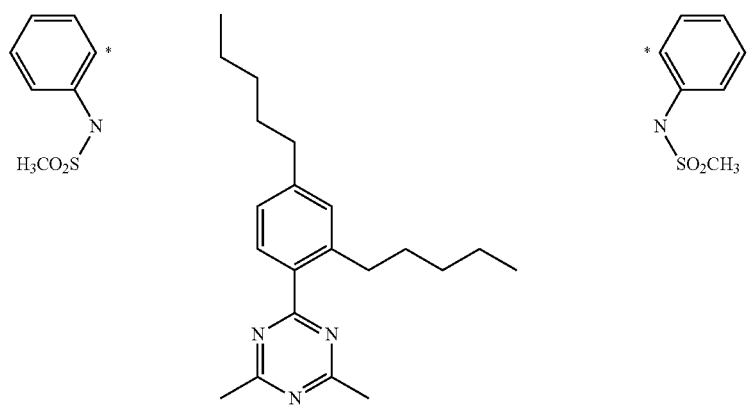
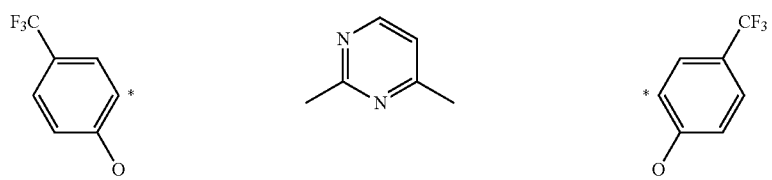

| LD No. | Ring AD | L | Ring BD |
|---|---|---|---|
| DL-1-45 | 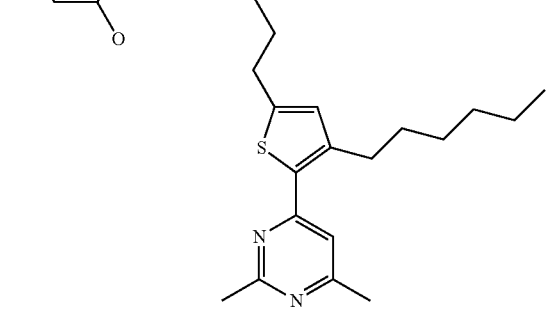 |  | 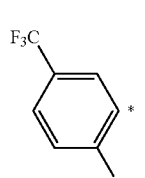 |
| DL-1-46 | 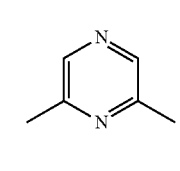 | 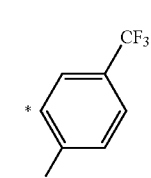 | 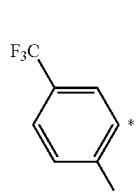 |
| DL-1-47 | 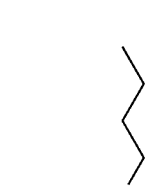 | 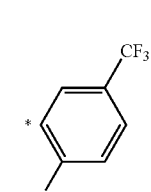 | 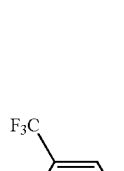 |
| DL-1-48 |  |  |  |

Formula (DL-1)
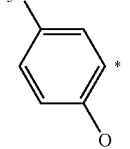
Ring AD-L-Ring BD
| LD No. | Ring AD | L | Ring BD |
|---|---|---|---|
| DL-1-49 | 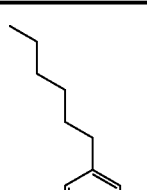 | 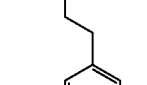 | 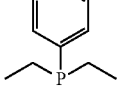 |
| DL-1-50 | 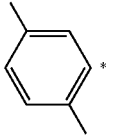 |  | 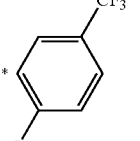 |
| DL-1-51 | 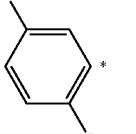 |  | 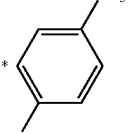 |
| DL-1-52 | 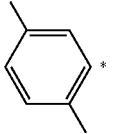 |  | 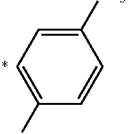 |
| DL-1-53 | 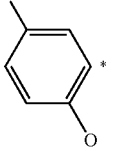 |  | 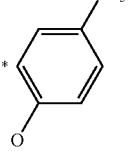 |
| DL-1-54 | 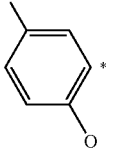 |  | 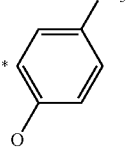 |
-continued
| LD No. | Ring AD | L | Ring BD |
|---|---|---|---|
| DL-1-55 | 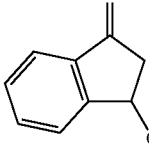 | 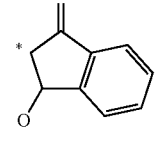 | 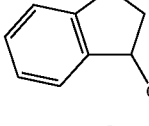 |
| DL-1-56 | 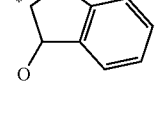 | —N≡N— | 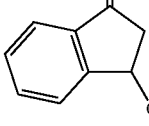 |
Formula (DL-1)
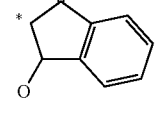
Ring AD-L-Ring BD
| LD No. | Ring AD | L | Ring BD |
|---|---|---|---|
| DL-1-57 | 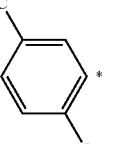 | —N≡N— | 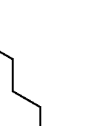 |
| DL-1-58 | 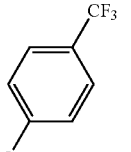 | —N═CH— | |
| DL-1-59 | 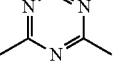 | | |

-continued
| LD No. | Ring AD | L | Ring BD |
|---|---|---|---|
| DL-1-60 | 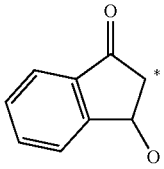 | 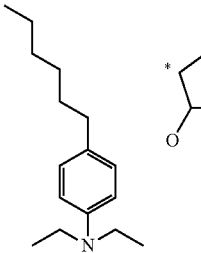 | 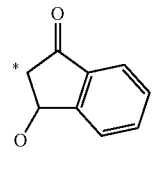 |
Formula (DL-1)
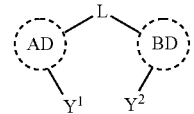
Ring AD-L-Ring BD
| LD No. | Ring AD | L | Ring BD |
|---|---|---|---|
| DL-1-61 | 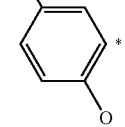 | 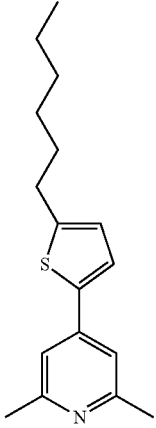 | 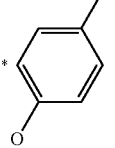 |
| DL-1-62 | | 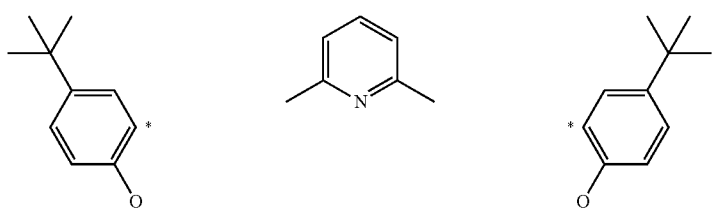 | |
| DL-1-63 | | 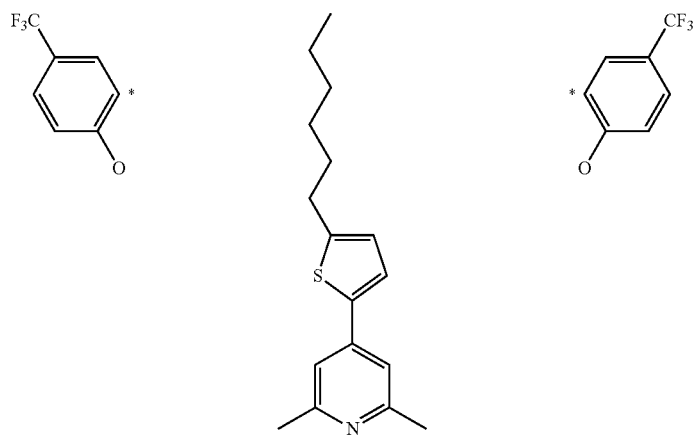 | |

-continued
| LD No. | Ring AD | L | Ring BD |
|---|---|---|---|
| DL-1-64 | 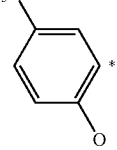 | 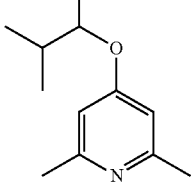 | 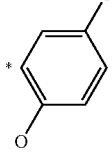 |
| DL-1-65 | 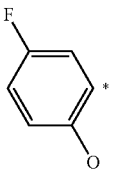 | 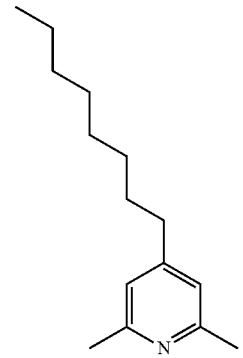 | 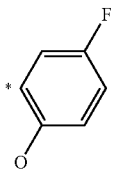 |
| DL-1-66 | 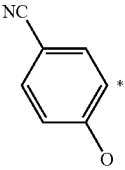 | 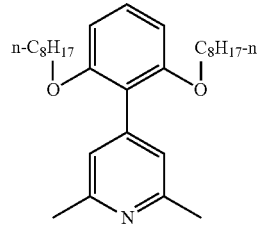 | 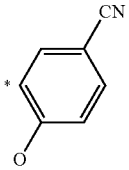 |
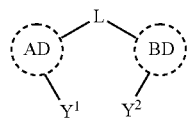
Formula (DL-1)
Ring AD-L-Ring BD
| LD No. | Ring AD | L | Ring BD |
|---|---|---|---|
| DL-1-67 | | | |

-continued
| LD No. | Ring AD | L | Ring BD |
|---|---|---|---|
| DL-1-68 | 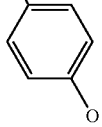 | 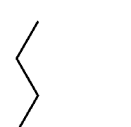 | 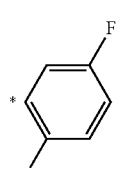 |
| DL-1-69 | 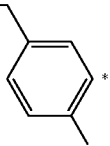 |  | 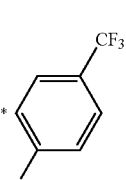 |
| DL-1-70 | 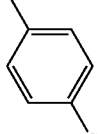 | 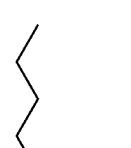 | 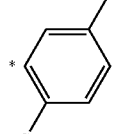 |

Formula (DL-1)
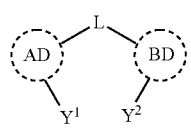
Ligand Represented by Formula (DL-2)
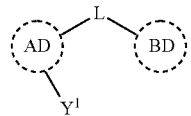
Formula (DL-2)
Ring AD-L-Ring BD
| LD No. | Ring AD | L | Ring BD |
|---|---|---|---|
| DL-1-71 | | | |
| DL-1-72 | | | |
| DL-1-73 | | | |
| DL-1-74 | | | |
| DL-1-75 | | | |

Ring AD-L-Ring BD
| LD No. | Ring AD | L | Ring BD |
|---|---|---|---|
| DL-2-1 | 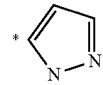 | —N═N— | 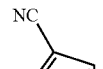 |
| DL-2-2 | 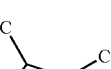 | —N═N— |  |
| DL-2-3 |  | —N═N— | 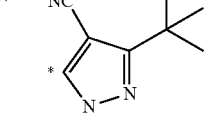 |
| DL-2-4 |  | —N═N— |  |
| DL-2-5 |  | —N═N— |  |
-continued
| LD No. | Ring AD | L | Ring BD |
|---|---|---|---|
| DL-2-6 |  | —N═N— | 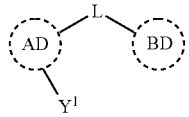 |
| DL-2-7 | 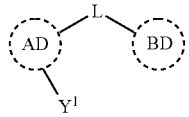 | —N═N— | 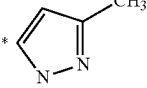 |
| DL-2-8 |  | —N═N— | 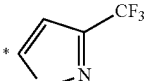 |
Formula (DL-2)
Ring AD-L-Ring BD
| LD No. | Ring AD | L | Ring BD |
|---|---|---|---|
| DL-2-9 | | —N═N— | |
| DL-2-10 | | —N═N— | |

-continued

| LD No. | Ring AD | L | Ring BD |
|---|---|---|---|
| DL-2-11 | (pentyl-phenyl-O*) | —N=N— | 3-methyl-1,2,4-triazole* |
| DL-2-12 | (pentyl-phenyl-O*) | —N=N— | 3-tert-butyl-1,2,4-triazole* |
| DL-2-13 | (pentyl-phenyl-O*) | —N=N— | 3-phenyl-1,2,4-triazole* |
| DL-2-14 | (pentyl-phenyl-O*) | —N=N— | pyrrole* |
| DL-2-15 | (pentyl-phenyl-O*) | —N=N— | indole* |
| DL-2-16 | (pentyl-phenyl-O*) | —N=N— | 5-cyanoindole* |

Formula (DL-2)
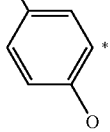
Ring AD-L-Ring BD
| LD No. | Ring AD | L | Ring BD |
|---|---|---|---|
| DL-2-17 | 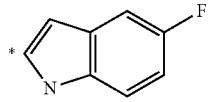 | —N=N— | 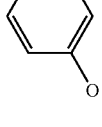 |
| DL-2-18 | 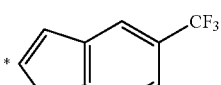 | —N=N— | 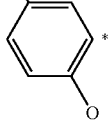 |
| DL-2-19 |  | —N=N— | 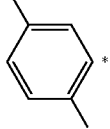 |
| DL-2-20 | 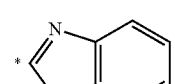 | —N=N— | 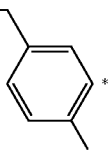 |
| DL-2-21 | 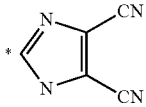 | —N=N— | |

-continued

| LD No. | Ring AD | L | Ring BD |
|---|---|---|---|
| DL-2-22 | (pentyl-phenol with *) | —N=N— | (diethyl imidazole) |
| DL-2-23 | (tert-butyl-methylpyrazolone) | —N=N— | (4-cyanopyrazole) |
| DL-2-24 | (3-methyl-1-phenyl-pyrazolone) | —N=N— | (4-cyanopyrazole) |

Formula (DL-2)

Ring AD-L-Ring BD

| LD No. | Ring AD | L | Ring BD |
|---|---|---|---|
| DL-2-25 | (1-methyl-3-CF₃-pyrazolone) | —N=N— | (4-cyanopyrazole) |
| DL-2-26 | (1,3-dimethyl-pyrazolone) | —N=N— | (4-cyanopyrazole) |
| DL-2-27 | (1,2-dimethyl-pyrazolidinedione) | —N=N— | (4-cyanopyrazole) |
| DL-2-28 | (1,2-diphenyl-pyrazolidinedione) | —N=N— | (4-cyanopyrazole) |
| DL-2-29 | (3-cyano-4-methyl-1-methyl-6-oxo-pyridinone) | —N=N— | (4-cyanopyrazole) |

-continued

| LD No. | Ring AD | L | Ring BD |
|---|---|---|---|
| DL-2-30 | 1,3-dimethyluracil | —N=N— | 4-cyanopyrazole |
| DL-2-31 | 1,3-dioxoindane | —N=N— | 4-cyanopyrazole |
| DL-2-32 | 3-oxo-benzothiophene-S,S-dioxide | —N=N— | 4-cyanopyrazole |

Formula (DL-2)

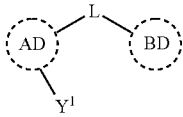

Ring AD-L-Ring BD

| LD No. | Ring AD | L | Ring BD |
|---|---|---|---|
| DL-2-33 | 4-(trifluoromethyl)phenoxy | pentyloxy-(4,6-dimethyl-1,3,5-triazin-2-yl) | 3-(trifluoromethyl)pyrazole |
| DL-2-34 | 4-(trifluoromethyl)phenoxy | (2,4-dimethylpent-3-yl)oxy-(4,6-dimethyl-1,3,5-triazin-2-yl) | 3-(trifluoromethyl)pyrazole |
| DL-2-35 | 4-cyanophenylthio | 2,4-dipentyl-phenyl-(4,6-dimethyl-1,3,5-triazin-2-yl) | 3-(trifluoromethyl)pyrazole |

-continued
| LD No. | Ring AD | L | Ring BD |
|---|---|---|---|
| DL-2-36 | 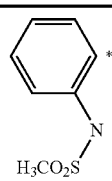 | 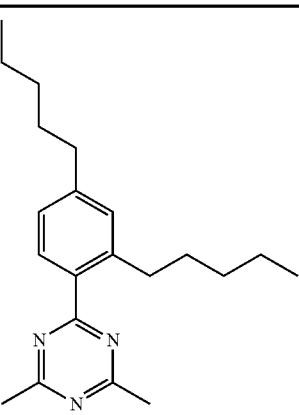 | 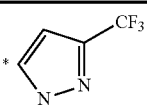 |
| DL-2-37 | 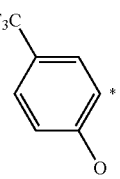 | 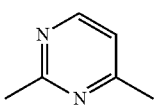 | 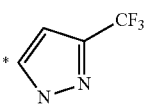 |
| DL-2-38 | 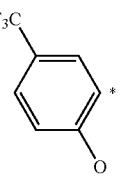 | 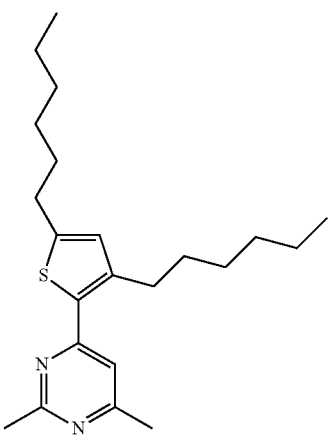 | 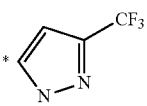 |
Formula (DL-2)
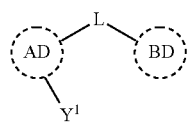
Ring AD-L-Ring BD
| LD No. | Ring AD | L | Ring BD |
|---|---|---|---|
| DL-2-39 | 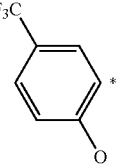 | 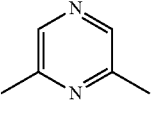 | 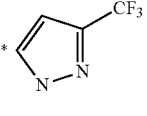 |

-continued
| LD No. | Ring AD | L | Ring BD |
|---|---|---|---|
| DL-2-40 | 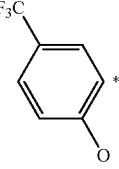 | 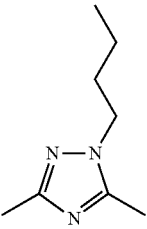 | 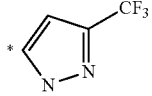 |
| DL-2-41 | 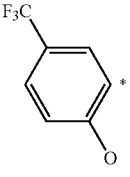 | 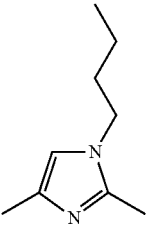 | 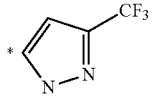 |
| DL-2-42 | 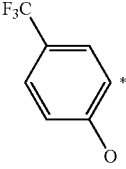 | 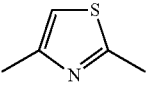 | 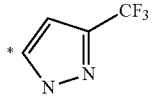 |
| DL-2-43 | 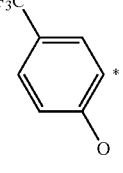 | 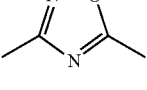 | 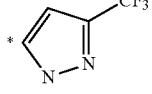 |
| DL-2-44 | 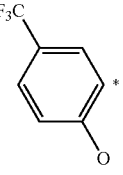 | 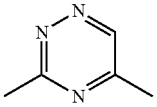 | 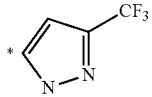 |
| DL-2-45 | 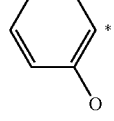 | —N=CH— |  |
| DL-2-46 | 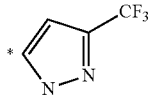 | —CH=N— | 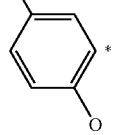 |

Formula (DL-2)
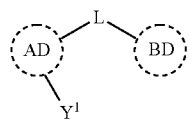
Ring AD-L-Ring BD
| LD No. | Ring AD | L | Ring BD |
|---|---|---|---|
| DL-2-47 | | —CH=N— | |
| | 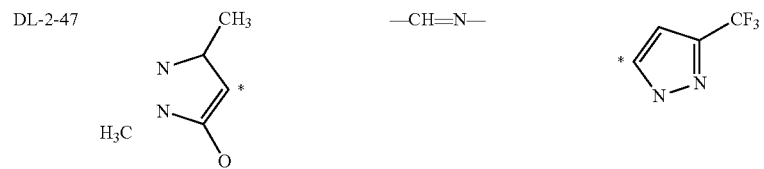 | | |
| DL-2-48 | | | |
| | 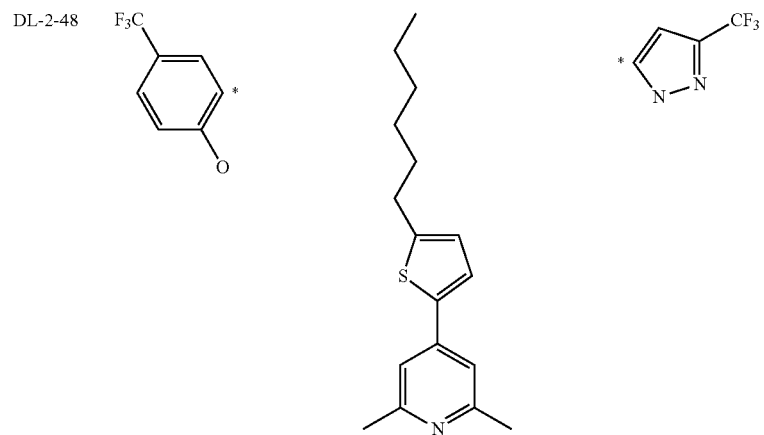 | | |
| DL-2-49 | | | |
| | 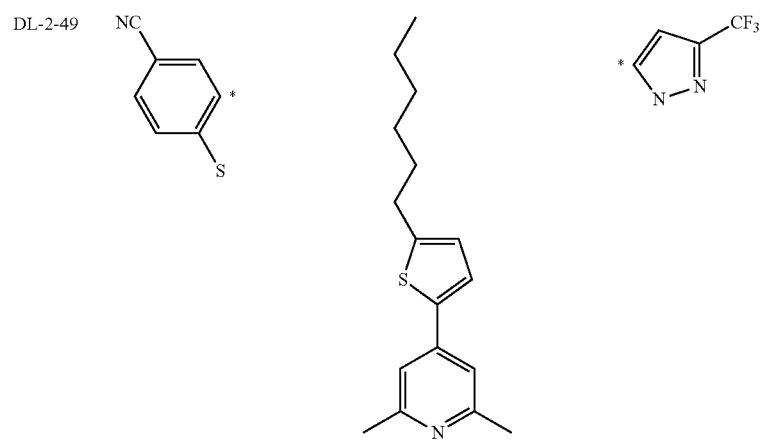 | | |

-continued
| LD No. | Ring AD | L | Ring BD |
|---|---|---|---|
| DL-2-50 | | | |
| DL-2-51 | | | |
| DL-2-52 | | | |
Formula (DL-2)
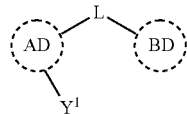
Ring AD-L-Ring BD
| LD No. | Ring AD | L | Ring BD |
|---|---|---|---|
| DL-2-53 | | | |

-continued

| LD No. | Ring AD | L | Ring BD |
|---|---|---|---|
| DL-2-54 | 4-CF₃-phenyl-O- | 3-hexyl-2-(2,6-dimethylpyridin-4-yl)thiophen-2-yl | 3-CF₃-pyrazol-1-yl |
| DL-2-55 | 4-CF₃-phenyl-O- | 3-hexyl-2-(2,6-dimethylpyridin-4-yl)thiophen-2-yl | 3-CF₃-1,2,4-triazol-1-yl |
| DL-2-56 | 4-CF₃-phenyl-O- | 3-hexyl-2-(2,6-dimethylpyridin-4-yl)thiophen-2-yl | 3-methyl-1,2,4-triazol-1-yl |
| DL-2-57 | 4-CF₃-phenyl-O- | 3-hexyl-2-(2,6-dimethylpyridin-4-yl)thiophen-2-yl | 3-methyl-1,2,4-triazol-1-yl |
| DL-2-58 | 4-CF₃-phenyl-O- | 3-hexyl-2-(2,6-dimethylpyridin-4-yl)thiophen-2-yl | 3-methyl-1,2,4-triazol-1-yl |
| DL-2-59 | 4-CF₃-phenyl-O- | 3-hexyl-2-(2,6-dimethylpyridin-4-yl)thiophen-2-yl | 3-tert-butyl-1,2,4-triazol-1-yl |

| LD No. | Ring AD | L | Ring BD |
|---|---|---|---|
| DL-2-60 | 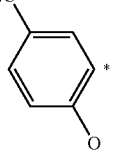 | 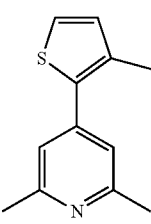 | 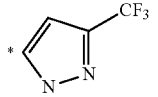 |
| DL-2-61 | 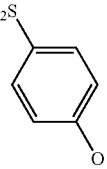 | 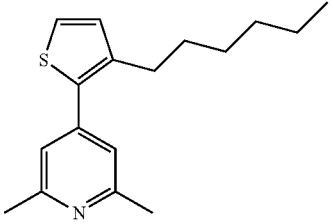 | 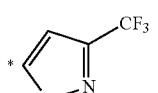 |
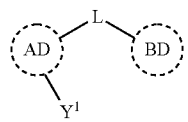
Formula (DL-2)
| LD No. | Ring AD | L | Ring BD |
|---|---|---|---|
| DL-2-62 | 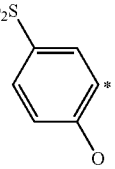 | 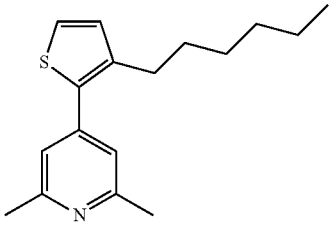 | 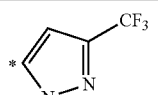 |
| DL-2-63 | 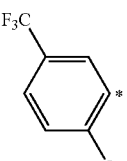 | 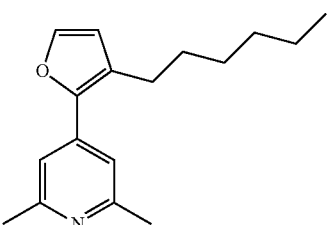 | 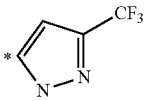 |
| DL-2-64 | 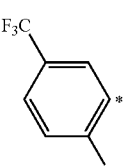 | 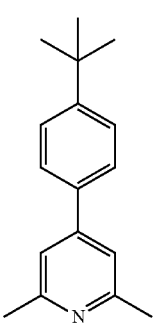 | 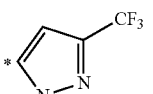 |

-continued
| LD No. | Ring AD | L | Ring BD |
|---|---|---|---|
| DL-2-65 | 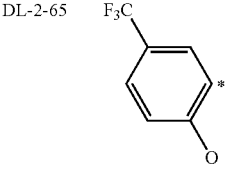 | 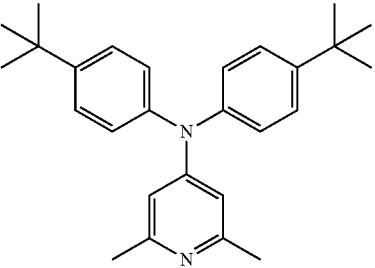 | 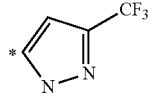 |
| DL-2-66 | 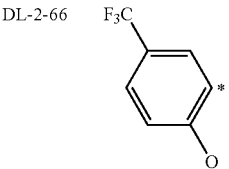 | 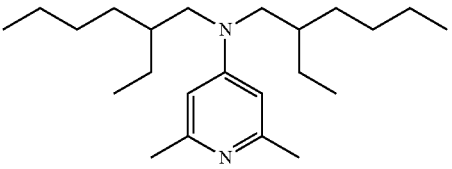 | 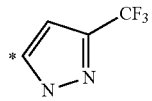 |
| DL-2-67 | 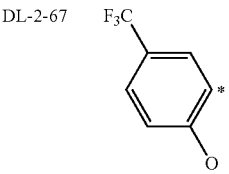 | 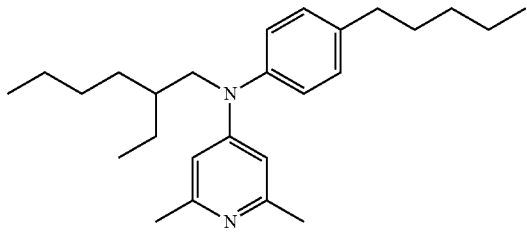 | 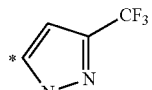 |
| DL-2-68 | 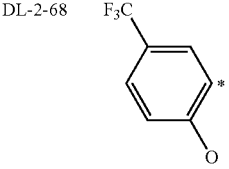 | 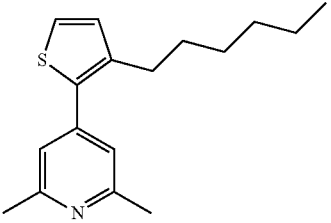 | 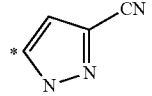 |
| DL-2-69 | 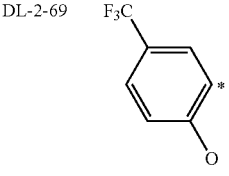 | 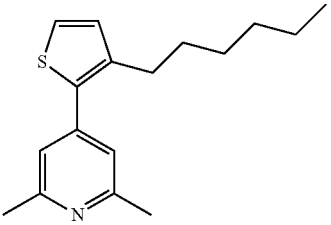 | 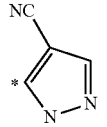 |
| DL-2-70 | 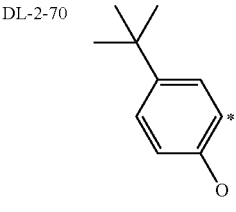 | 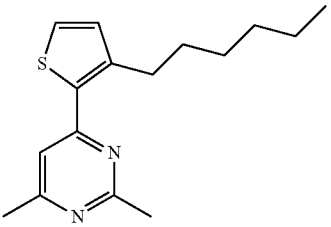 | 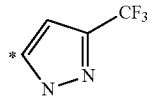 |

Formula (DL-2)
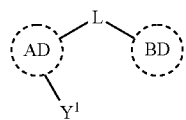
| LD No. | Ring AD | L | Ring BD |
|---|---|---|---|
| DL-2-71 | | | |
| DL-2-72 | | | |
| DL-2-73 | | | |
| DL-2-74 | | | |
| DL-2-75 | | | |

-continued
| LD No. | Ring AD | L | Ring BD |
|---|---|---|---|
| DL-2-76 | 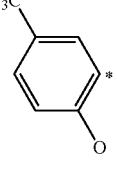 | 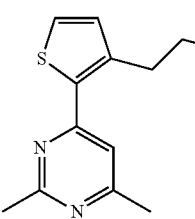 | 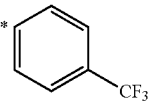 |
| DL-2-77 | 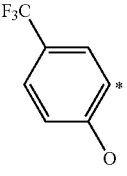 | 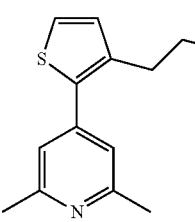 | 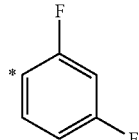 |
| DL-2-78 | 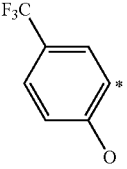 | 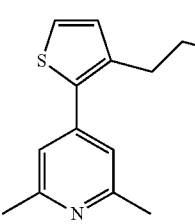 | 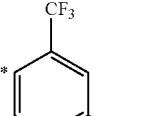 |
| DL-2-79 | 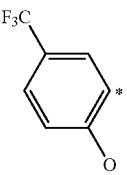 | 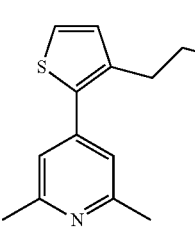 | 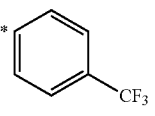 |
| DL-2-80 | 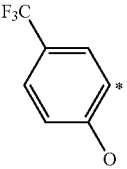 | 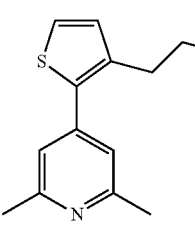 | 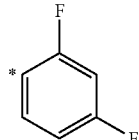 |

Ligand Represented by Formula (DL-3)

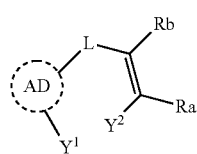

Formula (DL-3)

| LD No. | Ring AD | L | C=C—Y² |
|---|---|---|---|
| DL-3-1 | ![phenol]  | —N=N— | ![acetylacetone group with two CH₃ and two C=O, * marked] |
| DL-3-2 | ![phenol] | —N=N— | ![dibenzoylmethane group with two phenyl, two C=O, * marked] |
| DL-3-3 | ![pentyl-phenol] | —N=N— | ![dibenzoylmethane group with two phenyl, two C=O, * marked] |
| DL-3-4 | ![tert-butyl-phenol] | —N=N— | ![O₂S-phenyl, CH₃, C=O group, * marked] |
| DL-3-5 | ![phenol] | —N=N— | ![N-dihexyl amide with CH₃ and C=O, * marked] |
| DL-3-6 | ![F₃C-phenol] | —N=N— | ![CN, CH₃, C=O group, * marked] |

-continued
| LD No. | Ring AD | L | C=C—Y² |
|---|---|---|---|
| DL-3-7 | 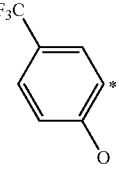 | —N=N— | 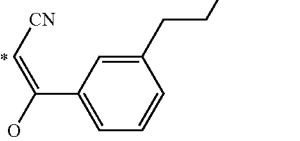 |
| DL-3-8 | 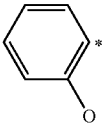 | —N=CH— | 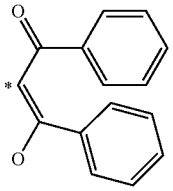 |
| DL-3-9 | 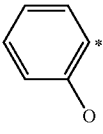 | —CH=N— | 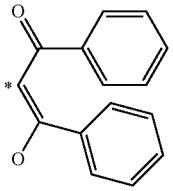 |
Formula (DL-3)
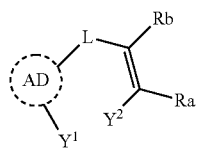
| LD No. | Ring AD | L | C=C—Y² |
|---|---|---|---|
| DL-3-10 | 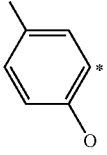 | 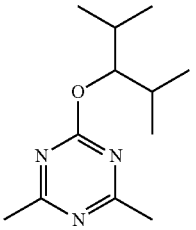 | 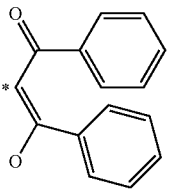 [SMILES: O=C(/C=C(/O)c1ccccc1)c1ccccc1] |
| DL-3-11 | 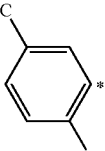 | 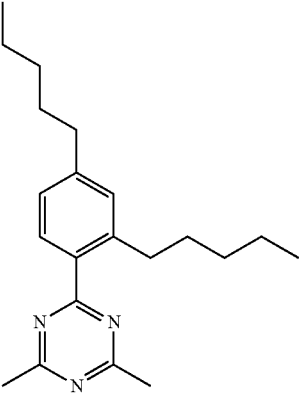 | 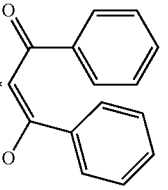 |

-continued
| LD No. | Ring AD | L | C=C—Y² |
|---|---|---|---|
| DL-3-12 | | | |
| DL-3-13 | | | |
| DL-3-14 | | | |
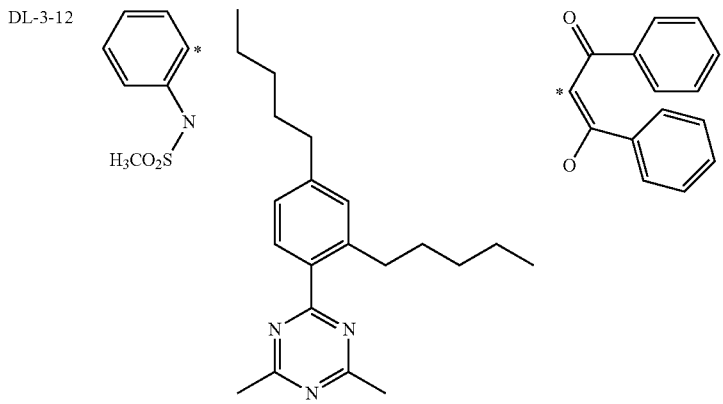
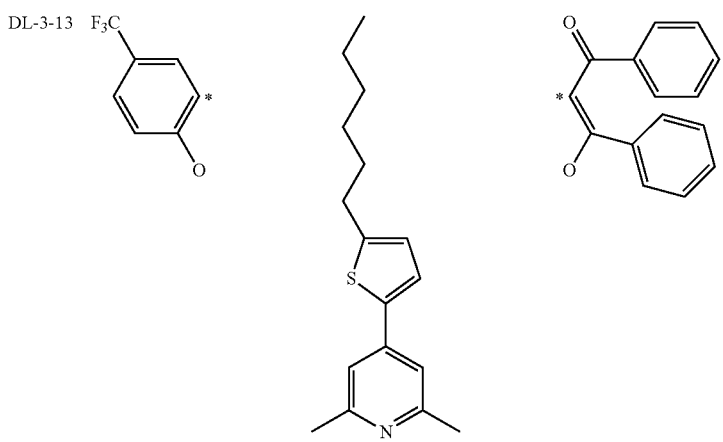
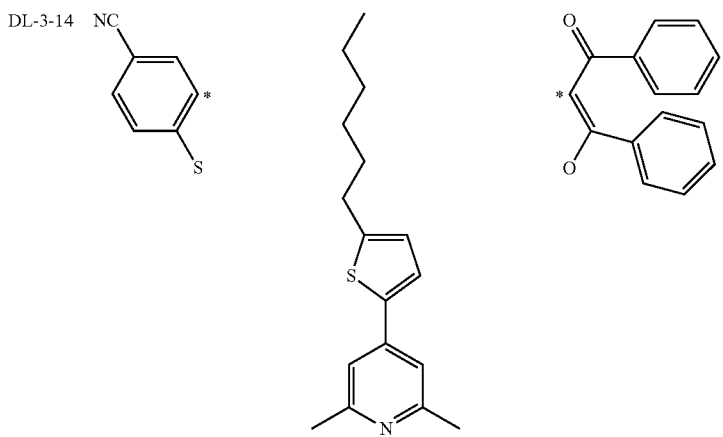

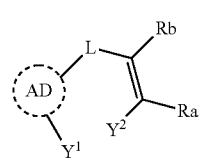
Formula (DL-3)
| LD No. | Ring AD | L | C=C—Y² |
|---|---|---|---|
| DL-3-15 | (phenyl-N(SO₂OCH₃)-*) | (hexylene-thiophene-2,6-dimethylpyridine) | (1,3-diphenyl-1,3-dioxopropenyl-*) |
Ligand Represented by Formula (DL-4)
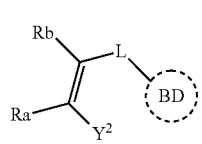
Formula (DL-4)
| LD No. | Y²—C=C | L | Ring BD |
|---|---|---|---|
| DL-4-1 | H₃C-C(O)-C(*)=C-C(O)-CH₃ | —N=N— | 4-cyanopyrazol-*-yl |
| DL-4-2 | Ph-C(O)-C(*)=C-C(O)-Ph | —N=N— | 4-cyanopyrazol-*-yl |
| DL-4-3 | Ph-C(O)-C(*)=C-C(O)-Ph | —N=N— | 5-tert-butyl-1,2,4-triazol-*-yl |

-continued

| LD No. | Y²—C=C | L | Ring BD |
|---|---|---|---|
| DL-4-4 | (phenyl-SO₂)C=C(CH₃)(C=O)* | —N=N— | 3-phenyl-1,2,4-triazole* |
| DL-4-5 | (NC)C=C(CH₃)(C=O)* | —N=N— | pyrrole* |
| DL-4-6 | (3-pentylphenyl)(C=O)C(CN)=C* | —N=N— | indole* (N-H, attached at 2-position) |
| DL-4-7 | (3-pentylphenyl)(C=O)C(CN)=C* | —N=CH— | indole* |
| DL-4-8 | (3-pentylphenyl)(C=O)C(CN)=C* | —CH=N— | 4-cyanopyrazole* |
| DL-4-9 | (3-pentylphenyl)(C=O)C(CN)=C* | 2-(2,4-dipentylphenyl)-4,6-dimethyl-1,3,5-triazine | indazole* |

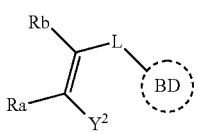

Formula (DL-4)

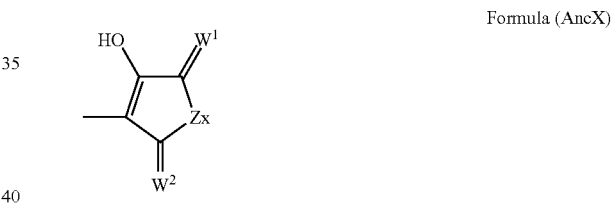

The ligand LD can be synthesized by a general diazotization-coupling reaction, a general imine synthesis reaction, a general cross coupling reaction, and the like.

—Ligand LA—

In the present invention, the ligand LA represents a tridentate ligand represented by the aforementioned formulas (AL).

The ligand LA is a ligand which has an adsorptive group that adsorbs onto the surface of semiconductor fine particles.

In formula (AL), the aromatic hetero ring for the ring A to the ring C may be any rings as long as it has a nitrogen atom as a ring-constituting hetero atom, and also is an aromatic ring.

The aromatic hetero ring for the ring A to the ring C is preferably a 5-membered ring or a 6-membered ring, and the aromatic hetero ring may fuse with an aromatic hydrocarbon ring, an aromatic hetero ring, a non-aromatic hetero ring, or an alicyclic ring. In addition, the ring-constituting hetero atom of the aromatic hetero ring may be 2 to 4 nitrogen atoms, and also may include other hetero atoms, for example, oxygen atom and sulfur atom, in addition to nitrogen atoms.

In the present invention, the aromatic hetero ring is preferably a non-fused 6-membered ring or a 5-membered ring fused with a benzene ring.

Examples of the aromatic hetero ring may include a pyridine ring, a pyrimidine ring, a pyrazine ring, a triazine ring, a quinoline ring, and a quinazoline ring as the 6-membered ring, and a pyrrole ring, an imidazole ring, a pyrazole ring, an oxazole ring, a thiazole ring, an indoline ring, an indazole ring, and a benzothiazole ring as the 5-membered ring.

The ring A and the ring B are preferably an unfused 5-membered ring or 6-membered ring, a fused (preferably, benzo-fused) 5-membered ring, and are preferably the rings exemplified as the aromatic hetero ring.

The ring B is preferably an unfused 6-membered ring, more preferably a pyridine ring, a pyrazine ring, a pyrimidine ring, and a triazole ring, and among them, a pyridine ring is preferable.

In the present invention, as the combinations of these ring A to ring C, it is preferred that the ring A, the ring B, and the ring C be any one of a pyridine ring, a pyrimidine ring, or a thiazole ring; it is more preferred that the ring B be a pyridine ring and the ring A and the ring C be a pyridine ring, a quinoline ring, or a pyrimidine ring; and it is still more preferred that all the ring A to the ring C be pyridine rings.

It is preferable that at least one of $Z^1$ and $Z^2$ is a carbon atom, and it is more preferable that both of $Z^1$ and $Z^2$ are carbon atoms.

Anc1 to Anc3 each are an adsorptive group that adsorbs onto the surface of semiconductor fine particles, and at least one adsorptive group of these adsorbs onto the surface of semiconductor fine particles.

Among them, Anc1 to Anc3 preferably represent —$CO_2H$ or —OH.

$X^1$, $X^2$ and $X^3$ each independently represent a single bond or a linking group.

As the linking group, preferred is a linking group that links, with π conjugation, to the nitrogen-containing aromatic hetero ring to be bonded. As the linking group, divalent groups derived from the substituent T described later can be mentioned.

Examples thereof may preferably include an ethenylene group, an ethynylene group, an arylene group, a hetero aromatic ring group, and a group of any combination of these. These groups may have a substituent, and examples of the substituent include the substituent T described later.

Herein, when Anc1 to Anc3 are —OH, it is preferred that Anc1-$X^1$—, Anc2-$X^2$—, Anc3-$X^3$—, or a partial structure including a part of these linking group $X^1$ to $X^3$ is represented by the following formula (AncX).

Formula (AncX)

In the formula, Zx represents a single bond or —[C(=$W^3$)]nx-. Herein, nx is an integer of 1 to 3. =$W^1$, =$W^2$, and =$W^3$ each independently represent =O or =C($R^{a1}$)($R^{a2}$). $R^{a1}$ and $R^{a2}$ each independently represent a substituent. Further, —OH in formula (AncX) may form a salt.

In formula (AncX), substituents of $R^{a1}$ and $R^{a2}$ in =C($R^{a1}$)($R^{a2}$) for $W^1$ to $W^3$ include the substituent T described later. As $R^{a1}$ and $R^{a2}$, an alkyl group, an aryl group, a heterocyclic group, a cyano group, an acyl group, a sulfonyl group, an alkoxycarbonyl group, an aryloxycarbonyl group, a carbamoyl group, and a sulfamoyl group are more preferable, and an alkyl group, an aryl group, and a cyano group are further preferable.

The group or partial structure represented by formula (AncX) is preferably a group or partial structure represented by any one of the following formulas (Anc-1) to (Anc-5).

(Anc-1)

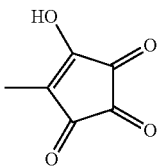
(Anc-2)

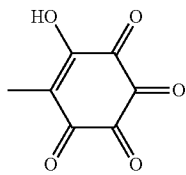
(Anc-3)

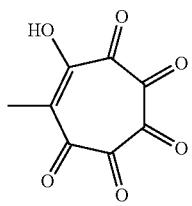
(Anc-4)

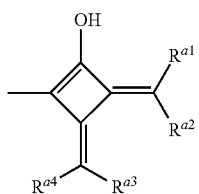
(Anc-5)

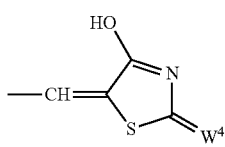

In the formulas, $R^{a1}$ to $R^{a4}$ each independently represent a substituent. In the formulas, —OH may form a salt.

The substituents of $R^{a1}$ to $R^{a4}$ have the same meanings as those of the above-described $R^{a1}$ and $R^{a2}$, and the preferable range thereof are also the same.

Among the groups represented any one of formulas (Anc-1) to (Anc-5), the group represented by formula (Anc-1) or (Anc-5) is preferable, the group represented by formula (Anc-1) is more preferable.

In addition, when Anc1 to Anc3 each are —OH, it is preferred that Anc1-$X^1$—, Anc2-$X^2$—, Anc3-$X^3$—, or a partial structure including a part of these linking group $X^1$ to $X^3$ is represented by the following formula (AncY).

Formula (AncY)

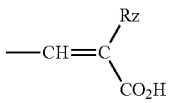

In the formula, $W^4$ has the same meaning as that of $W^1$ to $W^3$ in the above-described formula (AncX), and the preferable range thereof is also the same.

When Anc1 to Anc3 each are —CO$_2$H, it is preferred that Anc1-$X^1$—, Anc2-$X^2$—, Anc3-$X^3$—, or a partial structure including a part of these linking group $X^1$ to $X^3$ is represented by the following formula (AncZ).

Formula (AncZ)

$$-CH=C\begin{matrix}Rz\\CO_2H\end{matrix}$$

In the formula, Rz represents a substituent having the σp value in Hammett's rule of 0.30 or more.

Examples of the group may include a cyano group, an acyl group, a sulfonyl group, an alkoxycarbonyl group, an aryloxycarbonyl group, a carbamoyl group, a sulfamoyl group, a perfluoroalkyl group, and a nitro group.

Rz is preferably a cyano group, an acyl group (preferably an acetyl group), or a perfluoroalkyl group (preferably a trifluoromethyl group), and particularly preferably a cyano group.

In formula (AL), 11 to 13 are an integer of 1 to 5, and 11 to 13 are preferably 1 or 2 and more preferably 1.

m1 and m3 each represent an integer of 0 to 4. m2 represents an integer of 0 to 3. The sum of m1 to m3 is 1 or more. The sum of m1 to m3 is preferably 1 to 3, more preferably 2 or 3, and particularly preferably 3. Among them, it is preferred that any two or three of m1 to m3 are 1, and it is more preferred that all m1 to m3 are 1.

$R^1$ to $R^3$ represent a substituent, and examples of the substituent include substituent T described later. $R^1$ to $R^3$ are preferably an alkyl group, an aryl group, a hetero ring group, an amino group, an alkoxy group, an aryloxy group, an alkylthio group, an arylthio group, and an electron-withdrawing group having a positive Hammett σp value, such as, a halogen atom, a cyano group, and a sulfonyl group. $R^1$ to $R^3$ are more preferably an alkyl group, an aryl group, a hetero ring group, an amino group, a halogen atom, and a cyano group.

n1 and n3 each independently represent an integer of 0 to 2. n2 represents 0 or 1. n1 and n3 are preferably 0 or 1, and n2 is preferably 1. Furthermore preferably, all of n1 to n3 are 0.

The ligand represented by the above formula (AL) is preferably a ligand represented by any one of the following formulas (AL-1) to (AL-4).

Formula (AL-1)

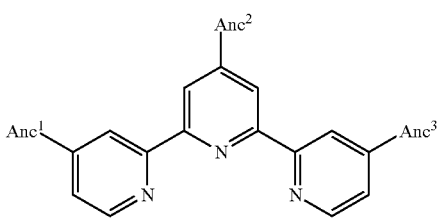

Formula (AL-2)

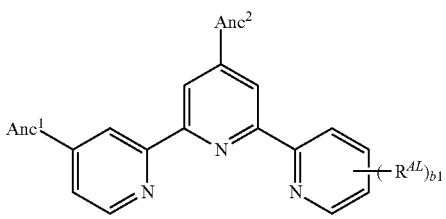

-continued

Formula (AL-3)

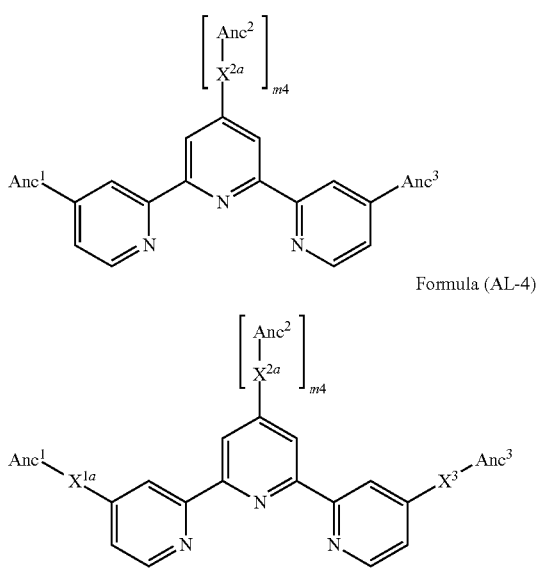

Formula (AL-4)

In the formulas, $Anc^1$ to $Anc^3$ each independently represent —$CO_2H$, —$SO_3H$, —$PO_3H_2$, or a salt thereof. $R^{AL}$ represents a substituent other than $Anc^1$ to $Anc^3$. b1 represent an integer of 0 to 4.

$X^{2a}$ represents —O—, —S—, —NR'—, a divalent saturated aliphatic group, a divalent aromatic hydrocarbon ring group, a divalent non-aromatic hydrocarbon ring group, a divalent aromatic hetero ring group, a divalent non-aromatic hetero ring group, or a linking group formed by any combination of these. Herein R' represents a hydrogen atom or a substituent. $X^{1a}$ represents a linking group. $X^3$ represents a single bond or a linking group. m4 represents 0 or 1.

$Anc^1$ to $Anc^3$ each preferably represent —$CO_2H$ or a salt thereof.

The substituent for $R^{AL}$ may be the substituent T described later, and preferably, an alkyl group, an alkenyl group, an aryl group, and a hetero ring group (preferably a hetero aromatic ring group, and more preferably thiophene ring and furan ring).

b1 preferably represents an integer of 0 to 3, more preferably an integer of 0 to 2, and particularly preferably 0 or 1.

In $X^{2a}$, the substituent of R' includes the substituent T described later. R' preferably represents a hydrogen atom, an alkyl group, an aryl group, and a heterocyclic group.

In addition, the divalent saturated aliphatic group, the divalent aromatic hydrocarbon ring group, the divalent non-aromatic hydrocarbon ring group, the divalent aromatic hetero ring group, and the divalent non-aromatic hetero ring group may have a substituent, and as the substituent, the substituent T described later can be mentioned.

In $X^{2a}$, the divalent saturated aliphatic group may be either of a linear chain and a branched chain. Especially preferred divalent saturated aliphatic group is an alkylene group, and an alkylene group having 1 to 6 carbon atoms, such as, methylene, ethylene, propylene, and butylene can be mentioned.

Examples of the divalent aromatic hydrocarbon ring group may include the group corresponding to the aryl group and the like in the substituent T described later, and specifically, a phenylene group and a naphthylene group.

The divalent non-aromatic hydrocarbon ring group includes a divalent saturated hydrocarbon ring group (a cycloalkylene group), and a divalent unsaturated hydrocarbon ring group which is, for an example, a divalent hydrocarbon ring group having one or two or more of carbon-carbon double bond(s) or carbon-carbon triple bond(s) so as not to satisfy the Hückel's rule. In addition, when the ring-constituting atom includes an oxo group (>C=O), an enol structure can be taken as tautomer, and thus, formally, for example, becomes 6π conjugation, but they are classified into a divalent non-aromatic hydrocarbon ring group.

As the divalent aromatic hetero ring group, a divalent group of any of the rings mentioned as the nitrogen-containing hetero ring group for the Ring A to Ring C can be enumerated. As the aromatic hetero ring in the divalent aromatic hetero ring group, a pyridine ring, a pyrimidine ring, a triazine ring, a triazole ring, a pyrazole ring, a thiophene ring, a benzothiophene ring, and a furan ring can be mentioned.

As the hetero ring group in the divalent non-aromatic hetero ring group, there may be a saturated divalent hetero ring group (for example, as these rings, a pyrrolidine ring, a morpholine ring, and a piperidine ring), a divalent hetero ring group including carbon-carbon double bond and/or carbon-heteroatom double bond which ring is unsaturated and does not satisfy the Hückel's rule (for example, as these rings, a 2H-pyrrole ring, a pyrroline ring, an imidazolidine ring, and a pyrazolidine ring), and a hetero ring group including —SO—, —$SO_2$—, or —C(=O)— in the ring-constituting atoms (for example, as these rings, a thiophene-1-oxide ring, a thiophene-1,1-dioxide ring, and a pyrrolidone ring).

There may be a benzene ring group substituted by an ethenylene group or ethynylene group, or a group having a thiophene ring structure, a group in which two or more of the group having thiophene ring structure are combined, and the like.

From the point that the metal complex dye shows higher photoelectric conversion efficiency (II), $X^{2a}$ is preferably a linear or branched divalent aliphatic hydrocarbon group, a divalent aromatic hydrocarbon ring group, or a divalent aromatic hetero ring group, more preferably a divalent aromatic hydrocarbon ring group, and still more preferably a benzene ring as such a ring.

$X^{1a}$ represents a linking group. Here, a linking group does not include a single bond.

The linking group for $X^{1a}$ and $X^3$ preferably includes the linking group for $X^{2a}$, and a divalent unsaturated hydrocarbon group, such as, an ethenylene group, an ethynylene group, and the like.

The linking group for $X^{1a}$ and $X^3$ is preferably a linking group that links between its atom bonded with $Anc^1$ or $Anc^3$ and the pyridine ring, with π conjugation. By this, improvement of an absorption characteristic may be expected by the extension of π conjugation system. Such a linking group may be an ethenylene group, an ethynylene group, an arylene group, a divalent aromatic hetero ring group, or a linking group of any combination of these groups.

In addition, with respect to the divalent non-aromatic hydrocarbon ring group or the divalent non-aromatic hetero ring group, also preferred are those which can extend π conjugation system. For example, as the divalent non-aromatic hetero ring group, preferred is a divalent unsaturated hetero ring group (a group of a ring having an oxo group (>C=O) and a carbon-carbon double bond, in the ring-constituting atoms), such as, the following formulas (h-1) to (h-4). Here, the carbon-carbon double bond in the ring related to π conjugation may be a carbon-hetero atom double bond (for example, C═N), or a hetero atom-hetero atom double bond (for example, N═N).

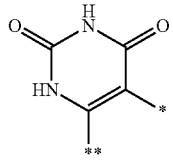
(h-1)

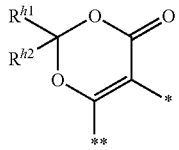
(h-2)

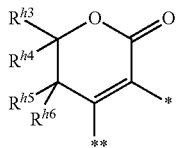
(h-3)

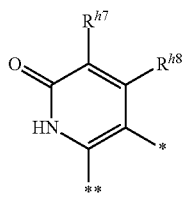
(h-4)

In the formulas, * and ** represent binding sites with the pyridine ring or $Anc^1$ or $Anc^3$, and $R^{h1}$ to $R^{h8}$ each independently represent a hydrogen atom or a substituent. As the substituent for $R^{h1}$ to $R^{h8}$, the substituent T described later can be mentioned.

Among them, the substituent for $R^{h7}$ may be an electron-withdrawing group among the substituents T described later, and for example, preferably a cyano group, and the like.

Examples of $X^{1a}$ and $X^3$ include the linking group for $X^{2a}$, and as described above, preferably a group that links with π conjugation. As such a group, more preferred are an ethenylene group, an ethynylene group, an arylene group (preferably, a phenylene group), a divalent thiophene ring, and any combination of these groups.

Examples thereof may include -ethenylene-phenylene-, -ethynylene-phenylene-, -ethenylene-divalent thiophene ring-, -ethynylene-divalent thiophene ring-, and -divalent thiophene ring-divalent thiophene ring-.

In addition, the linking group may be substituted with the substituent T described later, and among them, may be preferably substituted with an electron-withdrawing substituent. By being substituted with an electron-withdrawing substituent, the molar absorption coefficient of the metal complex dye is increased to improve photoelectric conversion efficiency, and also, reduce performance fluctuation. As such an electron-withdrawing group, for example, a fluoroalkyl group, a halogen atom, an alkylcarbonyl group, an arylcarbonyl group, an alkylsulfonyl group, an arylsulfonyl group, a substituted or unsubstituted amino sulfonyl group, a nitro group, a substituted or unsubstituted amide group, and a cyano group are suitable.

From the point that the metal complex dye exhibits higher photoelectric conversion efficiency (II), $X^{1a}$ and $X^3$ each are preferably an ethynylene group that may have a substituent, a divalent thiophene ring group, an unsaturated hetero ring group having a thiophene skeleton or a linking group of any combination of these groups.

Preferred are an ethynylene group that may have a substituent, and a conjugated group in which 2 to 5 of the ethynylene groups are linked, especially, a group represented by any of the following formulas (e-1) to (e-4); a divalent thiophene ring group, and an unsaturated hetero ring group having a divalent thiophene ring skeleton, and especially, a group represented by the following formulas (s-1) to (s-3).

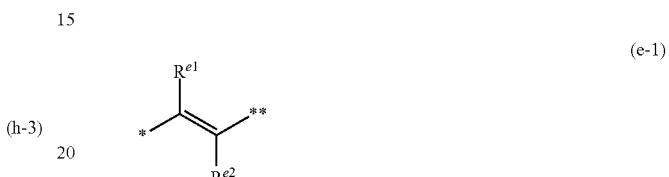
(e-1)

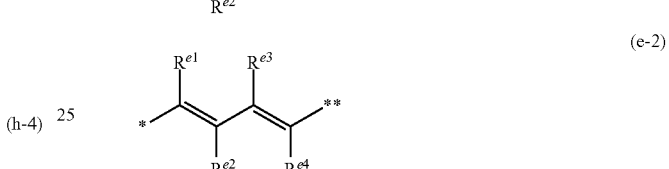
(e-2)

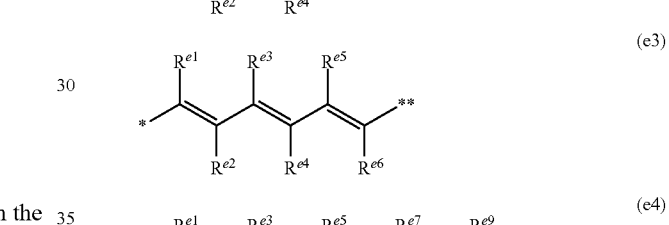
(e3)

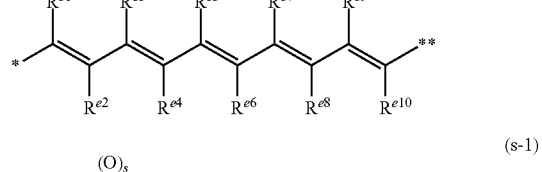
(e4)

(s-1)

(s-2)

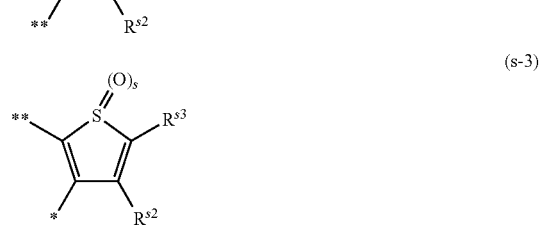
(s-3)

In the formula, * represents a binding site with the pyridine ring, and ** represents a binding site with $Anc^1$ or $Anc^3$. s is an integer of 0 to 2. $R^{e1}$ to $R^{e10}$ and $R^{s1}$ to $R^{s3}$ each independently represent a hydrogen atom or a substituent, and a plurality of substituents may be bonded, directly or by being intervened with a linking group, to form a ring. Here, the substituents of $R^{e1}$ to $R^{e10}$ and $R^{s1}$ to $R^{s3}$ may be the substituent T described later, and among them, an electron-withdrawing group is preferable.

In formulas (AL-3) and (AL-4), m4 represents 0 or 1, and, in terms of durability, m4 preferably represents 1.

Hereinafter, the specific examples of the ligand LA are represented, but the present invention is not limited thereto.

Series 1 of ligand LA

| LA No. | Cy101 | Cy102 | Cy103 |
|---|---|---|---|
| LA-1-1 | | | |
| LA-1-2 | | | |
| LA-1-3 | | | |
| LA-1-4 | | | |
| LA-1-5 | | | |
| LA-1-6 | | | |
| LA-1-7 | | | |

-continued

| LA No. | Cy101 | Cy102 | Cy103 |
|---|---|---|---|
| LA-1-8 | H₂O₃P-(2-methylpyridin-4-yl) | 2,6-dimethylpyridine-4-carboxylic acid (COOH) | (2-methylpyridin-4-yl)-PO₃H₂ |
| LA-1-9 | H₂O₃P-(2-methylpyridin-4-yl) | 2,6-dimethyl-4-(PO₃H₂)pyridine | (2-methylpyridin-4-yl)-PO₃H₂ |
| LA-1-10 | 2-methylpyridine | 2,6-dimethylpyridine | (2-methylpyridin-4-yl)-CH=C(CN)(COOH) |
| LA-1-11 | 2-methylpyridine | 3-(2,6-dimethylpyridin-4-yl)benzoic acid (HOOC) | (2-methylpyridin-4-yl)-CH=C(CN)(COOH) |
| LA-1-12 | 2-methylpyridine | 2,6-dimethylpyridine | (2-methylpyridin-4-yl)-CH=C(SO₂CH₃)(COOH) |
| LA-1-13 | 2-methylpyridine | 2,6-dimethylpyridine | (2-methylpyridin-4-yl)-CH=C(COCH₃)(COOH) |
| LA-1-14 | 2-methylpyridine | 2,6-dimethylpyridine | (2-methylpyridin-4-yl)-CH=C(COC₆H₅)(COOH) |
| LA-1-15 | 2-methylpyridine | 2,6-dimethylpyridine | (2-methylpyridin-4-yl)-CH=(4-hydroxy-2-oxothiazol-5-ylidene) |
| LA-1-16 | 2-methylpyridine | 3-(2,6-dimethylpyridin-4-yl)benzoic acid (HOOC) | (2-methylpyridin-4-yl)-CH=(4-hydroxy-2-oxothiazol-5-ylidene) |

-continued
| | Cy101—Cy102—Cy103 | | |
|---|---|---|---|
| LA No. | Cy101 | Cy102 | Cy103 |
| LA-1-17 | 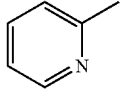 | 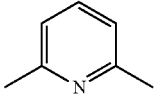 | 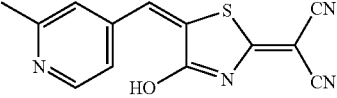 |
| LA-1-18 | 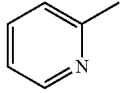 | 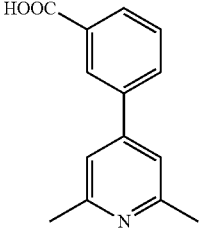 | 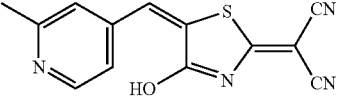 |
| LA-1-19 | 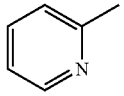 | 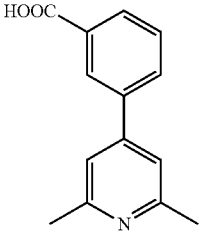 | 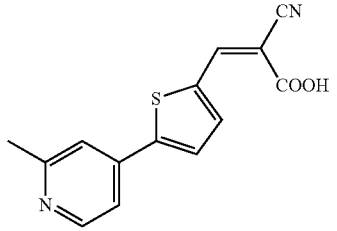 |
| LA-1-20 | 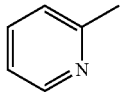 | 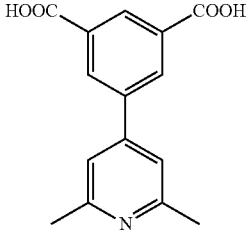 | 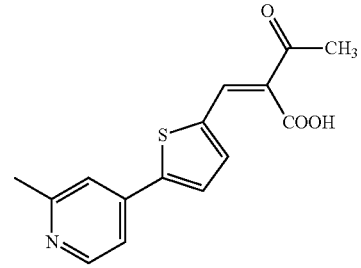 |
| LA-1-21 | 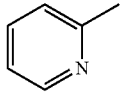 | 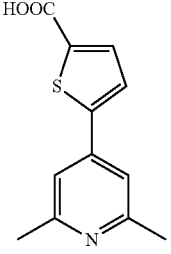 | 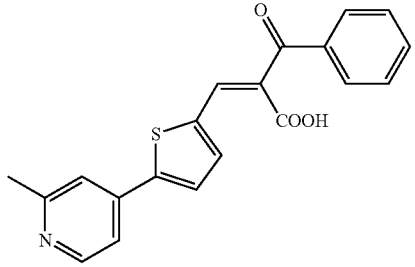 |
| LA-1-22 | 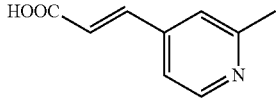 | 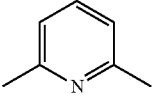 | 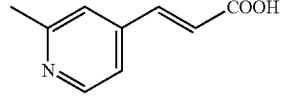 |
| LA-1-23 | 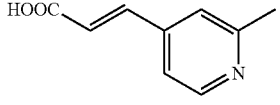 | 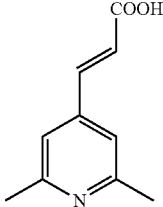 | 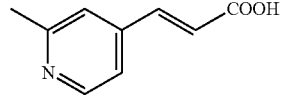 |

-continued

| LA No. | Cy101 | Cy102 | Cy103 |
|---|---|---|---|
| LA-1-24 | | | |
| LA-1-25 | | | |
| LA-1-26 | | | |
| LA-1-27 | | | |
| LA-1-28 | | | |
| LA-1-29 | | | |

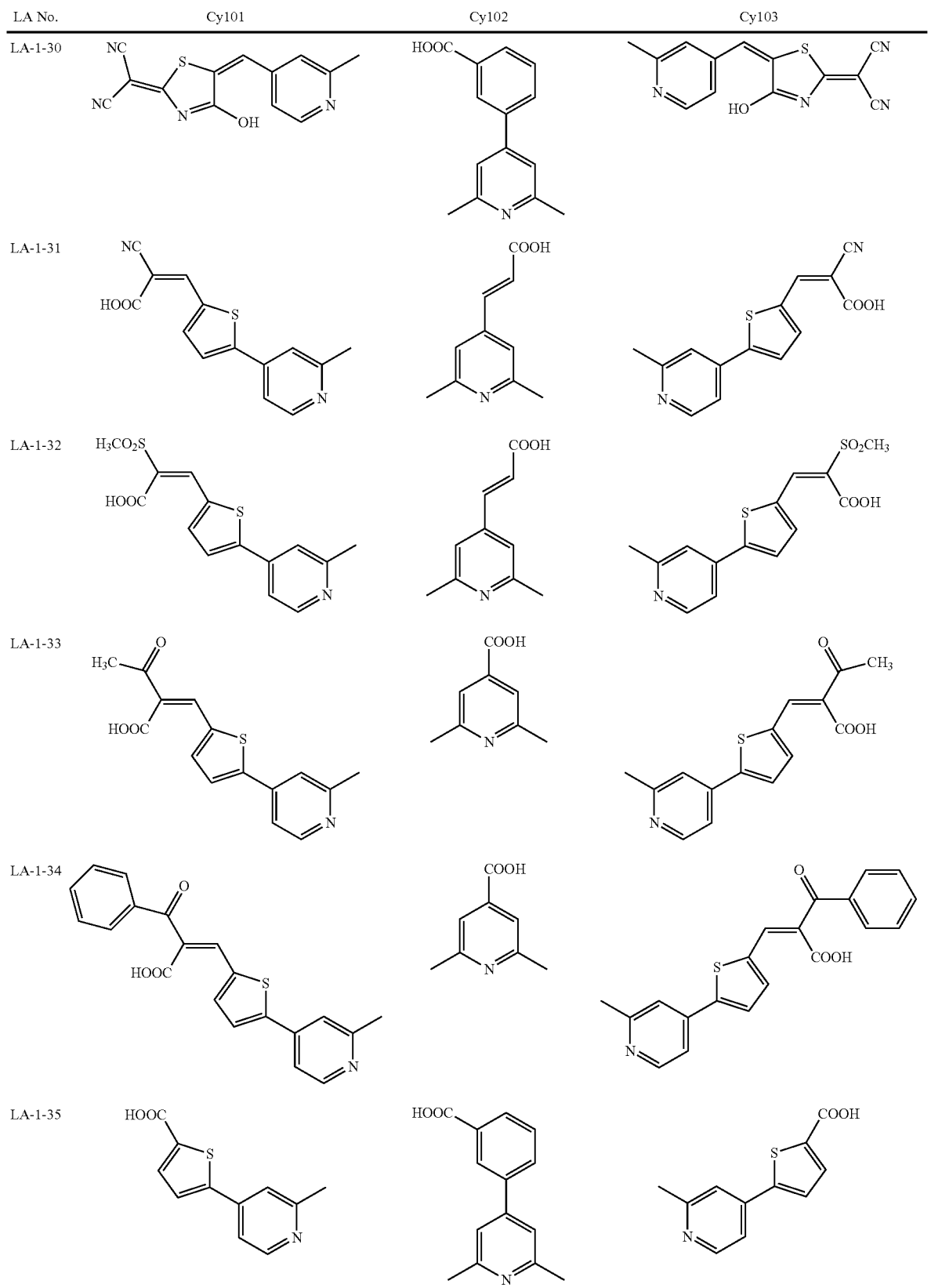

-continued

| | Cy101—Cy102—Cy103 | | |
|---|---|---|---|
| LA No. | Cy101 | Cy102 | Cy103 |
| LA-1-36 | | | |
| LA-1-37 | | | |
| LA-1-38 | | | |
| LA-1-39 | | | |
| LA-1-40 | | | |
| LA-1-41 | | | |

-continued
| LA No. | Cy101 | Cy102 | Cy103 |
|---|---|---|---|
| | | Cy101—Cy102—Cy103 | |
| LA-1-42 | 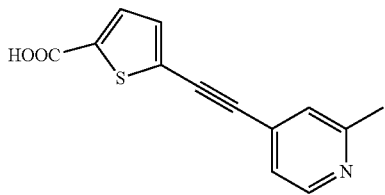 | 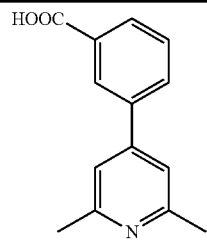 | 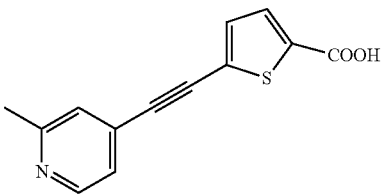 |
Series 2 of ligand LA
Ligands, in which, in any one of the three rings, $Anc^1$ to $Anc^3$ are —OH, and this —OH is a —OH linked to the following formula (AncX)
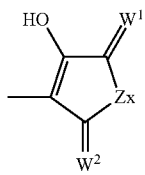
Formula (AncX)
| LA No. | Cy101 | Cy102 | Cy103 |
|---|---|---|---|
| | | Cy101—Cy102—Cy103 | |
| LA-2-1 | 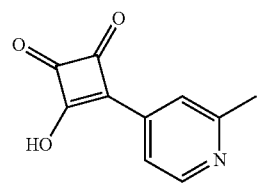 | 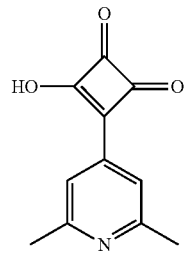 |  |
| LA-2-2 | 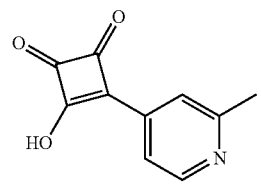 | 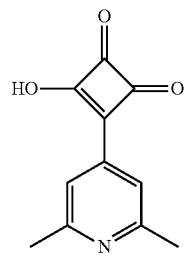 | 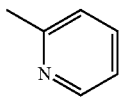 |

-continued

| LA No. | Cy101 | Cy102 | Cy103 |
|---|---|---|---|
| LA-2-3 | | | |
| LA-2-4 | | | |
| LA-2-5 | | | |
| LA-2-6 | | | |
| LA-2-7 | | | |
| LA-2-8 | | | |
| LA-2-9 | | | |

-continued

| LA No. | Cy101 | Cy102 | Cy103 |
|---|---|---|---|
| LA-2-10 | | | |
| LA-2-11 | | | |
| LA-2-12 | | | |
| LA-2-13 | | | |
| LA-2-14 | | | |
| LA-2-15 | | | |

-continued

| LA No. | Cy101 | Cy102 | Cy103 |
|---|---|---|---|
| LA-2-16 | | | |
| LA-2-17 | | | |
| LA-2-18 | | | |
| LA-2-19 | | | |
| LA-2-20 | | | |
| LA-2-21 | | | |

-continued

| LA No. | Cy101 | Cy102 | Cy103 |
|---|---|---|---|
| LA-2-22 | | | |
| LA-2-23 | | | |
| LA-2-24 | | | |
| LA-2-25 | | | |
| LA-2-26 | | | |

115

-continued

| LA No. | Cy101 | Cy102 | Cy103 |
|---|---|---|---|
| LA-2-27 | | | |
| LA-2-28 | | | |
| LA-2-29 | | | |
| LA-2-30 | | | |
| LA-2-31 | | | |
| LA-2-32 | | | |

//

-continued

| LA No. | Cy101 | Cy102 | Cy103 |
|---|---|---|---|
| LA-2-33 | | | |
| LA-2-34 | | | |
| LA-2-35 | | | |
| LA-2-36 | | | |

Cy101—Cy102—Cy103

-continued
| | Cy101—Cy102—Cy103 | | |
|---|---|---|---|
| LA No. | Cy101 | Cy102 | Cy103 |
| LA-2-37 | 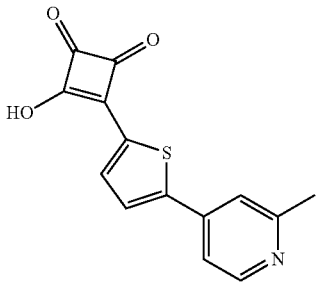 | 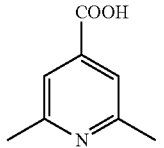 | 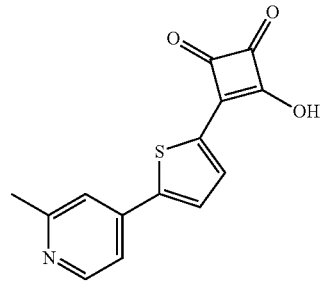 |
| LA-2-38 | 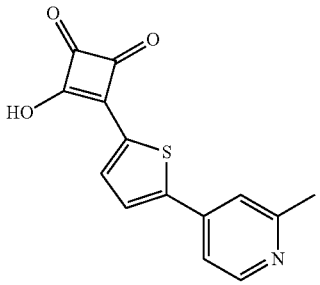 | 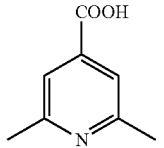 | 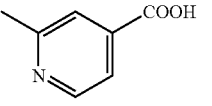 |
| LA-2-39 | 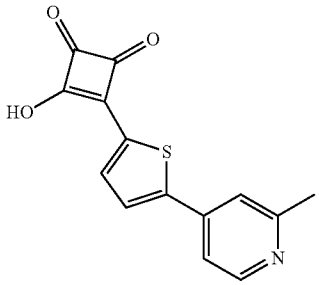 | 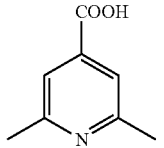 | 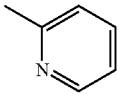 |
| LA-2-40 | 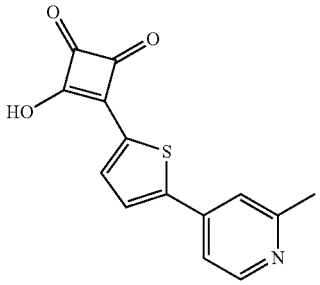 | 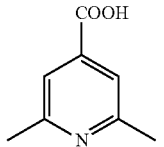 | 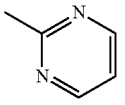 |
| LA-2-41 | 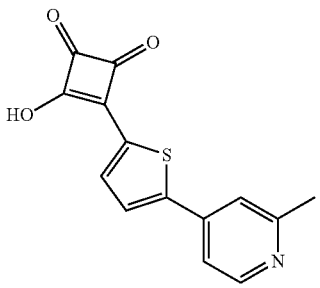 | 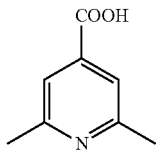 | 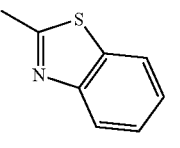 |

-continued
| LA No. | Cy101 | Cy102 | Cy103 |
|---|---|---|---|
| LA-2-42 | | | |
| LA-2-43 | | | |
| LA-2-44 | | | |
| LA-2-45 | | | |
| LA-2-46 | | | |
Cy101—Cy102—Cy103
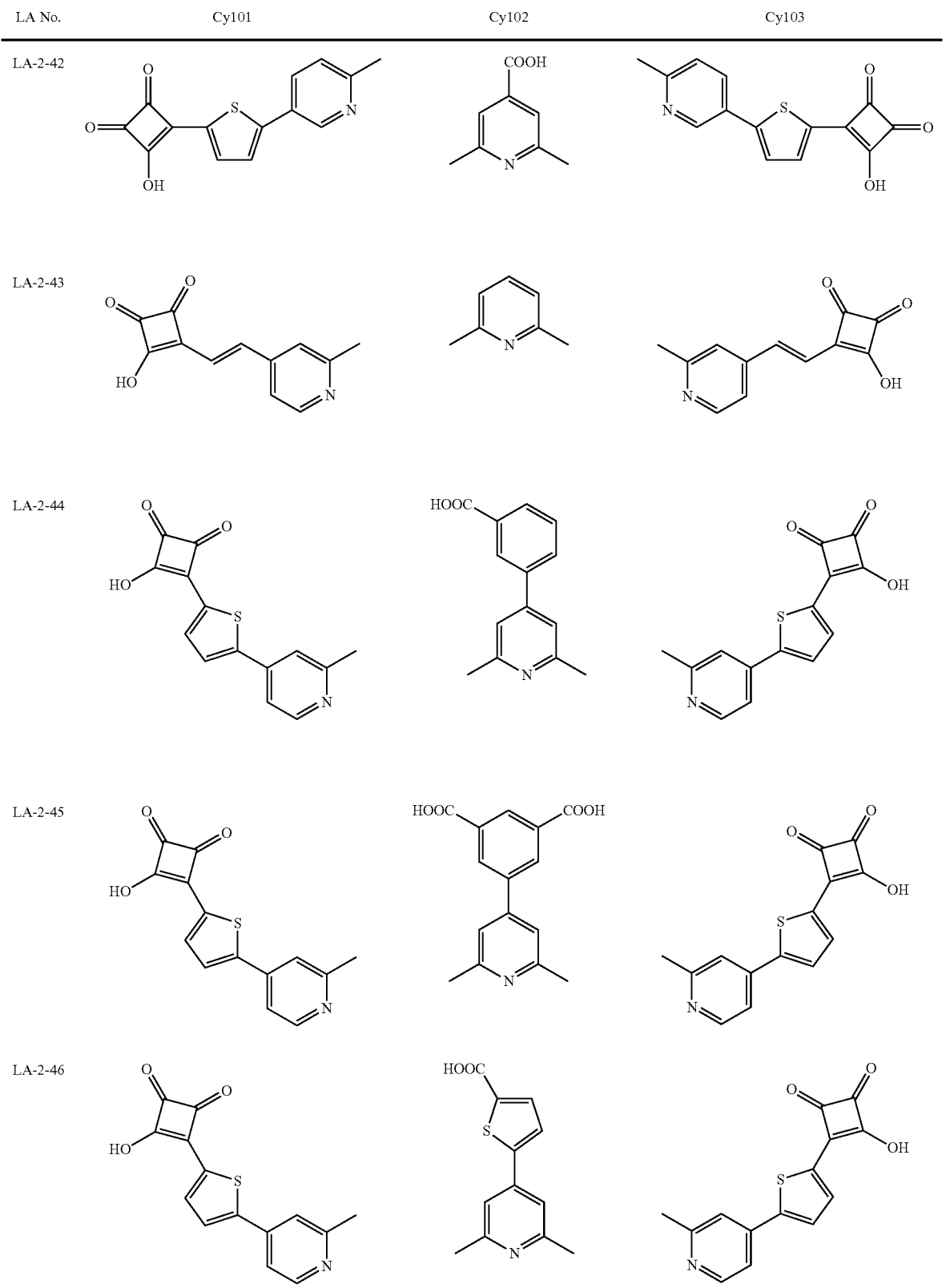

-continued

| LA No. | Cy101 | Cy102 | Cy103 |
|---|---|---|---|
| LA-2-47 | | | |
| LA-2-48 | | | |
| LA-2-49 | | | |
| LA-2-50 | | | |
| LA-2-51 | | | |

-continued

| | Cy101—Cy102—Cy103 | | |
|---|---|---|---|
| LA No. | Cy101 | Cy102 | Cy103 |
| LA-2-52 | | | |
| LA-2-53 | | | |
| LA-2-54 | | | |
| LA-2-55 | | | |
| LA-2-56 | | | |

-continued

| LA No. | Cy101 | Cy102 | Cy103 |
|---|---|---|---|
| LA-2-57 | | | |
| LA-2-58 | | | |
| LA-2-59 | | | |
| LA-2-60 | | | |
| LA-2-61 | | | |

-continued

| LA No. | Cy101 | Cy102 | Cy103 |
|---|---|---|---|
| LA-2-62 | | | |
| LA-2-63 | | | |
| LA-2-64 | | | |
| LA-2-65 | | | |
| LA-2-66 | | | |

-continued

| LA No. | Cy101 | Cy102 | Cy103 |
|---|---|---|---|
| LA-2-67 | | | |
| LA-2-68 | | | |
| LA-2-69 | | | |
| LA-2-70 | | | |
| LA-2-71 | | | |
| LA-3-1 | | | |

-continued

| | Cy101—Cy102—Cy103 | | |
|---|---|---|---|
| LA No. | Cy101 | Cy102 | Cy103 |
| LA-3-2 | | | |
| LA-3-3 | | | |
| LA-4-1 | | | |
| LA-4-2 | | | |
| LA-4-3 | | | |

-continued

| | Cy101—Cy102—Cy103 | | |
|---|---|---|---|
| LA No. | Cy101 | Cy102 | Cy103 |
| LA-5-1 | | | |
| LA-5-2 | | | |
| LA-5-3 | | | |
| LA-6-1 | | | |
| LA-6-2 | | | |

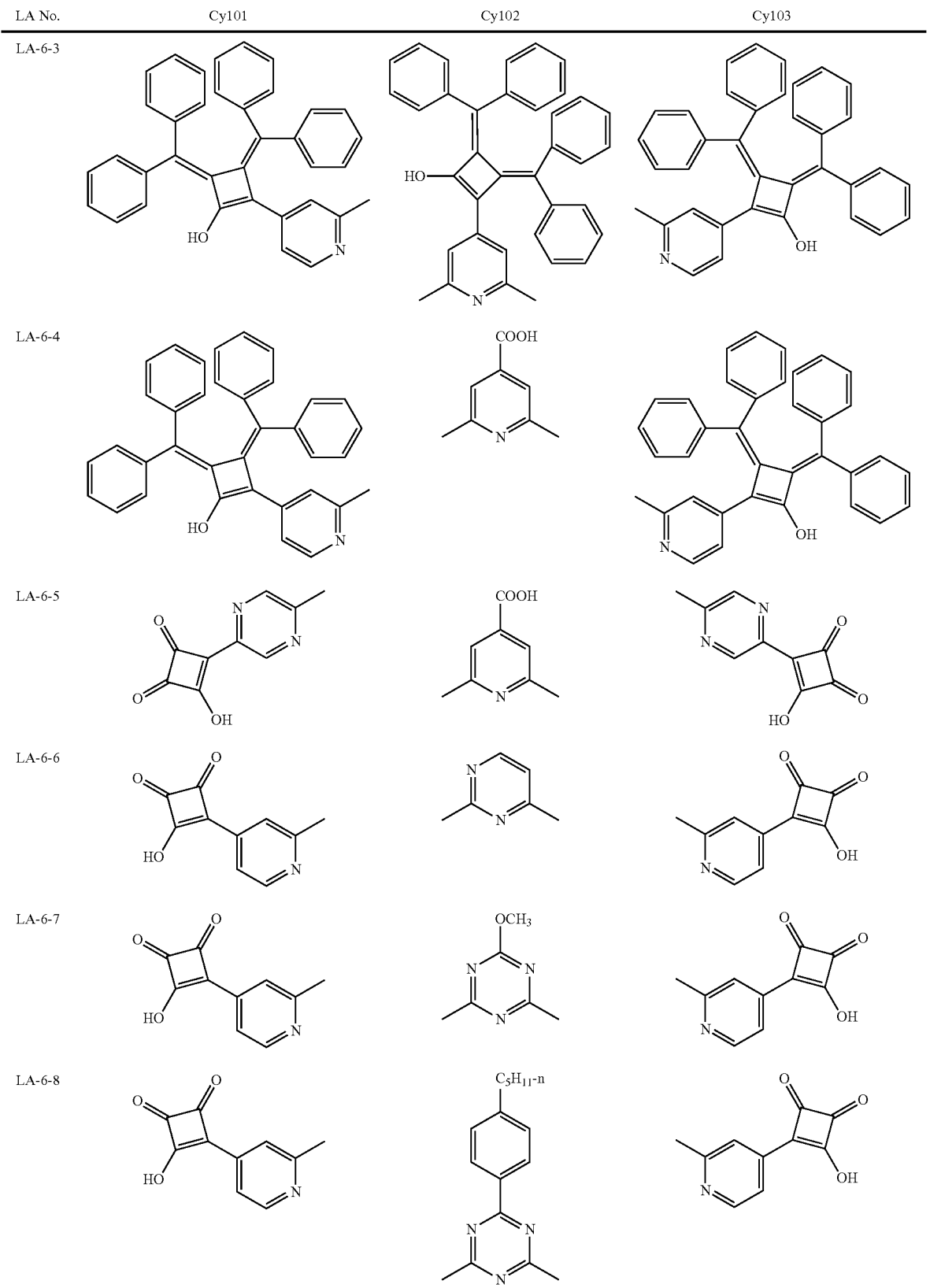

-continued

| LA No. | Cy101 | Cy102 | Cy103 |
|---|---|---|---|
| LA-6-9 | | | |
| LA-6-10 | | | |
| LA-7-1 | | | |
| LA-7-2 | | | |
| LA-7-3 | | | |
| LA-7-4 | | | |

-continued

| LA No. | Cy101 | Cy102 | Cy103 |
|---|---|---|---|
| LA-7-5 | | | |
| LA-7-6 | | | |
| LA-7-7 | | | |
| LA-7-8 | | | |
| LA-7-9 | | | |
| LA-7-10 | | | |

The ligand LA may be synthesized by a metal halogen exchange reaction, a cross coupling reaction, a Knoevenagel condensation reaction, and the like.

—Counter Ion CI for Neutralizing an Electric Charge—

CI represents a counter ion in the case where the counter ion is necessary to neutralize an electric charge. Generally, whether a dye is cationic or anionic, or has a net ionic charge, depends on the metal, the ligand and the substituent, in the metal complex dye.

In the case where the substituent has a dissociative group or the like, the metal complex dye may have a negative charge arising from dissociation. In this case, an electric charge of the metal complex dye as a whole is electrically neutralized by CI.

When the counter ion CI is a positive counter ion, examples of the counter ion CI include an inorganic or organic ammonium ion (for example, tetraalkyl ammonium ion such as tetrabutylammonium ion; triethyl benzyl ammonium ion, pyridinium ion, and the like), a phosphonium ion (for example, tetraalkyl phosphonium ion such as tetrabutyl phosphonium ion, alkyltriphenyl phosphonium ion, triethyl phenyl phosphonium ion, and the like), an alkali metal ion, a metal complex ion and a proton. As a positive counter ion, an inorganic or organic ammonium ion (for example, triethylammonium ion, tetrabutylammonium ion, and the like), or a proton is preferable.

When the counter ion CI is a positive counter ion, examples of the counter ion CI include an inorganic or organic ammonium ion (for example, tetraalkyl ammonium ion, pyridinium ion, and the like), a phosphonium ion (for example, a tetralkylphosphonium ion, an alkyltriphenylphosphonium ion, and the like), an alkali metal ion, metal complex ion and a proton. As a positive counter ion, an inorganic or organic ammonium ion (triethylammonium ion, tetrabutyl ammonium ion, and the like), or a proton is preferable.

When the counter ion CI is a negative counter ion, the counter ion CI may be an inorganic negative ion or an organic negative ion. Examples thereof include a hydroxide ion, a halogen negative ion (for example, fluoride ion, chloride ion, bromide ion, iodide ion), a substituted or unsubstituted alkylcarboxylate ion (for example, acetate ion, trifluoroacetate ion), a substituted or unsubstituted arylcarboxylate ion (for example, benzoate ion), a substituted or unsubstituted alkylsulfonate ion (for example, methanesulfonate ion, trifluoromethanesulfonate ion), a substituted or unsubstituted arylsulfonate ion (for example, p-toluene sulfonate ion, p-chlorobenzene sulfonate ion), an aryldisulfonate ion (for example, 1,3-benzene disulfonate ion, 1,5-naphthalene disulfonate ion, 2,6-naphthalene disulfonate ion), an alkylsulfate ion (for example, methylsulfate ion), a sulfate ion, a thiocyanate ion, a perchlorate ion, a tetrafluoroborate ion, a hexafluorophosphae ion, and a picrate ion. Alternatively, as a charge balance counter ion, an ionic polymer or another dye with an opposite charge from the dye in interest may be used. Alternatively, a metal complex ion (for example, bis(benzene-1,2-dithiolato)nickel (III) and the like) may be used. As the negative counter ion, a halogen anion, a substituted or unsubstituted alkylcarboxylate ion, a substituted or unsubstituted alkylsulfonate ion, a substituted or unsubstituted arylsulfonate ion, an aryldisulfonate ion, a perchlorate ion, and a hexafluorophosphate ion are preferred; and a halogen anion and a hexafluorophosphate ion are more preferred.

—Metal Complex Dye of the Present Invention—

In the following, specific examples of the metal complex dye represented by Formula (I) are shown, but the present invention is not limited thereto.

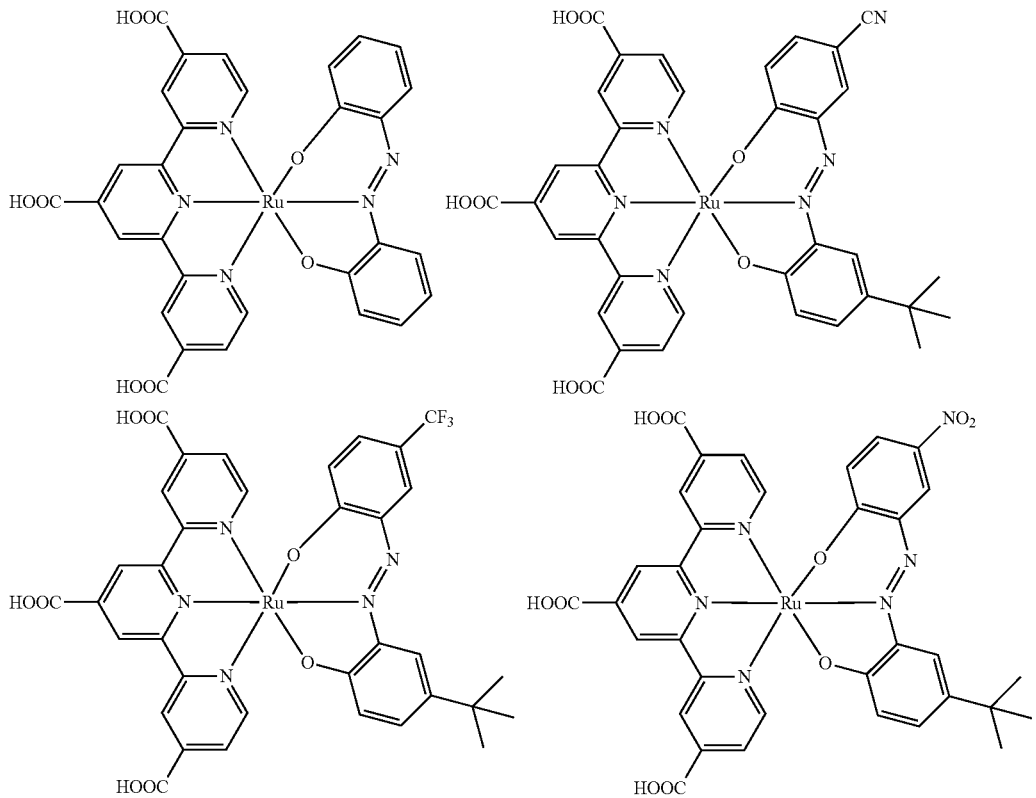

145 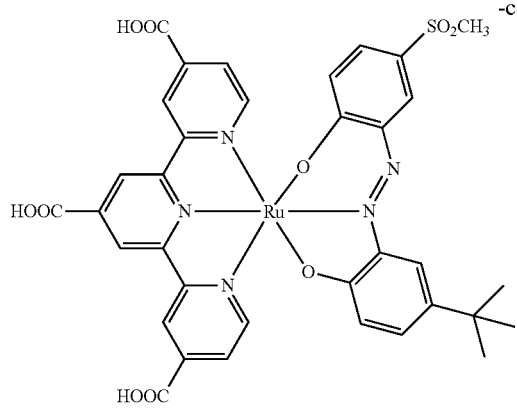 146 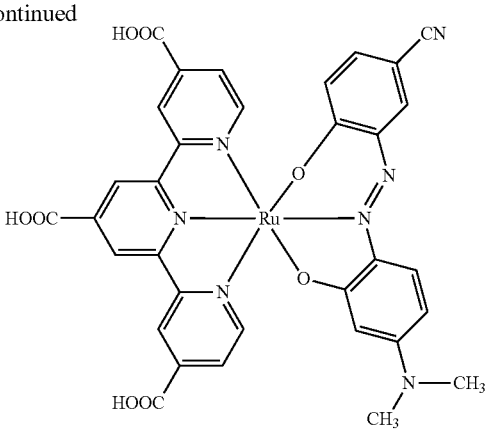
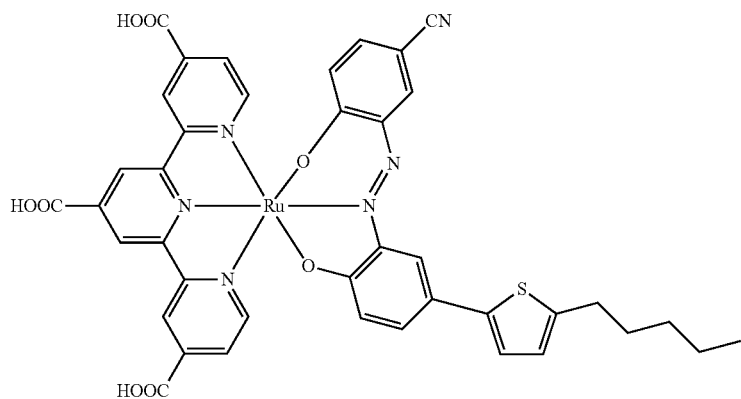
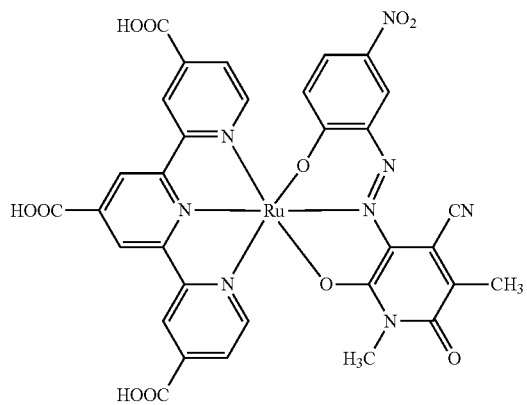 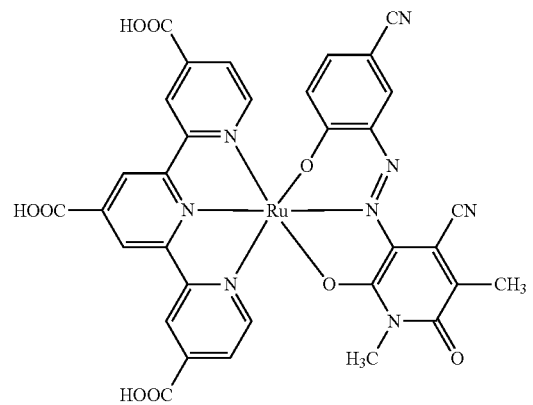
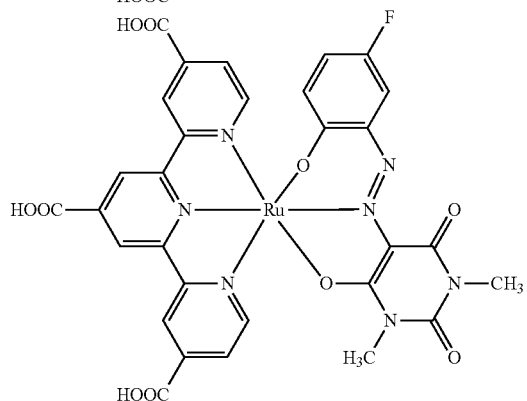 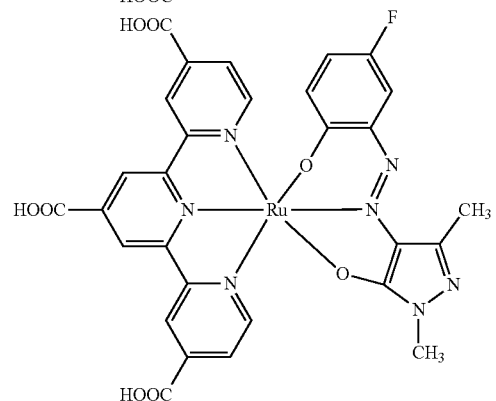

147
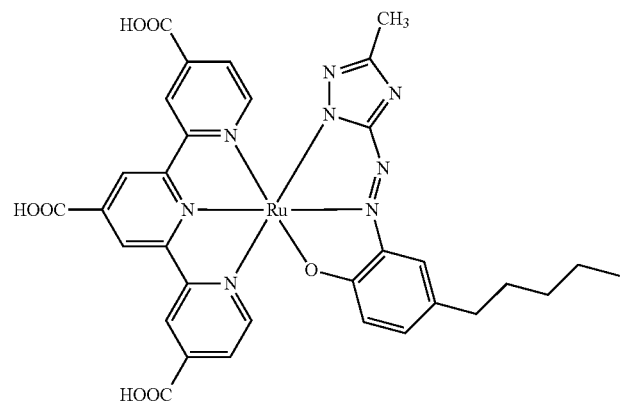
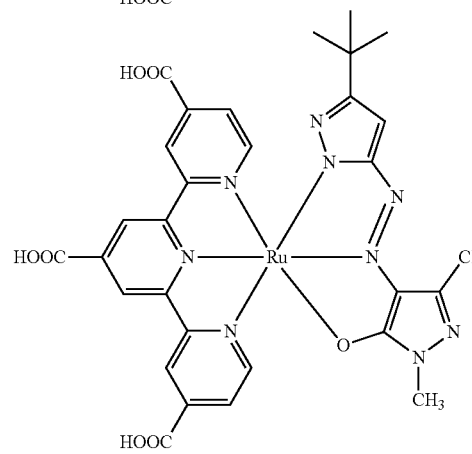
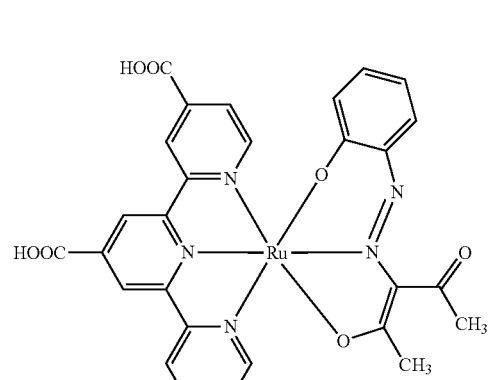
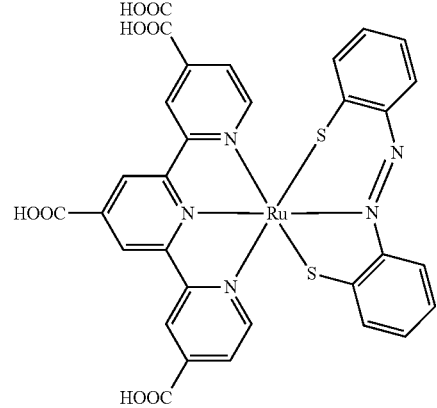
148
-continued
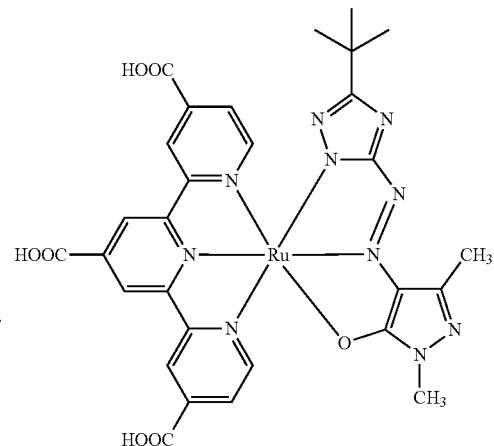
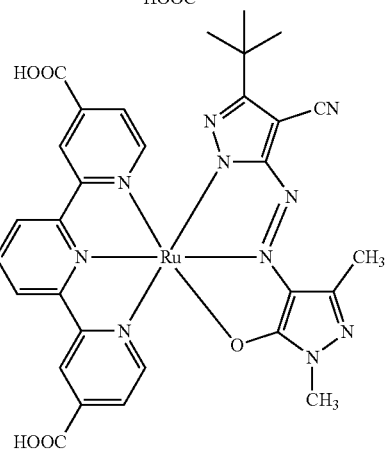
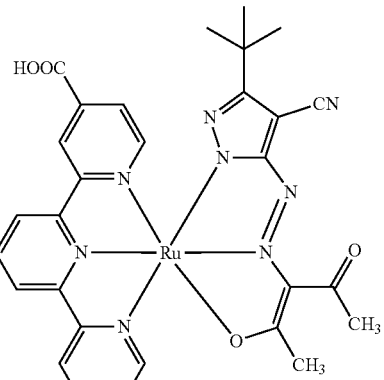
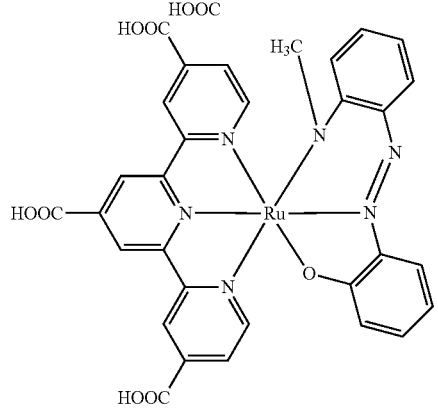

149
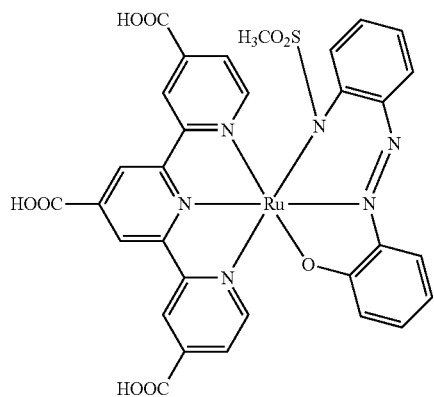
150
-continued
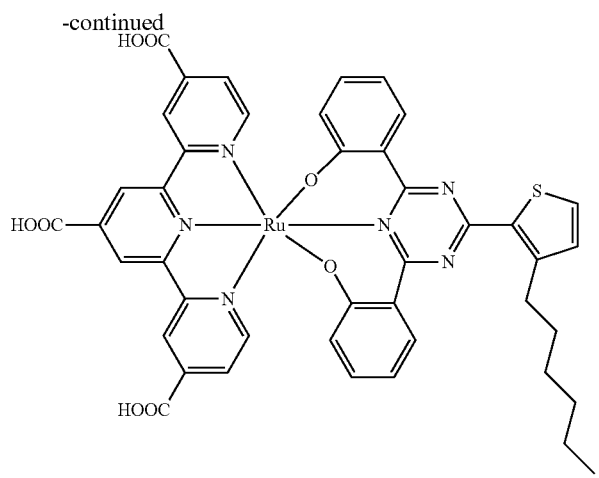
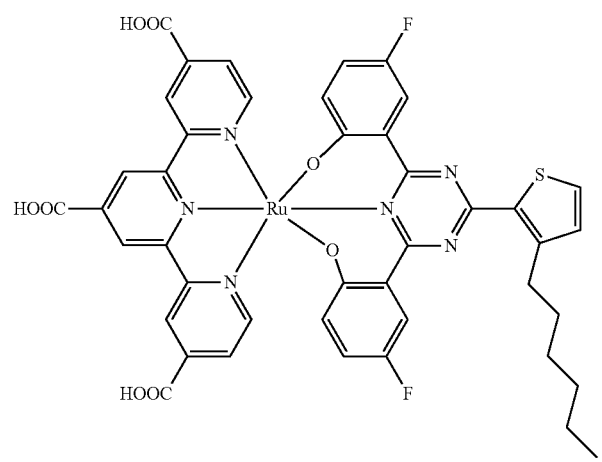
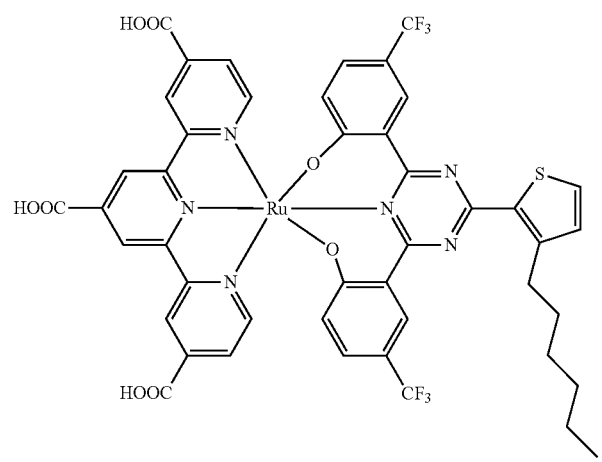

151
-continued
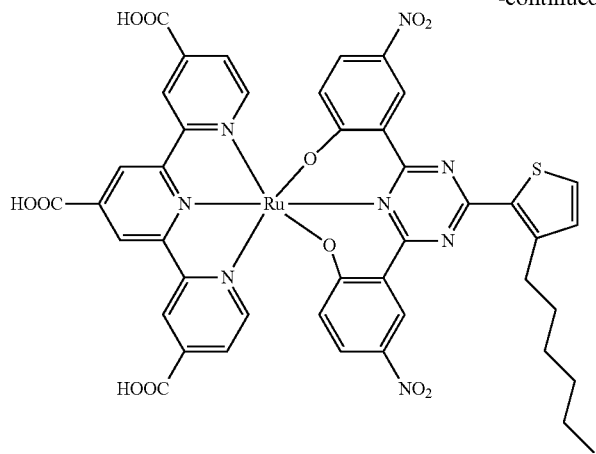
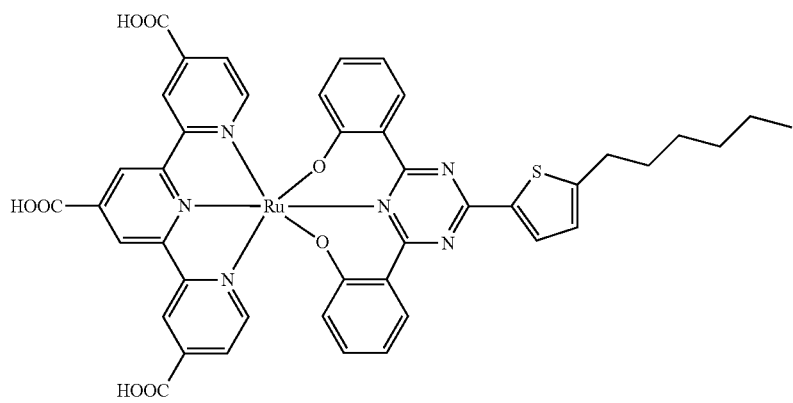
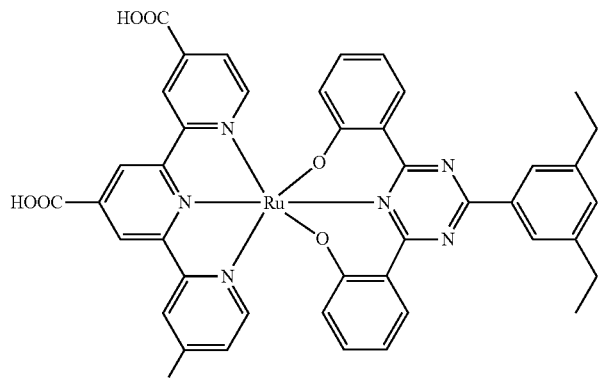
152
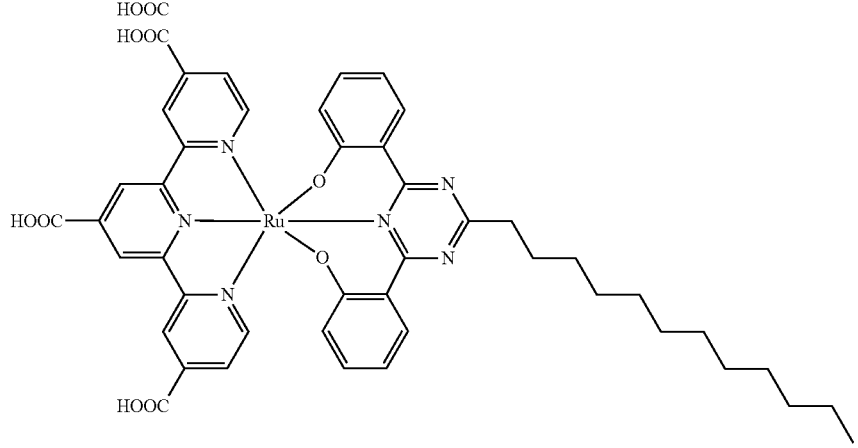

-continued
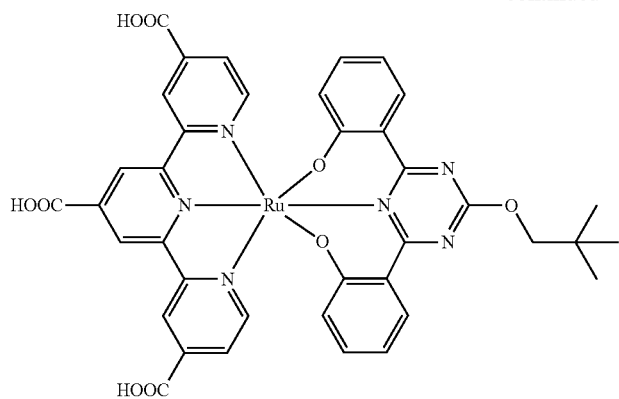
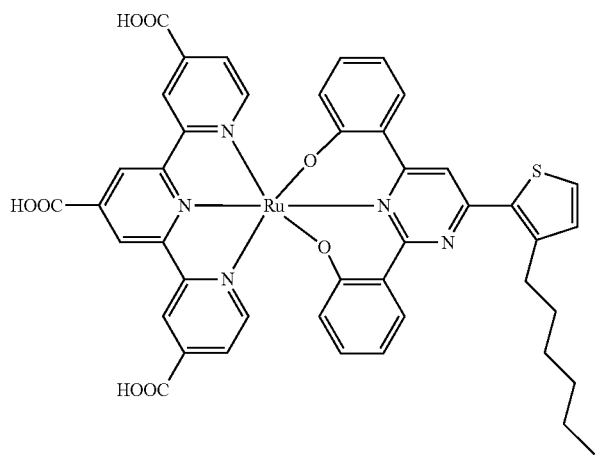
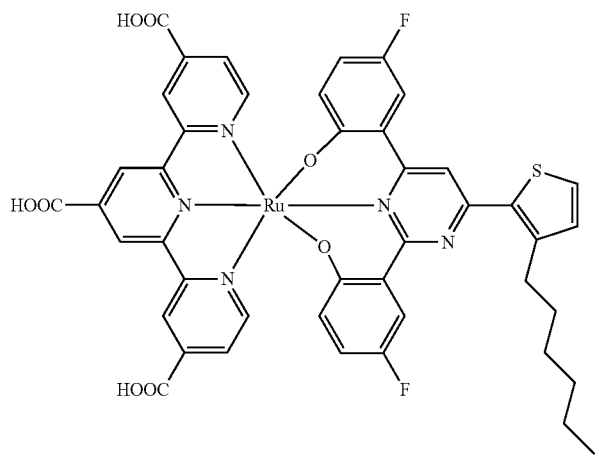

155
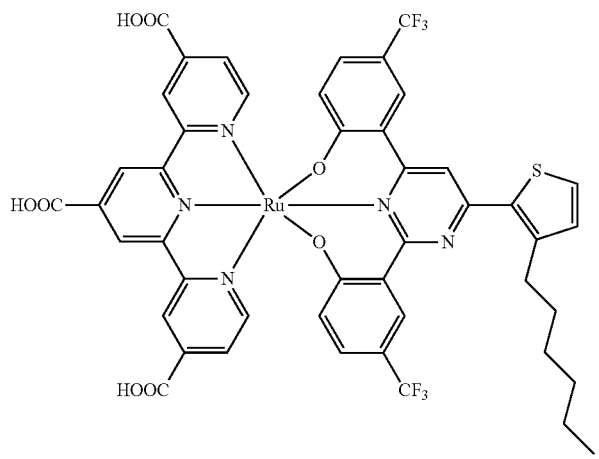
156
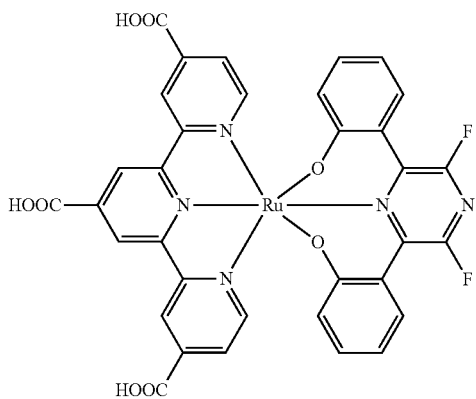
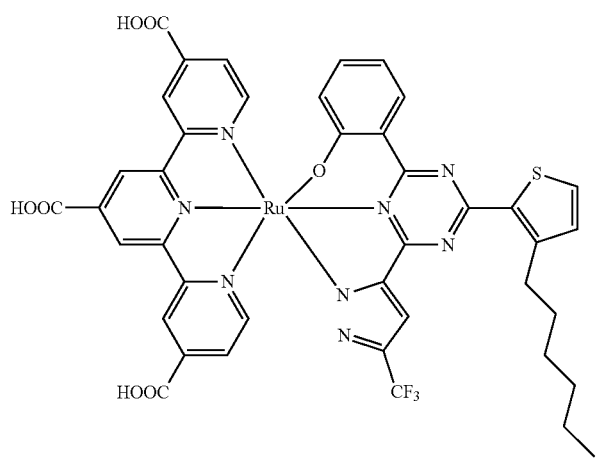
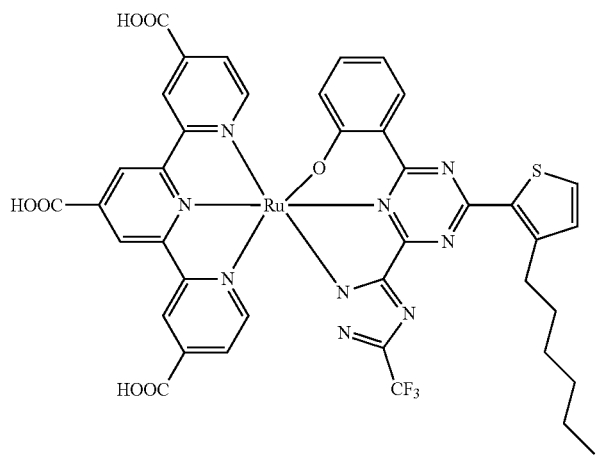

157
-continued
158
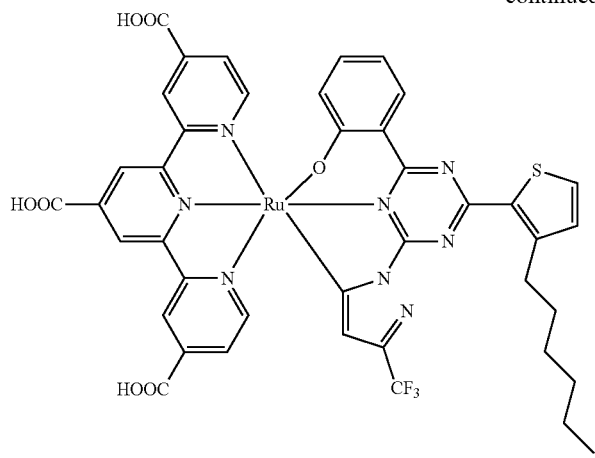
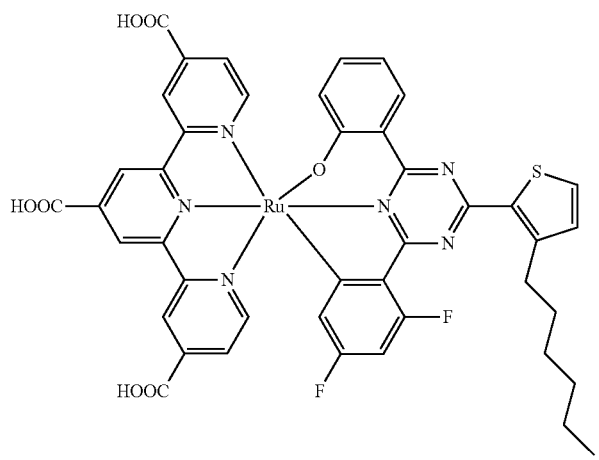
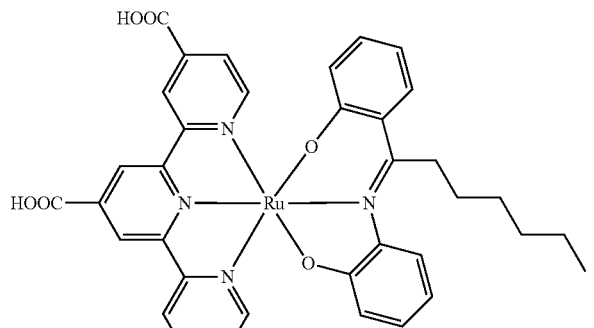
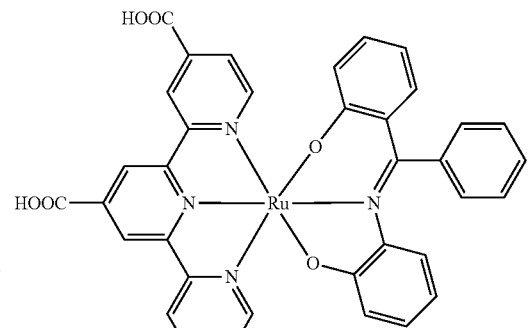
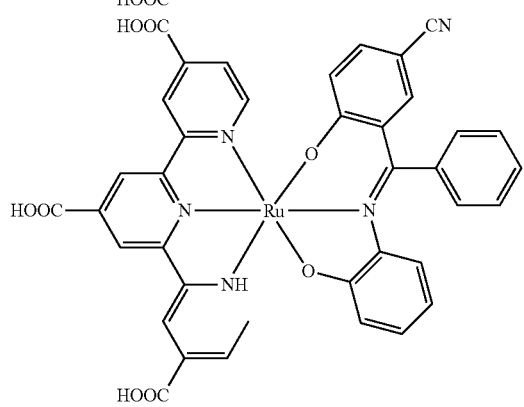
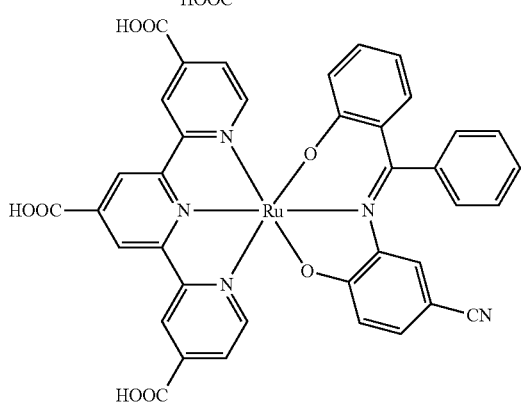

The metal complex dye represented by Formula (I) of the present invention can be synthesized referring to the method described in any one of Chemistry—A European Journal, 17(39), 10871 to 10878 (2011); Angewandte Chemie, 84, 824 to 826 (1972), Dalton Transactions, 5, 770 to 772 (2009), and JP-A-2001-291534 or a method according to the method cited in JP-A-2001-291534, and a method according to the method described in Angew. Chem. Int. Ed., 50, 2054 to 2058 (2011).

The metal complex dye of present invention has a maximum absorption wavelength in a solution in a range of preferably from 300 to 1,000 nm, more preferably from 350 to 950 nm, and especially preferably from 370 to 900 nm.

In addition, the metal complex dye of the present invention also has an absorption range even in 900 to 1000 nm.

In the present invention, the metal complex dye of the present invention and another dye may be used in combination.

The dye to be used in combination includes: a Ru complex dye described in JP-T-7-500630 (in particular, dyes synthesized in Examples 1 to 19 described in from line 5 on left lower column on page 5 to line 7 on right upper column on page 7) (the term "JP-T" means a published Japanese translation of a PCT patent application), a Ru complex dye described in JP-T-2002-512729 (in particular, dyes synthesized in Examples 1 to 16 described in line 3 from the bottom of page 20 to line 23 on page 29), a Ru complex dye described in JP-A-2001-59062 (in particular, dyes described in paragraph Nos. 0087 to 0104), a Ru complex dye described in JP-A-2001-6760 (in particular, dyes described in paragraph Nos. 0093 to 0102), a Ru complex dye described in JP-A-2001-253894 (in particular, dyes described in paragraph Nos. 0009 to 0010), a Ru complex dye described in JP-A-2003-212851 (in particular, dyes described in paragraph No. 0005), a Ru complex dye described in WO 2007/91525 pamphlet (in particular, dyes described in paragraph No. [0067]), a Ru complex dye described in JP-A-2001-291534 (in particular, dyes described in paragraph Nos. 0120 to 0144), a Ru complex dye described in JP-A-2012-012570 (in particular, dyes described in paragraph Nos. 0095 to 0103), a squarylium cyanine dye described in JP-A-11-214730 (in particular, dyes described in paragraph Nos. 0036 to 0047), a squarylium cyanine dye described in JP-A-2012-144688 (in particular, dyes described in paragraph Nos. 0039 to 0046 and 0054 to 0060), a squarylium cyanine dye described in JP-A-2012-84503 (in particular, dyes described in paragraph Nos. 0066 to 0076 and the like), an organic dye described in JP-A-2004-063274 (in particular, dyes described in paragraph Nos. 0017 to 0021), an organic dye described in JP-A-2005-123033 (in particular, dyes described in paragraph Nos. 0021 to 0028), an organic dye described in JP-A-2007-287694 (in particular, dyes described in paragraph Nos. 0091 to 0096), an organic dye described in JP-A-2008-71648 (in particular, dyes described in paragraph Nos. 0030 to 0034), an organic dye described in WO 2007/119525 pamphlet (in particular, dyes described in paragraph No. [0024]), a porphyrine dye described in Angew. Chem. Int. Ed., 49, 1 to 5 (2010), and a phthalocyanine dye described in Angew. Chem. Int. Ed., 46, 8358 (2007), or the like.

Preferable dyes to be used in combination include Ru complex dyes, squaryrium cyanine dyes, or organic dyes.

In the case where the metal complex dye of the present invention and another dye are used in combination, a ratio of mass of the metal complex dye of the present invention/mass of another dye is preferably from 95/5 to 10/90, more preferably from 95/5 to 50/50, still more preferably from 95/5 to 60/40, particularly preferably from 95/5 to 65/35, and most preferably from 95/5 to 70/30.

—Electrically-Conductive Support—

The electrically-conductive support is preferably a support having electroconductivity by itself, such as a metal, or a glass or plastic support having an electrically-conductive film layer on the surface. As the plastic support, a transparent polymer film described in paragraph No. 0153 of JP-A-2001-291534 can be mentioned. As the support, in addition to the glass and plastic, ceramic (JP-A-2005-135902), an electrically-conductive resin (JP-A-2001-160425), or the like may be used. The electrically-conductive support may be provided with a light management function at the surface, and for example, the anti-reflective film in which a high refractive index film and a low refractive index oxide film are alternately laminated, as described in JP-A-2003-123859, and the light guide function as described in JP-A-2002-260746 may be mentioned.

The thickness of the electrically-conductive layer is preferably 0.01 to 30 µm, more preferably 0.03 to 25 µm, and particularly preferably 0.05 to 20 µm.

It is preferable that the electrically-conductive support is substantially transparent. The term "substantially transparent" means that the transmittance of light is 10% or more, preferably 50% or more, and particularly preferably 80% or more. As the transparent electrically-conductive support, a support formed from glass or plastic and coated with an electrically-conductive metal oxide is preferable. As the metal oxide, tin oxide is preferable, and indium-tin oxide and fluorine-doped oxide are particularly preferable. In this case, the coating amount of the electrically-conductive metal oxide is preferably 0.1 to 100 g, per square meter of the support made of glass or plastic. In the case of using a transparent electrically-conductive support, it is preferable that light is incident from the support side.

—Semiconductor Fine-Particles—

Regarding the semiconductor fine-particles, fine-particles of chalcogenides of metals (for example, oxides, sulfides and selenides), or fine-particles of perovskites may be used with preference. Preferred examples of the chalcogenides of metals include oxides of titanium, tin, zinc, tungsten, zirconium, hafnium, strontium, indium, cerium, yttrium, lanthanum, vanadium, niobium or tantalum, cadmium sulfide, and cadmium selenide. Preferred examples of the perovskites include strontium titanate, and calcium titanate. Among these, titanium oxide (titania), zinc oxide, tin oxide, and tungsten oxide are particularly preferred.

Examples of the crystal structure of titania include structures of anatase type, brookite type and rutile type, and anatase type and brookite type structures are preferred. A titania nanotube, nanowire, or nanorod may be mixed with titania fine-particles or may be used as a semiconductor electrode.

A particle size of the semiconductor fine-particles is expressed in terms of an average particle size using a diameter when a projected area is converted into a circle, and is preferably 0.001 to 1 µm as primary particles, and 0.01 to 100 µm as an average particle size of dispersions. Examples of the method for coating the semiconductor fine-particles on the electrically-conductive support include a wet method, a dry method or other methods.

It is preferable to form a short circuit-preventing layer between the transparent electrically-conductive film and the photoconductor layer ("semiconductor layer"), so as to prevent reverse current due to a direct contact between the electrolyte liquid and the electrode. It is preferable to employ a spacer or a separator, so as to prevent contact between the photoelectrode and the counter electrode. It is preferable for the semiconductor fine-particles to have a large surface area, so that a large amount of dye can adsorb to the surface. For example, in a state of the semiconductor fine-particles being coated on the support, the surface area is preferably 10 times or more, and more preferably 100 times or more, relative to the projected surface area. The upper limit of this value is not particularly limited, and the upper limit is generally about 5,000 times. In general, as the thickness of the layer containing semiconductor fine particles increases, the amount of dye that can be carried per unit area increases, and therefore, the light absorption efficiency is increased. However, since the diffusion distance of generated electrons increases along, the loss due to charge recombination is also increased. Although a preferred thickness of the photoconductor layer being a semiconductor layer may vary with the utility of the element, the thickness is typically 0.1 to 100 µm. In the case of using the photoelectric conversion element for a dye-sensitized solar cell, the thickness of the semiconductor fine-particle layer is preferably 1 to 50 µm, and more preferably 3 to 30 µm. The semiconductor fine-particles may be calcined after being applied on the support, at a temperature of 100 to 800° C. for 10 minutes to 10 hours, so as to bring about cohesion of the particles. When a glass support is used, the film-forming temperature is preferably 400 to 600° C.

The amount of coating of the semiconductor fine-particles per square meter of the support is preferably 0.5 to 500 g, and more preferably 5 to 100 g. The overall amount of use of the dye is preferably 0.01 to 100 millimoles, more preferably 0.1 to 50 millimoles, and particularly preferably 0.1 to 10 millimoles, per square meter of the support. In this case, the amount of use of the metal complex dye of the present invention is preferably set to 5% by mole or more. The amount of the dye adsorbed to the semiconductor fine-particles is preferably 0.001 to 1 millimole, and more preferably 0.1 to 0.5 millimoles, based on 1 g of the semiconductor fine-particles. When the amount of the dye is set to such a range, the sensitization effect in the semiconductor fine particles can be sufficiently obtained.

When the above dye is a salt, a counter ion of the above specific metal complex dye is not particularly limited. Examples thereof include an alkali metal ion and a quaternary ammonium ion.

After the dye has been adsorbed, the surface of the semiconductor fine-particles may be treated using amines. Preferred examples of the amines include pyridines (e.g., 4-tert-butylpyridine, and polyvinylpyridine). These may be used directly when the compounds are liquids, or may be used in a state of being dissolved in an organic solvent.

In the photoelectric conversion element (for example, a photoelectric conversion element 10) and the dye-sensitized solar cell (for example, dye-sensitized solar cell 20) according to the present invention, at least the metal complex dye of the present invention is used.

—Charge-Transfer Layer—

The charge transfer layer for use in the photoelectric conversion element of the present invention is a layer having a function to replenish electrons to the oxidized form of the dye, and it is provided between the light-receiving electrode and the counter electrode (an opposite electrode). The charge-transfer layer contains an electrolyte.

Examples of the electrolyte include a liquid electrolyte having a redox pair dissolved in an organic solvent, a so-called gel electrolyte in which a liquid having a redox pair dissolved in an organic solvent is impregnated in a polymer matrix, and a molten salt containing a redox pair. In order to enhance photoelectric conversion efficiency, a liquid electrolyte is preferred. As a solvent of the liquid electrolyte, a nitrile compound, an ether compound, an ester compound, or the like, is used, and a nitrile compound is preferred, and acetonitrile and methoxypropionitrile are particularly preferred.

Examples of the redox pair include a combination of iodine and an iodide (preferably an iodide salt, or an iodide ionic liquid; more preferably lithium iodide, tetrabutylammonium iodide, tetrapropylammonium iodide, or methylpropylimidazolium iodide), a combination of an alkylviologen (for example, methylviologen chloride, hexylviologen bromide, or benzylviologen tetrafluoroborate) and a reductant thereof, a combination of a polyhydroxybenzene (for example, hydroquinone, naphthohydroquinone, or the like) and an oxidized form thereof, a combination of a divalent iron complex and a trivalent iron complex (for example, a combination of potassium ferricyanide and potassium ferrocyanide), and a combination of a divalent cobalt complex and a trivalent cobalt complex. Among these, a combination of iodine and an iodide, and a combination of a divalent cobalt complex and a trivalent cobalt complex, are preferred.

The cobalt complex is preferably a complex represented by the following formula (CC).

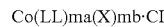

formula (CC)

In formula (CC), LL represents a bidentate or tridentate ligand. X represents a monodentate ligand. ma represents an integer of 0 to 3. mb represents an integer of 0 to 6. CI represents a counter ion in the case where the counter ion is necessary to neutralize an electric charge.

Examples of CI include those of CI in formula (I).

LL is preferably a ligand represented by the following formula (LC).

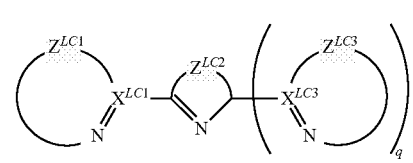

Formula (LC)

In formula (LC), $Z^{LC1}$, $Z^{LC2}$ and $Z^{LC3}$ each independently represent a group of nonmetallic atoms necessary to form a 5- or 6-membered ring. Each of $Z^{LC1}$, $Z^{LC2}$ and $Z^{LC3}$ may have a substituent, and may form a ring-closure together with an adjacent ring through a substituent. $X^{LC1}$ and $X^{LC3}$ represent a carbon atom or a nitrogen atom. q represents 0 or 1. Examples of the substituent include the substituent T described later.

X is preferably a halogen ion.

The ligand represented by formula (LC) is preferably a ligand represented by any one of the following formulas (LC-1) to (LC-4).

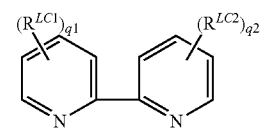

Formula (LC-1)

-continued

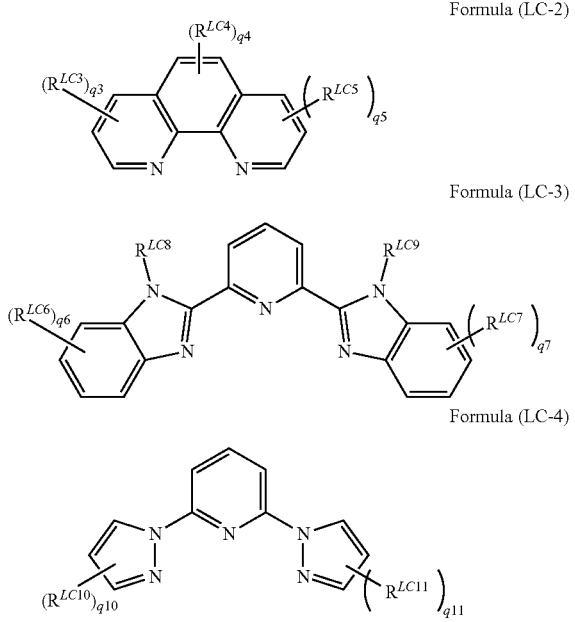

Formula (LC-2)

Formula (LC-3)

Formula (LC-4)

$R^{LC1}$ to $R^{LC11}$ each independently represent a substituent. q1, q2, q6, and q7 each independently represent an integer of 0 to 4. q3, q5, q10, and q11 each independently represent an integer of 0 to 3. q4 represents an integer of 0 to 2.

In formulas (LC-1) to (LC-4), examples of the substituent $R^{LC1}$ to $R^{LC11}$ include an aliphatic group, an aromatic group, a heterocyclic group or the like. Specific examples of the substituent include an alkyl group, an alkoxy group, an alkylthio group, an aryl group, an aryloxy group, an arylthio group, and a heterocycle. Preferred examples include an alkyl group (for example, methyl, ethyl, n-butyl, n-hexyl, isobutyl, sec-butyl, t-butyl, n-dodecyl, cyclohexyl, or benzyl), an aryl group (for example, phenyl, tolyl, or naphthyl), an alkoxy group (for example, methoxy, ethoxy, isopropoxy, or butoxy), an alkylthio group (for example, methylthio, n-butylthio, n-hexylthio, or 2-ethylhexylthio), an aryloxy group (for example, phenoxy, or naphthoxy), an arylthio group (for example, phenylthio, or naphthylthio), and a heterocyclic group (for example, 2-thienyl, or 2-furyl).

Specific examples of the cobalt complex represented by formula (LC) include the following complexes.

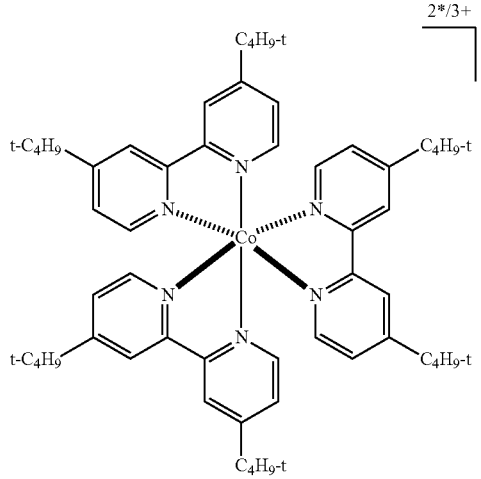

LL-1

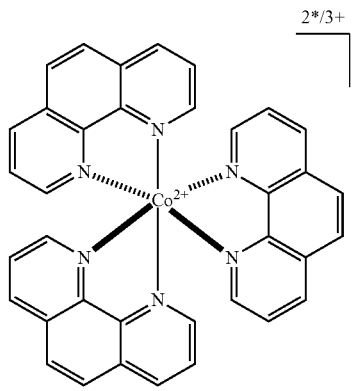

LL-2

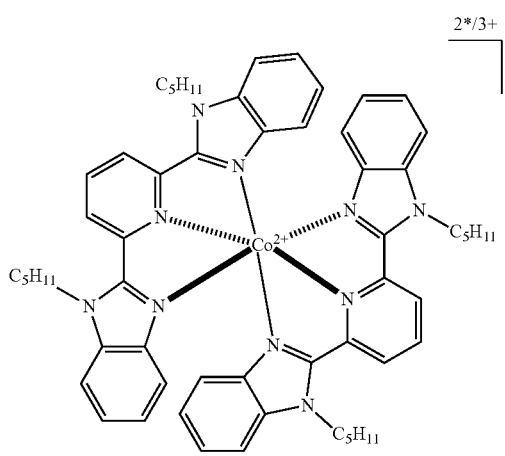

LL-3

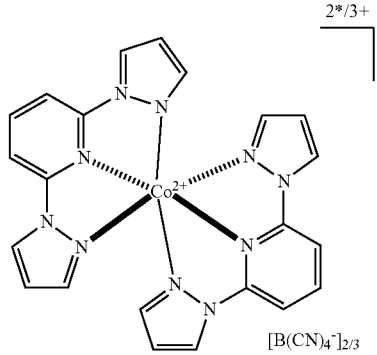

LL-4

In the case where iodine and an iodide are used in combination, as an electrolyte, it is preferred that a 5- or 6-membered-ring nitrogen-containing aromatic cation iodide salt is additionally used in combination with them.

Preferred examples of the organic solvent that dissolves these redox pairs include aprotic polar solvents (for example, acetonitrile, propylene carbonate, ethylene carbonate, dimethylformamide, dimethylsulfoxide, sulfolane, 1,3-dimethylimidazolinone, and 3-methyloxazolidinone). Examples of the polymer used for a matrix of a gel electrolyte include polyacrylonitrile, polyvinylidene fluoride, and the like. Examples of the molten salts include, for example, a molten salt to which fluidity at room temperature has been imparted by mixing lithium iodide and at least one kind of other lithium salt (for example, lithium acetate or lithium perchlorate) with polyethylene oxide. The amount of addition of the polymer in this case is 1 to 50% by mass. Furthermore, the electrolyte liquid may contain y-butyrolactone, and this increases the diffusion efficiency of iodide ions, and thereby the conversion efficiency is enhanced.

Examples of the additives to the electrolyte include 4-tert-butylpyridine mentioned above, as well as aminopyridine-based compounds, benzimidazole-based compounds, aminotriazole-based compounds, aminothiazole-based compounds, imidazole-based compounds, aminotriazine-based compounds, urea derivatives, amide compounds, pyrimidine-based compounds, and heterocycles that do not contain nitrogen.

It is also preferable to employ a method of controlling the water content of the electrolyte liquid, in order to enhance the photoelectric conversion efficiency. Preferred examples of the method of controlling the water content include a method of controlling the concentration, and a method of adding a dehydrating agent. In order to reduce the toxicity of iodine, a clathrate compound of iodine with cyclodextrin may be used. Alternatively, a method of supplying moisture on a steady basis may be used. Furthermore, a cyclic amidine may be used; or an oxidation inhibitor, a hydrolysis inhibitor, a decomposition inhibitor or zinc iodide may be added.

A molten salt may also be used as the electrolyte, and preferred examples of the molten salt include an ionic liquid containing an imidazolium or triazolium type cation, an oxazolium-based salt, a pyridinium-based salt, a guanidium-based salt, and combinations of these. These cations may be used in combination with particular anions. Additives may be added to these molten salts. The molten salt may have a substituent having liquid crystalline properties. Furthermore, the quaternary ammonium salt-based molten salt may also be used.

Molten salts other than those described above include, for example, a molten salt to which fluidity at room temperature has been imparted by mixing lithium iodide and at least one kind of other lithium salt (for example, lithium acetate or lithium perchlorate) with polyethylene oxide.

The electrolyte may be quasi-solidified by adding a gelling agent to an electrolyte liquid including an electrolyte and a solvent, and gelling the electrolyte liquid thereby. Examples of the gelling agent include an organic compound having a molecular weight of 1000 or less, an Si-containing compound having a molecular weight in the range of 500 to 5000, an organic salt obtained from a particular acidic compound and a particular basic compound, a sorbitol derivative, and polyvinylpyridine.

Furthermore, a method of confining a matrix polymer, a crosslinking type polymer compound or monomer, a crosslinking agent, an electrolyte, and a solvent, in a polymer may be used.

Preferred examples of the matrix polymer include a polymer having a nitrogen-containing heterocyclic ring in a repeating unit in the main chain or in a side chain, and a crosslinked structure formed by reacting the polymer with an electrophilic compound; a polymer having a triazine structure, a polymer having a ureide structure, a polymer containing a liquid crystalline compound, a polymer having an ether bond, a polyvinylidene fluoride-based polymer, a methacrylate or acrylate-based polymer, a thermosetting resin, crosslinked polysiloxane, polyvinyl alcohol (PVA), a clathrate compound of polyalkylene glycol and dextrin, a system incorporated with an oxygen-containing or sulfur-containing polymer, and a naturally occurring polymer. An alkali-swellable polymer, a polymer having a cation moiety and a component capable of forming a charge transfer complex with iodine within one polymer molecule, or the like may be added to those matrix polymers.

A system containing, as a matrix polymer, a crosslinked polymer formed by reacting a bifunctional or higher-functional isocyanate as one component with a functional group such as a hydroxyl group, an amino group or a carboxyl group, may also be used. Furthermore, a crosslinked polymer by a hydrosilyl group and a double-bonded compound, a crosslinking method involving reacting polysulfonic acid, polycarboxylic acid or the like with a divalent or higher-valent metal ion compound, and the like may also be used.

Examples of the solvent that can be used with preference in combination with the quasi-solid electrolyte described above, include particular phosphates, a mixed solvent containing ethylene carbonate, a solvent having a particular relative permittivity, and the like. A liquid electrolyte solution may be retained in a solid electrolyte membrane or in pores, and preferred examples of the method include the usage of an electrically conductive polymer membrane, a fibrous solid, and a fabric-like solid such as filter.

A solid-state charge-transport layer, such as a p-type semiconductor or a hole-transporting material, for example, CuI or CuNCS, may also be used in place of a liquid electrolyte and a quasi-solid-state electrolyte as described above. Moreover, electrolytes described in Nature, vol. 486, p. 487 (2012) and the like may be used. For a solid charge-transport layer, an organic hole-transporting material may be used. Preferred examples of the hole-transport layer include electrically conductive polymers such as polythiophene, polyaniline, polypyrrole, and polysilane; a spiro compound in which two rings share a central element adopting a tetrahedral structure, such as C and Si; aromatic amine derivatives such as triarylamine; triphenylene derivatives; nitrogen-containing heterocycle derivatives; and liquid crystalline cyano derivatives.

The redox pair serves as an electron carrier, and thus it is required to have a certain concentration. The concentration is preferably 0.01 mol/L or more, more preferably 0.1 mol/L or more, and particularly preferably 0.3 mol/L or more, in total. The upper limit in this case is not particularly limited but is usually about 5 mol/L.

—Co-Adsorbent—

In the photoelectric conversion element of the present invention, a co-adsorbent is preferably used in combination with the metal complex dye of the present invention or another dye to be used if necessary. As such a co-adsorbent, a co-adsorbent having at least one acidic group (preferably a carboxyl group or a salt thereof) is preferable, and examples of the co-adsorbent include a fatty acid and a compound having a steroid skeleton. The fatty acid may be a saturated fatty acid or an unsaturated fatty acid. Examples thereof include a butanoic acid, a hexanoic acid, an octanoic acid, a decanoic acid, a hexadecanoic acid, a dodecanoic acid, a palmitic acid, a stearic acid, an oleic acid, a linoleic acid, and a linolenic acid.

Examples of the compound having a steroid skeleton include a cholic acid, a glycocholic acid, a chenodeoxycholic acid, a hyocholic acid, a deoxycholic acid, a lithocholic acid, and ursodeoxycholic acid. Among these, a cholic acid, a deoxycholic acid, and a chenodeoxycholic acid are preferable; and a chenodeoxycholic acid is more preferable.

A preferred co-adsorbent is a compound represented by the following formula (CA).

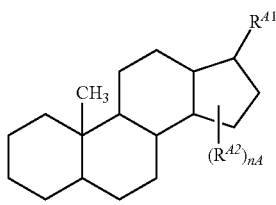

Formula (CA)

In the formula (CA), $R^{41}$ represents a substituent having an acidic group. $R^{42}$ represents a substituent. nA represents an integer of 0 or more.

The acidic group has the same meaning as described above, and the preferable range is also the same.

Of these, $R^{41}$ is preferably an alkyl group substituted with any one of a carboxyl group, a sulfo group, and a salt thereof; and further preferably —CH(CH$_3$)CH$_2$CH$_2$CO$_2$H, or —CH(CH$_3$)CH$_2$CH$_2$CONHCH$_2$CH$_2$SO$_3$H.

Examples of $R^{42}$ include those exemplified as the substituent T described later. Of these, an alkyl group, a hydroxyl group, an acyloxy group, an alkylaminocarbonyloxy group, and an arylaminocarbonyloxy group are preferable; and an alkyl group, a hydroxyl group, and an acyloxy group are more preferable.

nA is preferably from 2 to 4.

Examples of the specific compounds include the compounds mentioned as the compound having a steroid skeleton.

By adsorbing on the semiconductor fine-particles, the co-adsorbent that can be used in the present invention exhibits an effect on suppressing the inefficient association of the dye, and preventing reverse electron transfer from the semiconductor fine-particle surface to the redox system in the electrolyte. An amount to be used of the co-adsorbent is not particularly limited, and it is preferred, from the viewpoint of exhibiting effectively the effects, that the amount is preferably from 1 to 200 moles, more preferably from 10 to 150 moles, and particularly preferably from 20 to 50 moles, with respect to 1 mole of the dyes.

<Substituent T>

The specification uses an expression "compound" (including complex and dye) to mean, in addition to the compound itself, its salts, its complex and its ion. Further, a substituent with which substitution or non-substitution is not explicitly described in the present specification (the same applies to a linking group and a ligand), means that the substituent may have an arbitrary substituent. The same is also true on a compound with which substitution or non-substitution is not explicitly described. Preferable examples of the substituent include the following substituent T.

In the present specification, the simple description only as a "substituent" means to refer to this substituent T. Further, in the case where each of the substituents, for example, like an alkyl group, is described in a simplistic form, both a preferable range and specific examples for the corresponding group of the substituent T are applied to.

The substituent T includes the followings:

an alkyl group (preferably an alkyl group having 1 to 20 carbon atoms, e.g. methyl, ethyl, isopropyl, t-butyl, pentyl, heptyl, 1-ethylpentyl, benzyl, 2-ethoxyethyl, 1-carboxymethyl, or trifluoromethyl), an alkenyl group (preferably an alkenyl group having 2 to 20 carbon atoms, e.g. vinyl, allyl, or oleyl), an alkynyl group (preferably an alkynyl group having 2 to 20 carbon atoms, e.g. ethynyl, butadiynyl, or phenylethynyl), a cycloalkyl group (preferably a cycloalkyl group having 3 to 20 carbon atoms, e.g. cyclopropyl, cyclopentyl, cyclohexyl, or 4-methylcyclohexyl), an cycloalkenyl group (preferably a cycloalkenyl group having 5 to 20 carbon atoms, e.g. cyclopentenyl, or cyclohexenyl), an aryl group (preferably an aryl group having 6 to 26 carbon atoms, e.g. phenyl, 1-naphthyl, 4-methoxyphenyl, 2-chlorophenyl, or 3-methylphenyl), a heterocyclic group (preferably a 5- or 6-membered heterocyclic group having 2 to 20 carbon atoms and at least one oxygen atom, sulfur atom, or nitrogen atom, e.g. 2-pyridyl, 4-pyridyl, 2-imidazolyl, 2-benzimidazolyl, 2-thiazolyl, or 2-oxazolyl), an alkoxy group (preferably an alkoxy group having 1 to 20 carbon atoms, e.g. methoxy, ethoxy, isopropyloxy, or benzyloxy), an alkenyloxy group (preferably an alkenyloxy group having 2 to 20 carbon atoms, e.g. vinyloxy or allyloxy), an alkynyloxy group (preferably an alkynyloxy group having 2 to 20 carbon atoms, e.g. 2-propynyloxy or 4-butynyloxy), a cycloalkyloxy group (preferably an cycloalkyloxy group having 3 to 20 carbon atoms, e.g. cyclopropyloxy, cyclopentyloxy, cyclohexyloxy, or 4-methylcyclohexyloxy), an aryloxy group (preferably an aryloxy group having 6 to 26 carbon atoms, e.g. phenoxy, 1-naphthyloxy, 3-methylphenoxy, or 4-methoxyphenoxy), a heterocyclic oxy group (e.g. imidazolyloxy, benzoimidazolyloxy, thiazolyloxy, benzothiazolyloxy, triazinyloxy, or purinyloxy);

an alkoxycarbonyl group (preferably an alkoxycarbonyl group having 2 to 20 carbon atoms, e.g. ethoxycarbonyl, or 2-ethylhexyloxycarbonyl), a cycloalkoxycarbonyl group (preferably a cycloalkoxycarbonyl group having 4 to 20 carbon atoms, e.g. cyclopropyloxycarbonyl, cyclopentyloxycarbonyl, cyclohexyloxycarbonyl), an aryloxycarbonyl group (preferably an aryloxycarbonyl group having 6 to 20 carbon atoms, e.g. phenyloxycarbonyl, or naphthyloxycarbonyl), an amino group (preferably an amino group having 0 to 20 carbon atoms including an alkylamino group, an alkenylamino group, an alkynylamino group, a cycloalkylamino group, a cycloalkenylamino group, an arylamino group, and a heterocyclic amino group, e.g. amino, N,N-dimethylamino, N,N-diethylamino, N-ethylamino, N-allylamino, N-(2-propinyl)amino, N-cyclohexylamino, N-cyclohexenylamino, anilino, pyridylamino, imidazolylamino, benzimidazolylamino, thiazolylamino, benzothiazolylamino, or triazinylamino), a sulfamoyl group (preferably a sulfamoyl group having 0 to 20 carbon atoms, preferably an alkyl-, cycloalkyl- or aryl-sulfamoyl group, e.g. N,N-dimethylsulfamoyl, N-cyclohexylsulfamoyl or N-phenylsulfamoyl), an acyl group (preferably an acyl group having 1 to 20 carbon atoms, e.g. acetyl, cyclohexylcarbonyl or benzoyl), an acyloxy group (preferably an acyloxy group having 1 to 20 carbon atoms, e.g. acetyloxy, cyclohexylcarbonyloxy, or benzoyloxy), a carbamoyl group (preferably a carbamoyl group having 1 to 20 carbon atoms, preferably an alkyl-, cycloalkyl- or aryl-carbamoyl group, e.g. N,N-dimethylcarbamoyl, N-cyclohexylcarbamoyl, or N-phenylcarbamoyl), an acylamino group (preferably an acylamino group having 1 to 20 carbon atoms, e.g. acetylamino, cyclohexylcarbonylamino or benzoylamino), a sulfonamide group (preferably a sulfonamide group having 0 to 20 carbon atoms, preferably an alkyl-, cycloalkyl- or aryl-sulfonamide group, e.g. methane sulfonamide, benzene sulfonamide, N-methyl methane sulfonamide, N-cyclohexyl sulfonamide or N-ethyl benzene sulfonamide), an alkylthio group (preferably an alkylthio group having 1 to 20 carbon atoms, e.g. methylthio, ethylthio, isopropylthio, or benzylthio), a cycloalkylthio group (preferably an a cycloalkylthio group having 3 to 20 carbon atoms, e.g. cyclopropylthio, cyclopentylthio, cyclohexylthio, 4-methyl cyclohexylthio), an arylthio group (preferably an arylthio group having 6 to 26 carbon atoms, e.g. phenylthio, 1-naphthylthio, 3-methylphenylthio, or 4-methoxyphenylthio), an alkyl-, cycloalkyl- or aryl-sulfonyl group (preferably a sulfonyl group having 1 to 20 carbon atoms, e.g. methylsulfonyl, ethylsulfonyl, cyclohexyl sulfonyl or benzene sulfonyl), a silyl group (preferably a silyl group having 1 to 20 carbon atoms, preferably an alkyl-, aryl-, alkoxy-, or aryloxy-substituted silyl group, e.g. triethylsilyl, triphenylsilyl, diethylbenzylsilyl, or dimethylphenylsilyl), a silyloxy group (preferably a silyloxy group having 1 to 20 carbon atoms, preferably an alkyl-, aryl-, alkoxy-, or aryloxy-substituted silyloxy group, e.g. triethylsilyloxy, triphenylsilyloxy, diethylbenzylsilyloxy, or dimethylphenylsilyloxy), a hydroxyl group, a cyano group, a nitro group, a halogen atom (e.g. fluorine atom, chlorine atom, bromine atom, or iodine atom), a carboxyl group, a sulfo group, a phosphonyl group, a phosphoryl group, and a boric-acid group; more preferably an alkyl group, an alkenyl group, a cycloalkyl group, an aryl group, a heterocyclic group, an alkoxy group, a cycloalkoxy group, an aryloxy group, an alkoxycarbonyl group, an cycloalkoxycarbonyl group, the above-mentioned amino group, an acylamino group, a cyano group, or a halogen atom; and particularly preferably an alkyl group, an alkenyl group, a heterocyclic group, an alkoxy group, an alkoxycarbonyl group, an amino group, an acylamino group, or a cyano group.

When the compound or the substituent or the like contains an alkyl group or an alkenyl group, these may be a straight chain or a branched chain, and these may be substituted or unsubstituted. Further, in the case of containing an aryl group, a heterocyclic group or the like, these may be a single ring or a fused ring, and may be substituted or unsubstituted.

<Counter Electrode (Opposite Electrode)>

The counter electrode is preferably an electrode working as a positive electrode in the dye-sensitized solar cell (photoelectrochemical cell). The counter electrode usually has the same meaning as the electrically-conductive support described above, but in a construction which is likely to maintain a sufficient strength, a support is not necessarily required. A preferred structure of the counter electrode is a structure having a high charge collecting effect. At least one of the electrically-conductive support and the counter electrode as mentioned above should be substantially transparent, in order for light to reach the photoconductor layer. In the dye-sensitized solar cell of the present invention, the electrically-conductive support is preferably transparent to allow sunlight to inject from the support side. In this case, the counter electrode further preferably has properties of reflecting light. As the counter electrode of the dye-sensitized solar cell, a glass or plastic plate on which a metal or an electrically-conductive oxide is deposited is preferable, and a glass plate on which platinum is deposited is particularly preferable. In the dye-sensitized solar cell, a lateral side of the cell is preferably sealed with a polymer, an adhesive, or the like, in order to prevent evaporation of the component.

The present invention can be applied to the photoelectric conversion elements and the dye-sensitized solar cells described, for example, in Japanese Patent No. 4260494, JP-A-2004-146425, JP-A-2000-340269, JP-A-2002-289274, JP-A-2004-152613, JP-A-9-27352. In addition, the present invention can be applied to the photoelectric conversion elements and the dye-sensitized solar cells described, for example, in JP-A-2004-152613, JP-A-2000-90989, JP-A-2003-217688, JP-A-2002-367686, JP-A-2003-323818, JP-A-2001-43907, JP-A-2000-340269, JP-A-2005-85500, JP-A-2004-273272, JP-A-2000-323190, JP-A-2000-228234, JP-A-2001-266963, JP-A-2001-185244, JP-T-2001-525108, JP-A-2001-203377, JP-A-2000-100483, JP-A-2001-210390, JP-A-2002-280587, JP-A-2001-273937, JP-A-2000-285977, JP-A-2001-320068.

<<Dye Solution, Dye-Adsorbed Electrode Using the Same, and Production Method of Dye-Sensitized Solar Cell>>

In the present invention, a dye-adsorbed electrode is preferably produced using a dye solution containing the metal complex dye of the present invention.

The foregoing dye solution contains the metal complex dye of the present invention dissolved in a solvent, and may comprise a co-adsorbent and other ingredients as needed.

Examples of the solvent to be used include solvents described in JP-A-2001-291534, but the solvent is not particularly limited thereto. In the present invention, organic solvents are preferred. More preferred are alcohols, amides, nitriles, hydrocarbons, and a mixed solvent of two or more kinds of these solvents. As the mixed solvent, preferred are mixed solvents of alcohols and a solvent selected from amides, nitriles, and hydrocarbons. More preferred are mixed solvents of alcohols and amides and mixed solvents of alcohols and hydrocarbons, and particularly preferred are mixed solvents of alcohols and amides. In specific, methanol, ethanol, propanol, butanol, dimethylformamide, and dimethylacetamide are preferred.

The dye solution preferably contains a co-adsorbent, and the co-adsorbent is preferably the aforementioned ones. Among them, the compound represented by Formula (CA) is preferred.

The dye solution of the present invention is preferably one in which the concentrations of the metal complex dye and the co-adsorbent have been adjusted so that the dye solution can be used as it is at the time of preparation of a photoelectric conversion element or a dye-sensitized solar cell. In the present invention, the metal complex dye of the present invention is preferably contained in an amount of from 0.001 to 0.1% by mass.

In the dye solution, it is particularly preferable to adjust the water content, and thus in the present invention, it is preferred that the content (content rate) of water is adjusted to the range of from 0 to 0.1% by mass.

Similarly, it is also preferable to adjust the water content in the electrolyte in a photoelectric conversion element and a dye-sensitized solar cell, in order to achieve the effects of the present invention effectively. Thus, it is preferred that the content (content rate) of water in the electrolyte solution is adjusted to the range of from 0 to 0.1% by mass. The foregoing adjustment of the electrolyte is particularly preferably carried out with the dye solution.

In the present invention, a dye-adsorbed electrode is preferably a semiconductor electrode for dye-sensitized solar cell, which is prepared by allowing the surface of the semiconductor fine particles provided on the semiconductor electrode, to carry the metal complex dye, with using the above dye solution.

In other words, the dye-adsorbed electrode for dye-sensitized solar cell preferably has a photoconductor layer which is obtained by coating a composition obtained from the aforementioned dye solution, on an electrically-conductive support provided with semiconductor fine particles, and curing the composition after coating.

In the present invention, it is preferable that a dye-sensitized solar cell be produced by using the dye-adsorbed electrode for dye-sensitized solar cell, preparing an electrolyte and a counter electrode, and performing an assembly with using them.

EXAMPLES

The present invention will be described in more detail based on examples given below, but the invention is not meant to be limited by these.

Example 1

Synthesis of Metal Complex Dye

Synthesis of Metal Complex Dye Dye-1

Metal complex dye Dye-1 was synthesized according to the following reaction scheme.

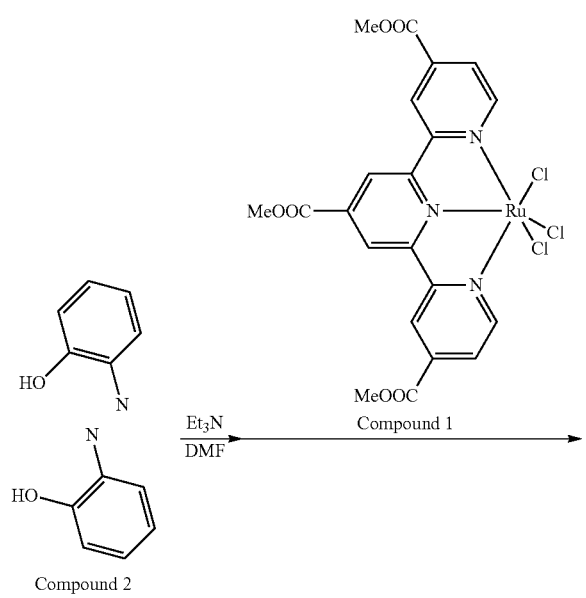

Compound 2

Compound 1

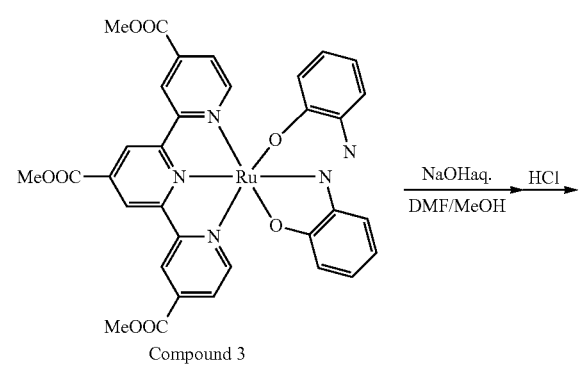

Compound 3

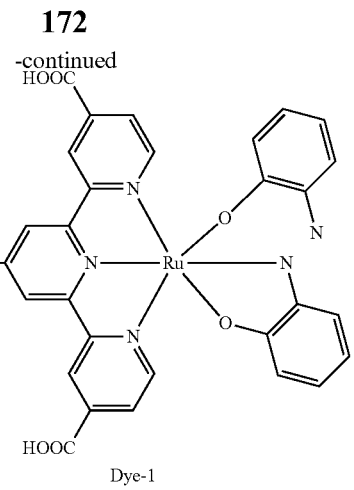

Dye-1

(i) Synthesis of Compound 3

Into a 10-ml eggplant flask, 80 mg of Compound 2 and 2 ml of N,N-dimethylformamide were added, and stirred. Thereto, 0.11 ml of triethylamine was added, and, thereafter, 200 mg of Compound 1 was added, and the mixture was heated and stirred for 6 hours at 120° C. After bringing back the temperature thereof to room temperature, 10 ml of methanol was added, and precipitates were collected by suction filtration, and then, washed with methanol, to obtain 110 mg of Compound 3.

(ii) Synthesis of Metal Complex Dye Dye-1

To a 10 ml-eggplant flask, 350 mg of Compound 3 and 1 ml of N,N-dimethylformamide were added and stirred. Thereto, a solution prepared by dissolving 14 mg of sodium hydroxide in 0.3 ml of distilled water was added dropwise, and the mixture was stirred for 30 minutes at 35 to 45° C. The resultant was further added with methanol, and further stirred for 1.5 hours. Then, a hydrochloric acid was added thereto until pH 2 was reached. The produced precipitates were filtered, washed with water, and dried, to obtain 32 mg of Metal complex dye Dye-1. Identification of the obtained compound was conducted by ESI-MS.

ESI-MS: $[M-H]^+=680.0$

Figure 3:
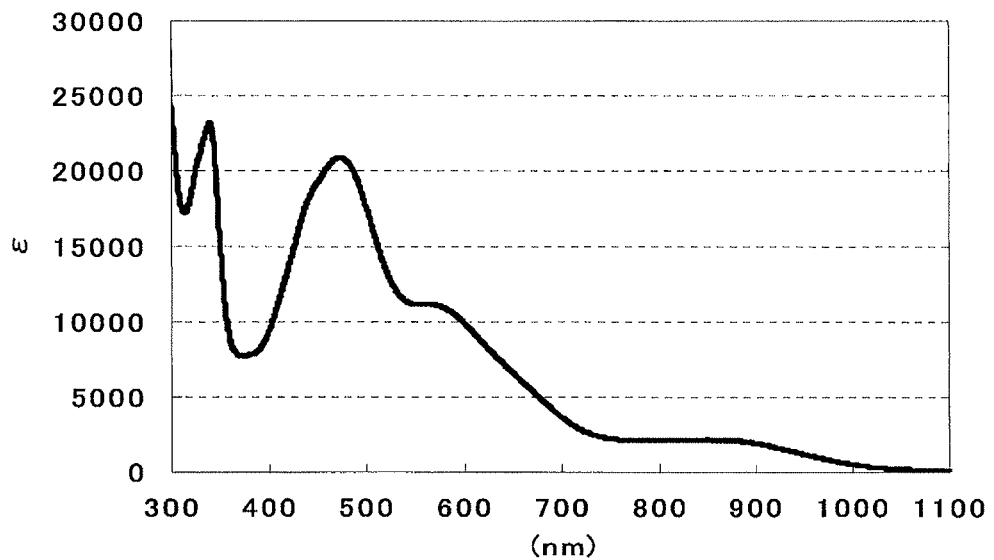
FIG. 3 is a visible absorption spectrum diagram of metal complex dye Dye-1 synthesized in Examples, in a DMF solution.
Figure 4:
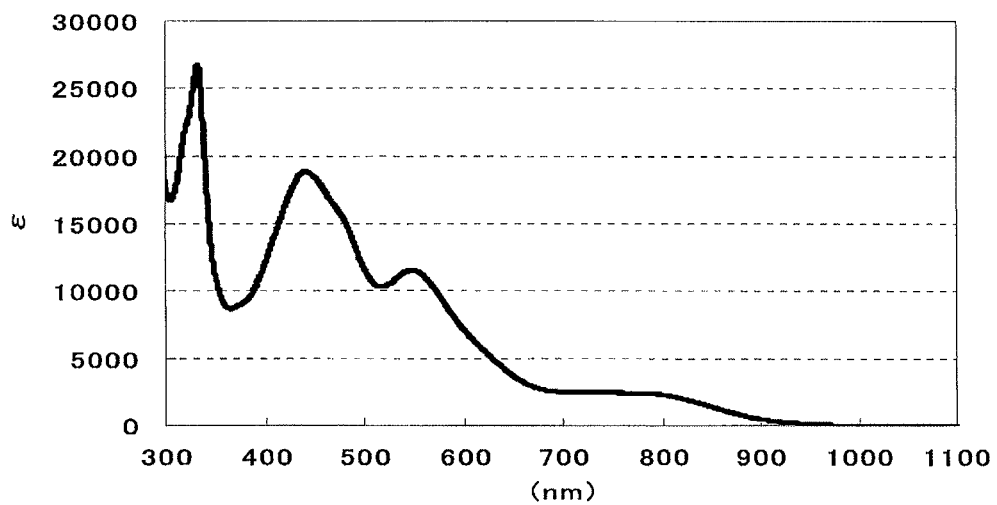
FIG. 4 is a visible absorption spectrum diagram of metal complex dye Dye-1 synthesized in Examples, in a TBAOH/methanol solution.

Visible absorption spectra are shown in FIGS. 3 and 4. With the concentration of 17 won of Metal complex dye Dye-1, the absorption was measured with UV-3600 manufactured by Shimadzu Corporation.

FIG. 3 is a spectrum diagram when the solvent for measurement was N,N-dimethylformamide (DMF), and FIG. 4 is a spectrum diagram in a methanol solution containing tetrabutylammonium hydroxide (TBAOH) at 340 mmol/L.

Figure 5:
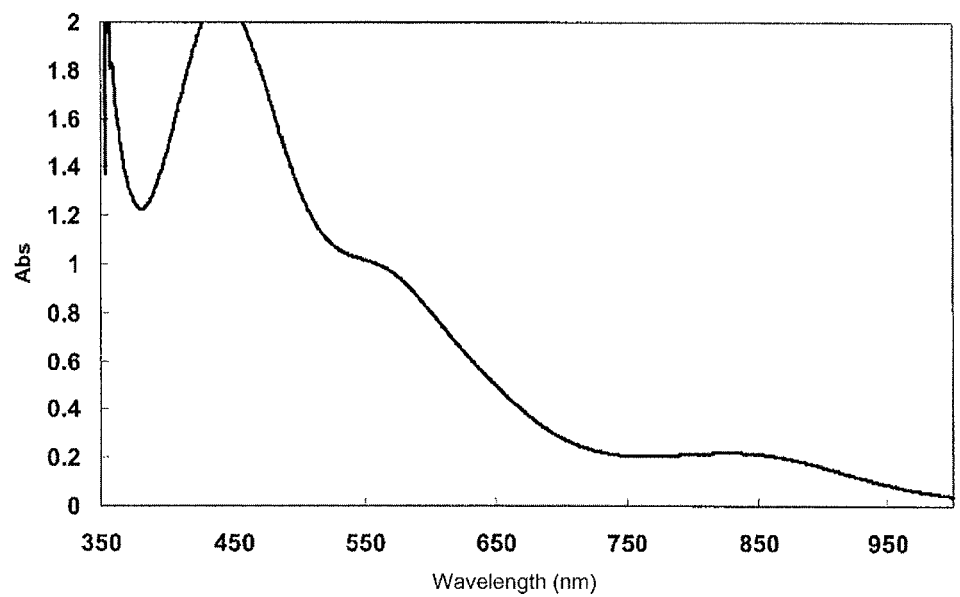
FIG. 5 is a visible absorption spectrum diagram of metal complex dye Dye-1 synthesized in Examples, in a titanium oxide film formed by adsorbing it on titanium oxide.

In addition, FIG. 5 shows a visible absorption spectrum in a model semiconductor film (a titanium oxide film on which metal complex dye Dye-1 had been adsorbed), in accordance with the sample No. 101 in Example 2 described later.

It can be seen that the visible absorption spectrum in the methanol solution containing tetrabutylammonium hydroxide (TBAOH) at 340 mmol/L (FIG. 4) is similar to the visible absorption spectrum in the titanium oxide film on which metal complex dye Dye-1 had been adsorbed (FIG. 5).

Synthesis of Metal Complex Dye Dye-5

Metal complex dye Dye-5 was synthesized according to the following reaction scheme.

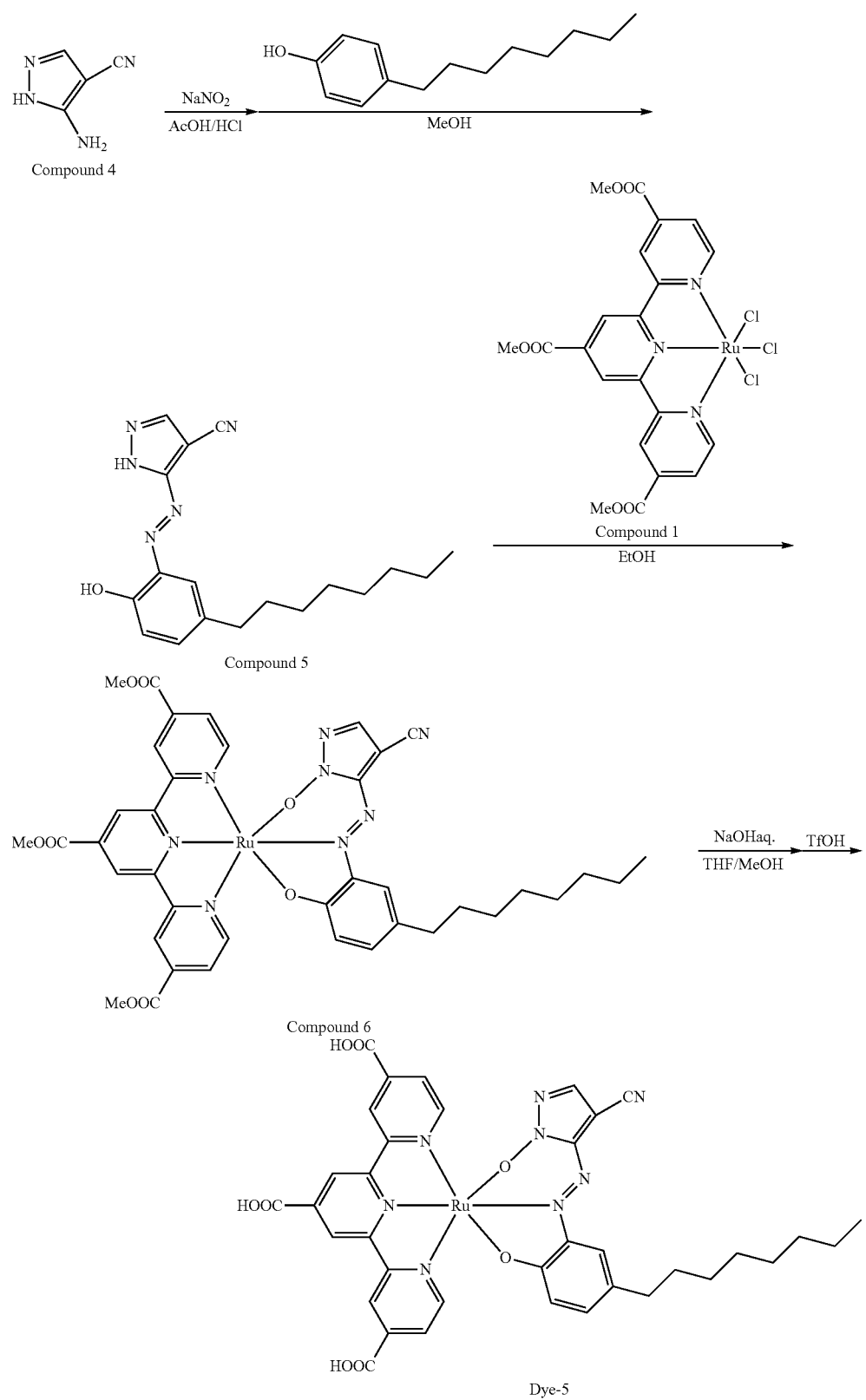
(i) Synthesis of Compound 5
Into a 100-ml three-necked flask, 0.5 g of Compound 4, 3 ml of acetic acid, and 1.63 ml of hydrochloric acid were added, and stirred. The flask was cooled in an ice bath to 5° C. or less. Thereto, a solution containing 0.408 g of sodium nitrite dissolved in 1 ml of distilled water was slowly added dropwise, and the resultant was stirred for 30 minutes. Separately, 1.11 g of 4-octylphenol and 10 ml of methanol were added in a 100-ml three-necked flask. Thereto, while stirring and keeping the temperature at 10° C. or less with an ice bath, the reaction solution including the diazonium salt was slowly added dropwise and reacted for 1 hour. After bringing back the temperature thereof to room temperature, the precipitate was filtered, washed with water, and washed with the mixed solution of isopropyl alcohol and hexane, to obtain 520 mg of Compound 5.

(ii) Synthesis of Compound 6

Into a 10-ml eggplant flask, 100 mg of Compound 5 and 3 ml of ethanol were added and then stirred. Thereto, 0.16 ml of triethylamine was added, then 172 mg of Compound 1 was added, and the mixture was heated and refluxed for 6 hours. After bringing back the temperature thereof to room temperature, 10 ml of ethanol was added thereto, and the precipitate was suction filtered, followed by washing with ethanol. The resultant was purified by silica gel column chromatography using methylene chloride/methanol as the eluent, thereby obtaining 164 mg of Compound 6.

(iii) Synthesis of Metal Complex Dye Dye-5

Into a 10-ml eggplant flask, 160 mg of Compound 6, 1 ml of tetrahydrofuran, and 1 ml of methanol were added, and stirred. Thereto, a sodium hydroxide aqueous solution was added dropwise, and then the mixture was stirred for 1 hour at room temperature. Then, a 1N trifluoro acetate aqueous solution was added until the pH became 2. The resultant precipitate was filtered, washed with water, and dried, to obtain 58 mg of Metal complex dye Dye-5. Identification of the obtained compound was conducted by ESI-MS.

ESI-MS: $[M-H]^+=791$

Figure 6:
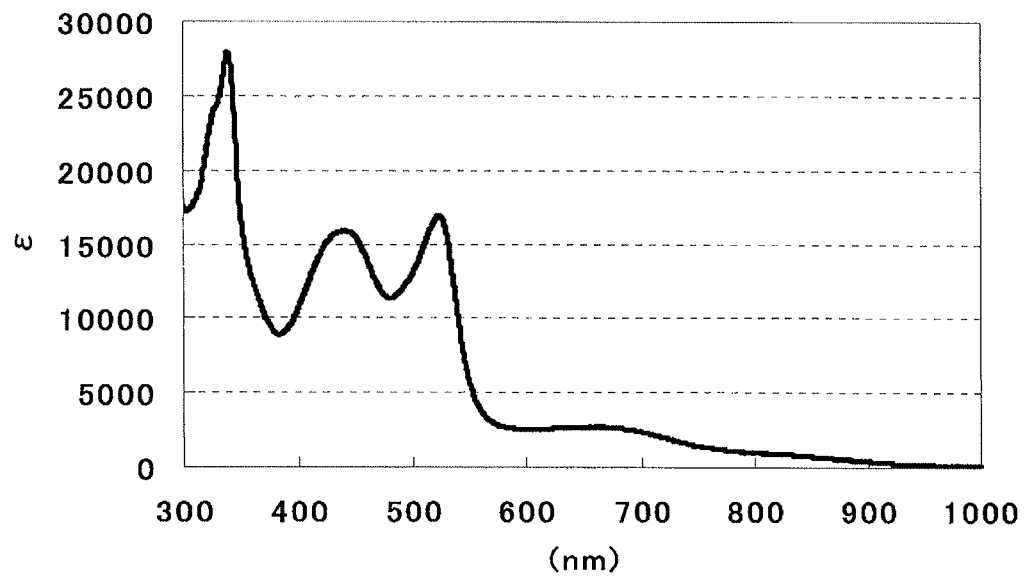
FIG. 6 is a visible absorption spectrum diagram of metal complex dye Dye-5 synthesized in Examples, in a TBAOH/methanol solution.

The visible absorption spectrum is shown in FIG. 6.

The measuring was performed in the same manner as Metal complex dye Dye-1. The measuring solvent was a 340 mmol/L tetrabutylammonium hydroxide (TBAOH) methanol solution.

Figure 7:
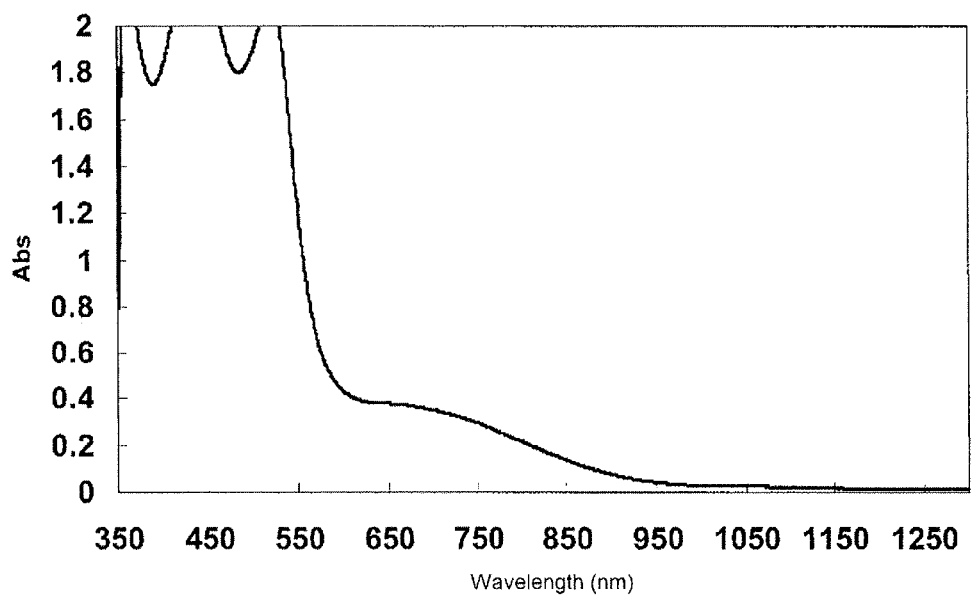
FIG. 7 is a visible absorption spectrum diagram of metal complex dye Dye-5 synthesized in Examples, in a titanium oxide film formed by adsorbing it on titanium oxide.

In addition, FIG. 7 illustrates a visible absorption spectrum in a model semiconductor film (a titanium oxide film on which metal complex dye Dye-5 had been adsorbed), in the same manner as metal complex dye Dye-1.

Synthesis of Metal Complex Dye Dye-6

Metal complex dye Dye-6 was synthesized in the same manner as Metal complex dye Dye-1 and Dye-5.

Identification of the thus-obtained Metal complex dye Dye-6 was conducted by ESI-MS.

Figure 8:
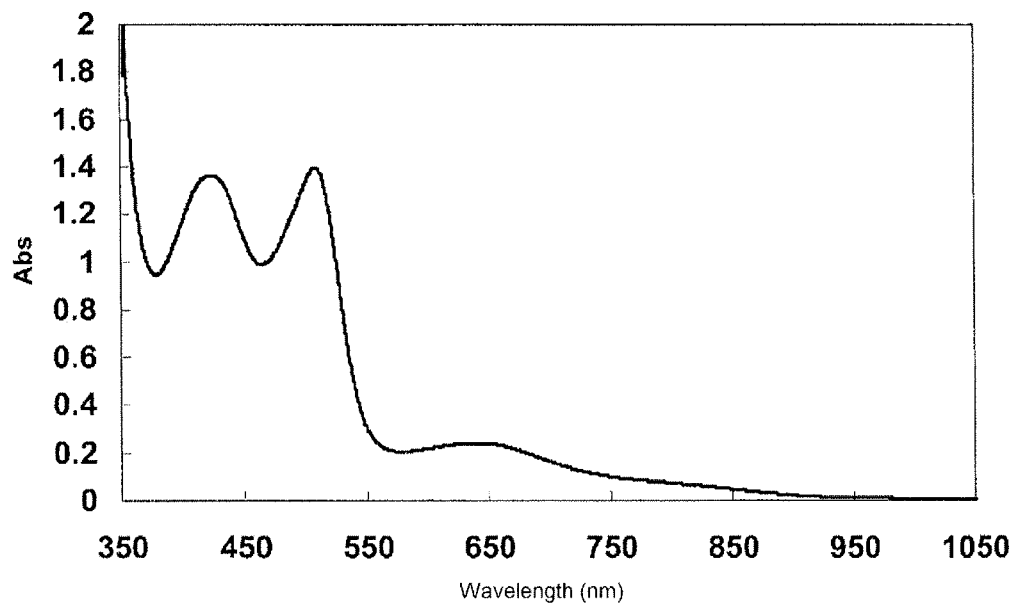
FIG. 8 is a visible absorption spectrum diagram of metal complex dye Dye-6 synthesized in Examples, in a titanium oxide film formed by adsorbing it on titanium oxide.

FIG. 8 illustrates a visible absorption spectrum in a model semiconductor film (a titanium oxide film on which metal complex dye Dye-6 had been adsorbed), in the same manner as metal complex dye Dye-1.

Synthesis of Metal Complex Dye Dye-11

Metal complex dye Dye-11 was synthesized according to the following reaction scheme.

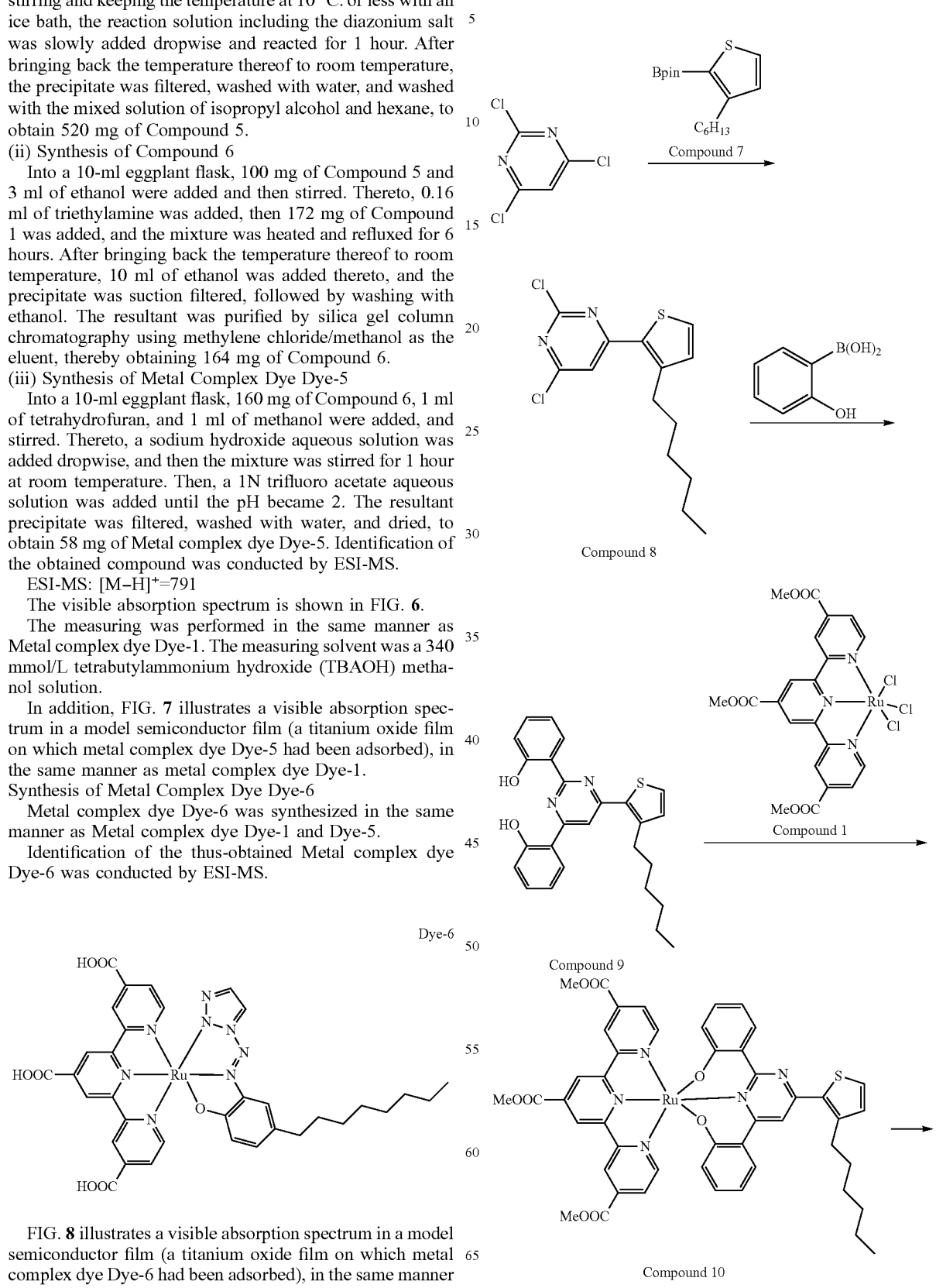

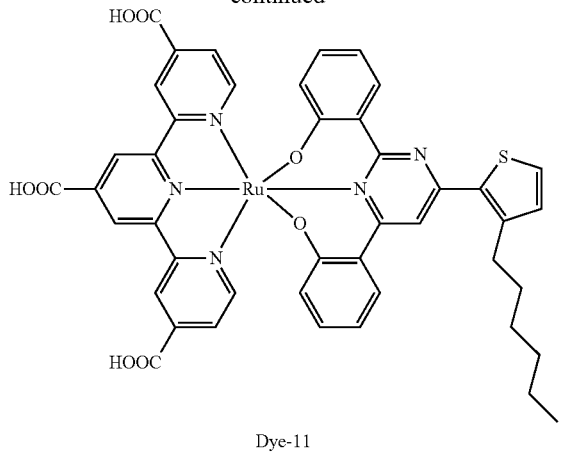

Dye-11

(i) Synthesis of Compound 8

Into a 100-ml three-necked flask, 9.04 g of potassium carbonate, 30 ml of distilled water, and 30 ml of toluene were added, and then, degassing and nitrogen substitution were performed. Then, 9 g of 2,4,6-trichloropyrimidine, 4.81 g of Compound 7, and 0.945 g of tetrakis(triphenylphosphine)palladium(0) were added, and the mixture was heated and refluxed for 9 hours at 120° C. After bringing back the temperature thereof to room temperature, the aqueous layer was removed, and the purification was performed with a silica gel column chromatography using hexane/ethyl acetate as an eluent, to obtain 83.4 g of Compound 8.

(ii) Synthesis of Compound 9

Into a 100-ml three-necked flask, 1.5 g of Compound 8, 4.04 g of potassium triphosphate, 15 ml of distilled water, and 15 ml of tetrahydrofuran were added, and then, degassing and nitrogen substitution were performed. 0.469 g of SPhos, 2.3 g of 2-hydroxyphenyl boron acid, and 0.107 g of palladium acetate were added, and the mixture was heated and stirred for 3.5 hours at 80° C. The pH was adjusted to acidic with a hydrochloric acid, the aqueous layer was removed, vacuum concentration was performed, and then, the purification was performed with a silica gel column chromatography using hexane/ethyl acetate as an eluent, to obtain 1.07 g of Compound 9. Identification of the thus-obtained compound was conducted by $^1$H-NMR.

(iii) Synthesis of Compound 10

Into a 50-ml eggplant flask, 71.4 mg of Compound 1, 50 mg of Compound 9, and 1 ml of methanol were added. While stirring the solution, 0.065 ml of triethylamine was added, and the mixture was heated and stirred for 3 hours at 80° C. After bringing back the temperature thereof to room temperature, the precipitate was filtered, and washed with methanol, to obtain 92 mg of Compound 10. Identification of the thus-obtained compound was conducted by $^1$H-NMR.

(iv) Metal Complex Dye Dye-11

Into a 100-ml three-necked flask, 90 mg of Compound 10, 5 ml of tetrahydrofuran, and 5 ml of methanol were added. While stirring the solution, 1.2 ml of a 3N sodium hydroxide aqueous solution was added dropwise thereto. The resultant was stirred for 3 hours at room temperature, and then the pH thereof was adjusted to be acidic with a 1 N trifluoromethanesulfonate/methanol solution. The precipitate was filtered, and washed with methanol, to obtain 80 mg of metal complex dye Dye-11. Identification of the thus-obtained compound was conducted by ESI-MS.

[M–H]$^+$=896.1

Figure 9:
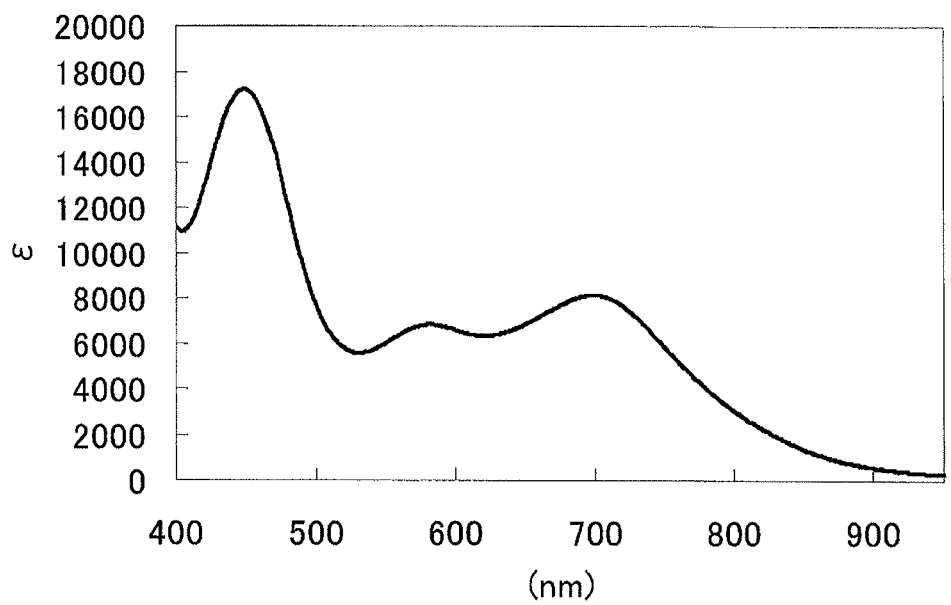
FIG. 9 is a visible absorption spectrum diagram of metal complex dye Dye-11 synthesized in Examples, in a TBAOH/methanol solution.

FIG. 9 illustrates the visible absorption spectrum in a 340 mmol/L tetrabutylammonium hydroxide (TBAOH) methanol solution, in the same manner as metal complex dye Dye-1.

Figure 10:
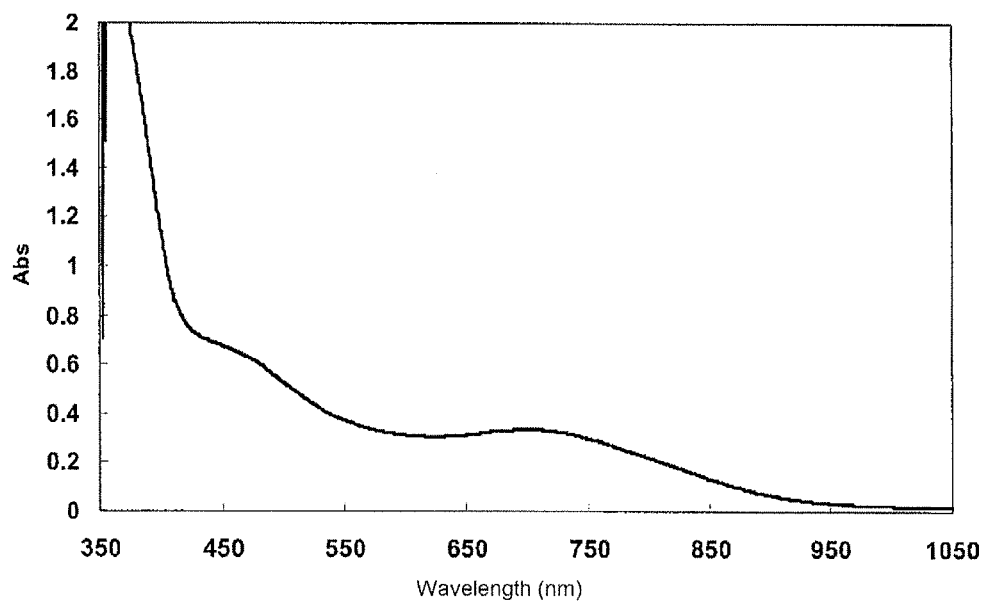
FIG. 10 is a visible absorption spectrum diagram of metal complex dye Dye-11 synthesized in Examples, in a titanium oxide film formed by adsorbing it on titanium oxide.

In addition, FIG. 10 illustrates a visible absorption spectrum in a model semiconductor film (a titanium oxide film on which metal complex dye Dye-11 had been adsorbed), in the same manner as metal complex dye Dye-1.

Synthesis of Metal Complex Dye Dye-12

Metal complex dye Dye-12 was synthesized in the same manner as Metal complex dye Dye-1 or 5.

Identification of the thus-obtained Metal complex dye Dye-12 was conducted by ESI-MS.

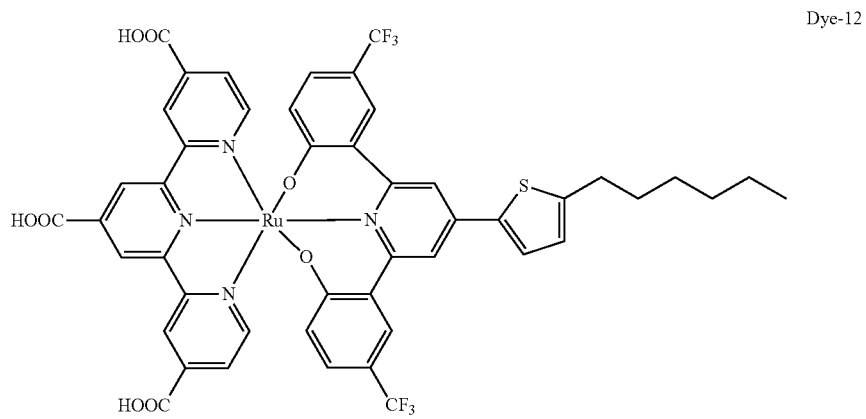

Dye-12

Figure 11:
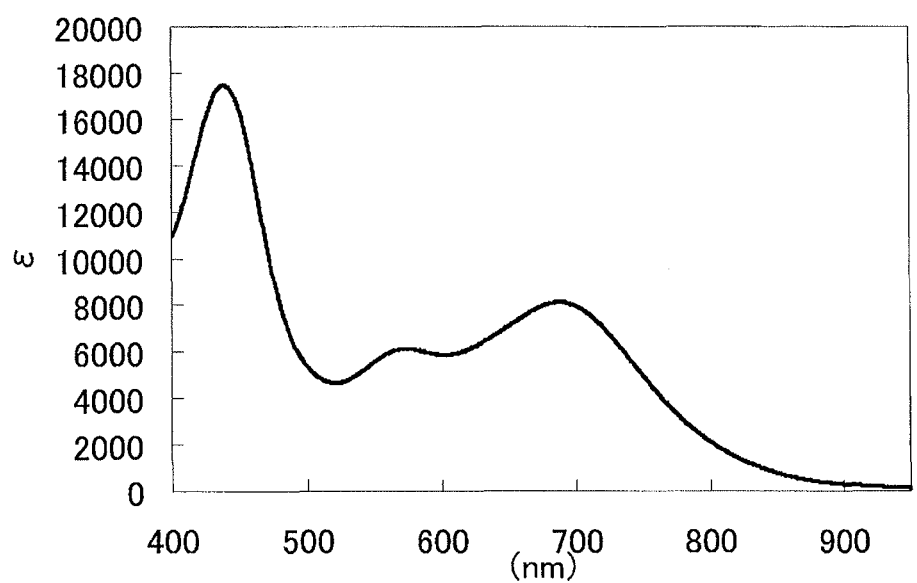
FIG. 11 is a visible absorption spectrum diagram of metal complex dye Dye-12 synthesized in Examples, in a titanium oxide film formed by adsorbing it on titanium oxide.

In addition, FIG. 11 illustrates a visible absorption spectrum in a model semiconductor film (a titanium oxide film on which metal complex dye Dye-12 had been adsorbed), in the same manner as metal complex dye Dye-1.

Synthesis of Metal Complex Dye Dye-2 to Dye-4, Dye-7 to Dye-10 and Dye-13 to Dye-24

The following Metal complex dye Dye-2 to Dye-4, Dye-7 to Dye-10 and Dye-13 to Dye-24 were synthesized in the same manner as Metal complex dye Dye-1, Dye-5, and Dye-11.

Identification of the thus-obtained Dye-2 to Dye-4, Dye-7 to Dye-10 and Dye-13 to Dye-24 was conducted by ESI-MS.

Dye-1
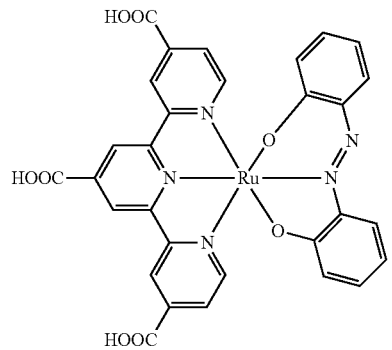
Dye-2
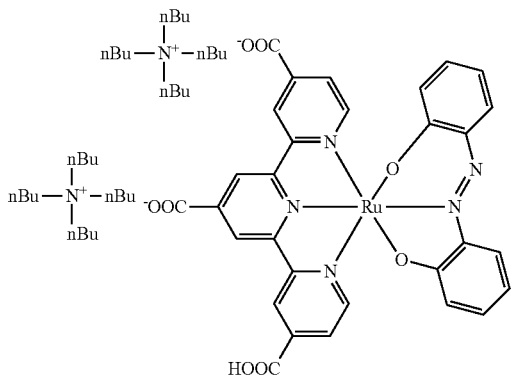
Dye-3
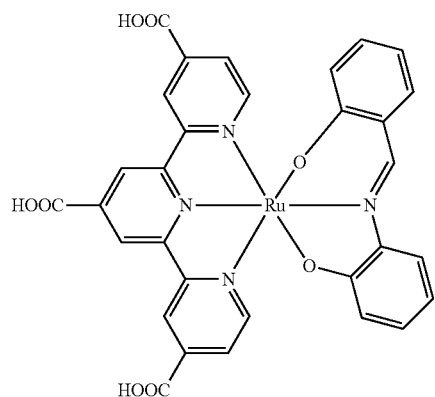
Dye-4
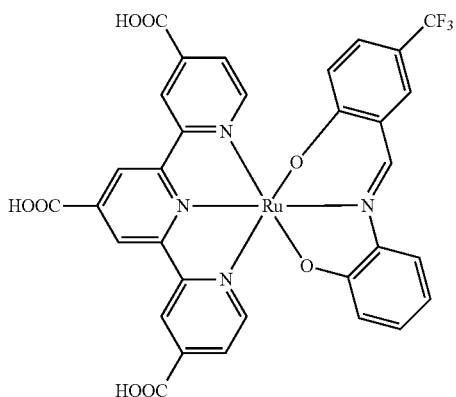
Dye-5
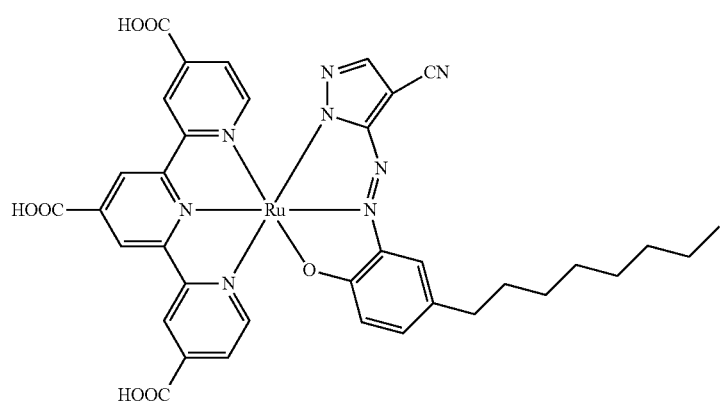
Dye-6
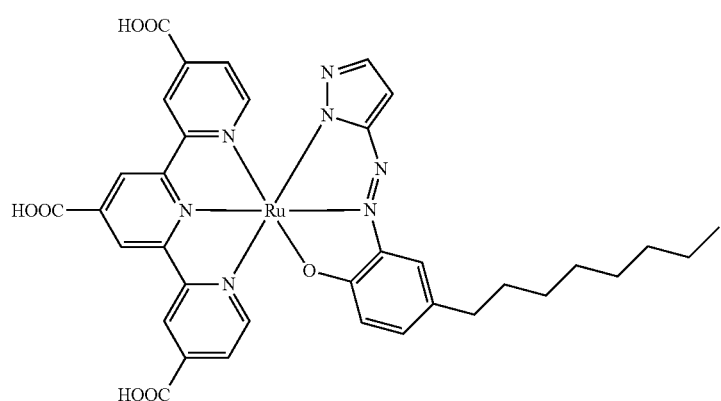

-continued
Dye-7
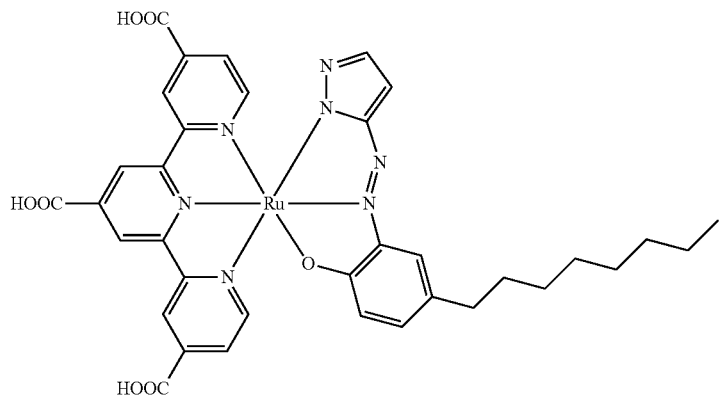
Dye-8
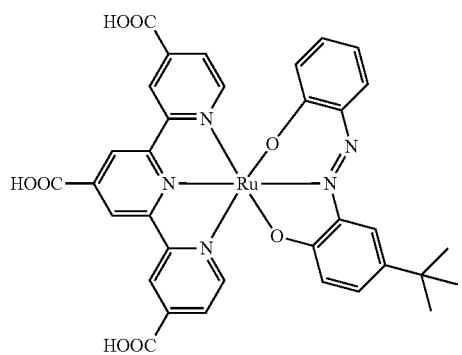
Dye-9
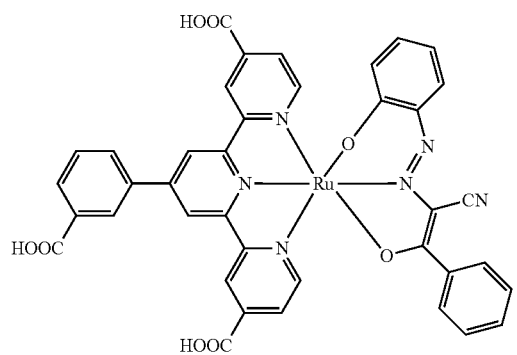
Dye-10
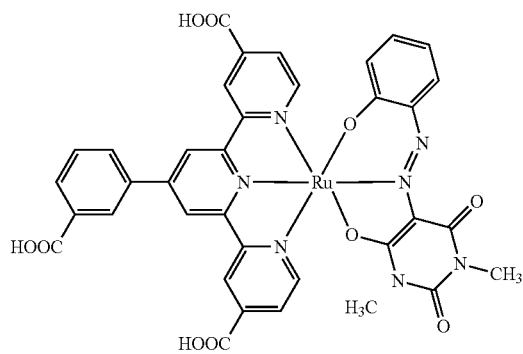
Dye-11
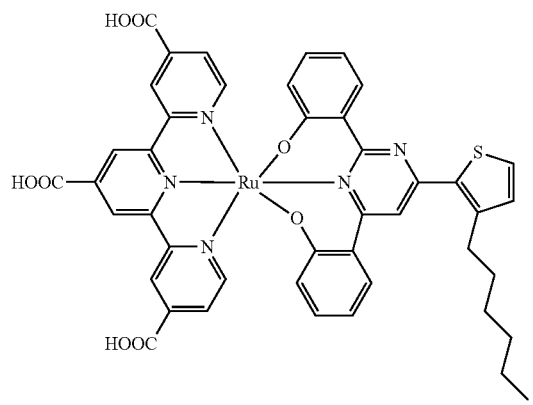
Dye-12
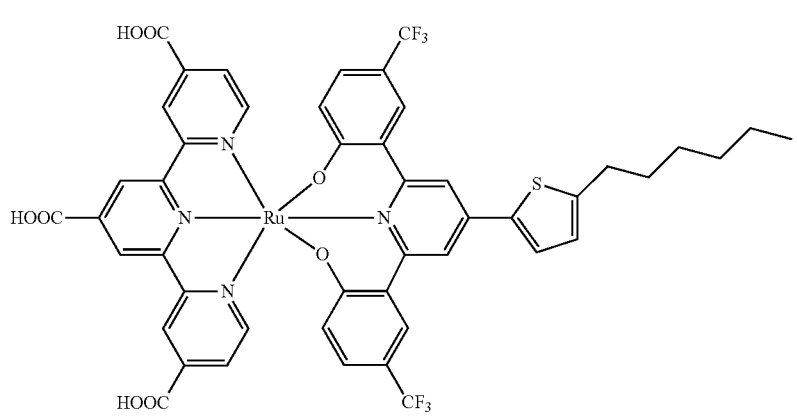

-continued
Dye-13
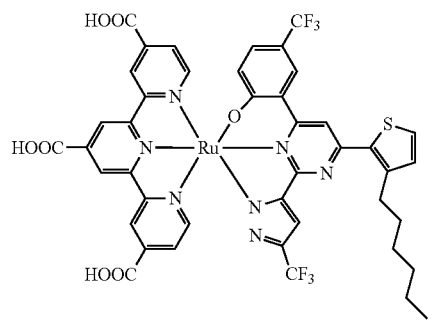
Dye-16
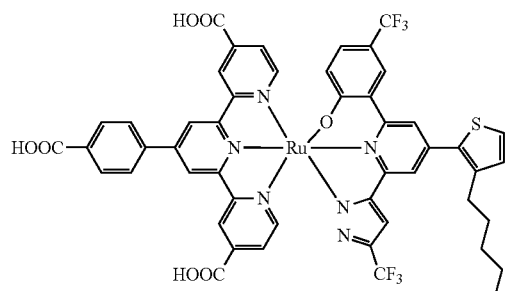
Dye-14
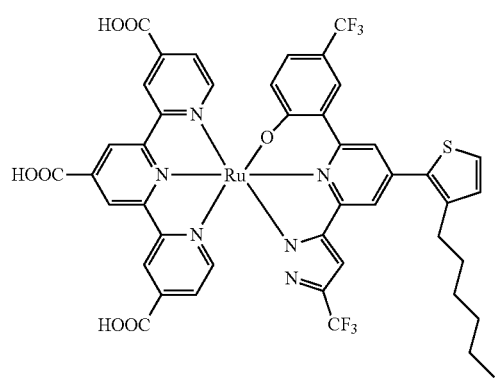
Dye-15
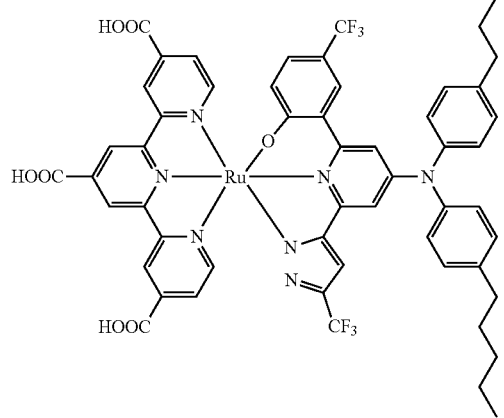
Dye-17
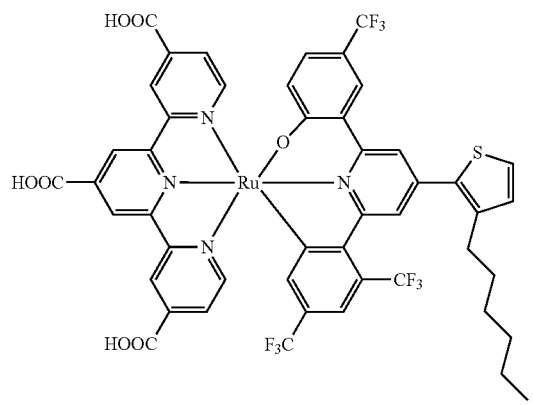
Dye-18
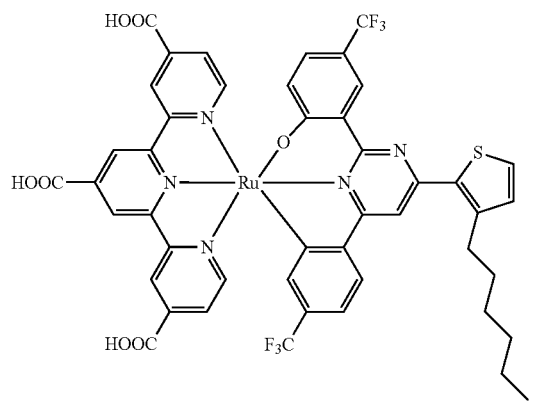
Dye-19
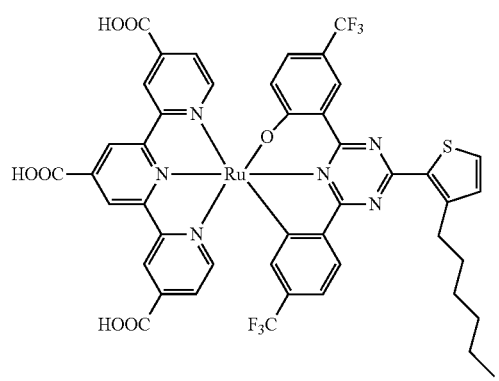
Dye-20
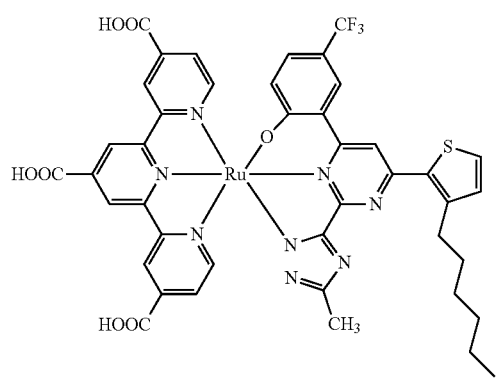

-continued

Dye-21

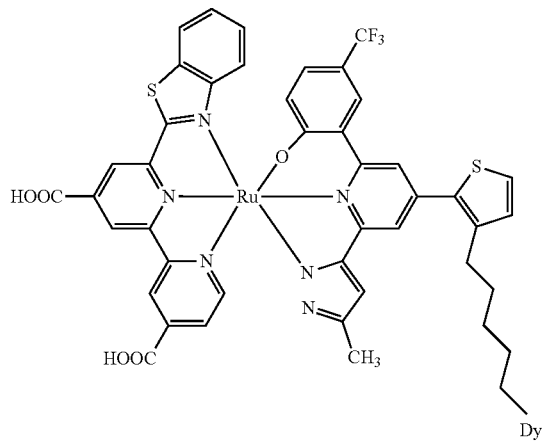

Dye-22

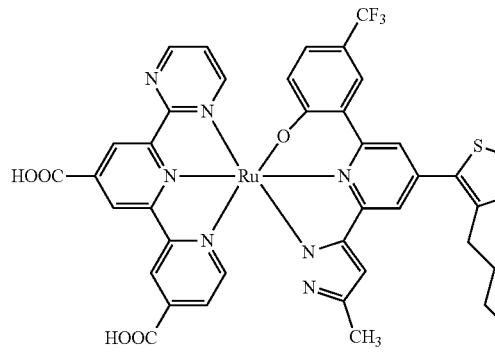

Dye-23

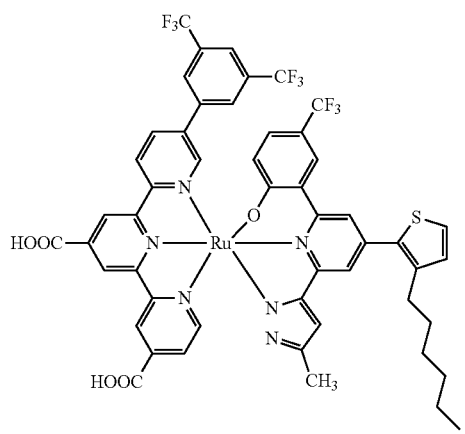

Dye-24

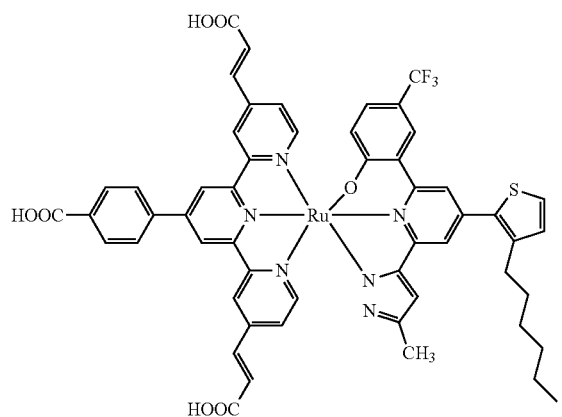

The results of ESI-MS of these metal complex dyes are shown in Table 1 below.

TABLE 1

| Metal complex dye | ESI-MS [M − H]⁺ |
| --- | --- |
| Dye-2 | 680.0, 242.3 |
| Dye-3 | 679.0 |
| Dye-4 | 747.0 |
| Dye-6 | 766.2 |
| Dye-7 | 842.2 |
| Dye-8 | 720.1 |
| Dye-9 | 807.1 |
| Dye-10 | 818.1 |
| Dye-12 | 1031.1 |
| Dye-13 | 1006.1 |
| Dye-14 | 1005.1 |
| Dye-15 | 1146.3 |
| Dye-16 | 1081.1 |
| Dye-17 | 1083.1 |
| Dye-18 | 1016.1 |
| Dye-19 | 1017.1 |
| Dye-20 | 952.1 |
| Dye-21 | 1032.1 |
| Dye-22 | 962.1 |
| Dye-23 | 1172.1 |
| Dye-24 | 1132.2 |

Example 2

Dye-Sensitized Solar Cell

According to the following steps, dye-sensitized solar cells were prepared.

Figure 2:
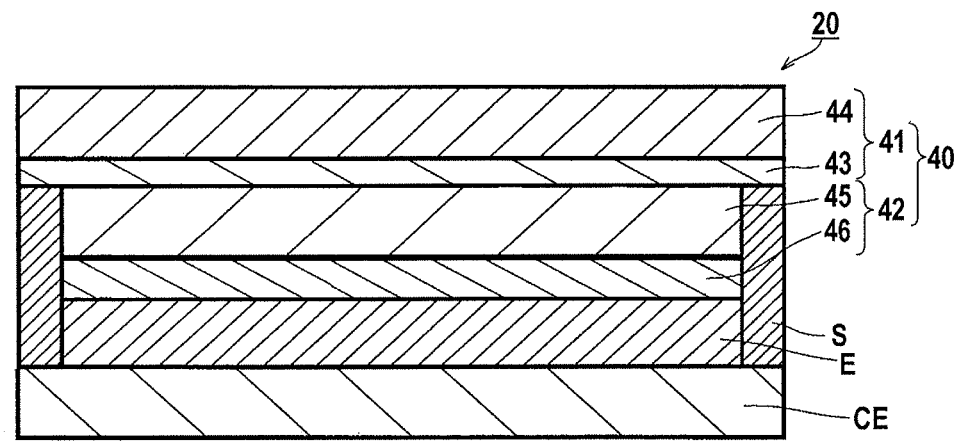
FIG. 2 is a cross-sectional view schematically showing a dye-sensitized solar cell of a second embodiment of the photoelectric conversion element of the present invention.

A photoelectrode having the same configuration as that of the photoelectrode 12 shown in FIG. 5 of JP-A-2002-289274 was produced, and using the photoelectrode, a dye-sensitized solar cell of a scale of 10 mm×10 mm having the same configuration as that of the dye-sensitized solar cell 20 shown in FIG. 3 of JP-A-2002-289274 except for the photoelectrode, was produced. The specific configuration thereof was shown in FIG. 2 attached to the present application. In FIG. 2 of the present application, 41 denotes a transparent electrode, 42 denotes a semiconductor electrode, 43 denotes a transparent electrically-conductive film, 44 denotes a substrate, 45 denotes a semiconductor layer, 46 denotes a light-scattering layer, 40 denotes a photoelectrode, 20 denotes a dye-sensitized solar cell, CE denotes a counter electrode, E denotes an electrolyte, and S denotes a spacer.

(Preparation of Paste)

(Paste A)

Spherical TiO₂ particles (anatase, a mean particle diameter; 25 nm, hereinafter, referred to as spherical TiO₂ particles A) were put into a nitric acid solution, and the resultant mixture was stirred to prepare titania slurry. Next, a cellulose-based binder was added to the titania slurry as a thickening agent, and the resultant mixture was kneaded to prepare a paste.

(Paste 1)

Spherical $TiO_2$ particles A and spherical $TiO_2$ particles (anatase, a mean particle diameter; 200 nm, hereinafter, referred to as spherical $TiO_2$ particles B) were put into a nitric acid solution, and the resultant mixture was stirred to prepare titania slurry. Next, a cellulose-based binder was added to the titania slurry as a thickening agent, and the resultant mixture was kneaded to prepare a paste ((a mass of $TiO_2$ particles A):(a mass of $TiO_2$ particles B)=30:70).

(Paste 2)

Rod-shaped $TiO_2$ particles (anatase, diameter; 100 nm, aspect ratio; 5, hereinafter, referred to as rod-shaped $TiO_2$ particles C) were mixed with the paste A, to prepare a paste having (a mass of rod-shaped $TiO_2$ particles C): (a mass of the paste A)=30:70.

(Production of Photoelectrode)

A transparent electrode was prepared in which a fluorine-doped $SnO_2$ electrically-conductive film (thickness: 500 nm) was formed on a glass substrate. On this $SnO_2$ electrically-conductive film, the paste 1 was applied to by screen printing, followed by drying. Then, the paste was calcined under the conditions of 450° C. in the air. Further, by repeating this screen printing and calcination using the paste 2, the semiconductor electrode having the same configuration as that of the semiconductor electrode 42 shown in FIG. 2 of the present application (the area of the light-receiving face: 10 mm×10 mm; the layer thickness: 16 μm; the layer thickness of the dye-adsorbed layer: 12 μm; the layer thickness of the light-scattering layer: 4 μm; and the content of the rod-shaped $TiO_2$ particles C contained in the light-scattering layer: 30% by mass) were formed on the $SnO_2$ electrically-conductive film. Thus, a photoelectrode, which did not contain a dye, was prepared.

(Absorption of Dye)

Next, a dye was adsorbed to the semiconductor electrode not containing a dye, as follows. First, using anhydrous ethanol dehydrated over magnesium ethoxide as a solvent, each of the metal complex dye described in Table 2 below was dissolved to be $3 \times 10^{-4}$ mol/L. Further, as a co-adsorbent, 20 mol of equimolar mixture of chenodeoxycholic acid and cholic acid was added per 1 mol of metal complex dye, to prepare each dye solution. The measurement of the moisture content in each of the dye solution based on Karl Fisher titration showed that water was less than 0.01% by mass. Next, the semiconductor electrode was immersed into this solution, to complete a photoelectrode 10 in which about $1.5 \times 10^{-7}$ mol/cm² of dye was adsorbed onto the semiconductor electrode.

(Assembly of Dye-Sensitized Solar Cell)

Then, prepared were, as a counter electrode, a platinum electrode (thickness of Pt thin film, 100 nm) having the same shape and size as those of the photoelectrode, and as an electrolyte E, an iodine-based redox solution containing: iodine, lithium iodide, and 4-tert-butylpyridine. Further, a spacer-S (trade name: "Surlyn") manufactured by DuPont, which had a shape matching to the size of the semiconductor electrode, was prepared. As shown in FIG. 3 of JP-A-2002-289274, the photoelectrode 40 and the counter electrode CE were arranged to face each other, with the spacer-S interposed therebetween, followed by filling the electrolyte in the inside thereof. Thus, dye-sensitized solar cells utilizing the photoelectrodes (test Nos. 101 to 118 and c01 to c03) were completed.

The performance evaluation of each dye-sensitized solar cell prepared as above was conducted.

<Spectral Sensitivity Characteristics at Wavelengths 900 nm and 950 nm>

IPCE (quantum yield) in the wavelength of 300 to 1000 nm was measured with an IPCE measuring device manufactured by Peccell Technologies, Inc. Among them, the IPCE in 900 nm and 950 nm were evaluated based on the following criteria.

Evaluation Criteria

A: 1.10 times or more that of Comparative compound (2)
B: 1.01 times or more and less than 1.10 times that of Comparative compound (2)
C: less than 1.01 times that of Comparative compound (2)

<Evaluation of Thermal Deterioration>

The heat resistance test was conducted by introducing each of the dye-sensitized solar cells, into a thermostatic chamber at 40° C. The current was evaluated for the dye-sensitized solar cells before being subjected to the heat resistance test and the dye-sensitized solar cells after being subjected to the heat resistance test for 12 hours. The value obtained by dividing a decrease of the current value after the heat resistance test by the current value before the heat resistance test, was adopted as the thermal deterioration rate. The thermal deterioration rate obtained in this manner was evaluated according to the following criteria in comparison with that of Comparative compound (1).

Evaluation Criteria

A: less than 0.9 times
B: 0.9 times or more and less than 1.0 time
C: 1 time or more It is presented as the thermal deterioration in the following Table 2.

TABLE 2

| Sample No. | Metal complex dye | AL | LD | L | IPCE at 900 nm | IPCE at 950 nm | Thermal deterioration | Remarks |
| --- | --- | --- | --- | --- | --- | --- | --- | --- |
| 101 | Dye-1 | Formula (AL-1) | Formula (DL-1) | Formula (L-1) | A | A | B | This invention |
| 102 | Dye-2 | Formula (AL-1) | Formula (DL-1) | Formula (L-1) | A | A | B | This invention |
| 103 | Dye-3 | Formula (AL-1) | Formula (DL-1) | Formula (L-2) | A | A | B | This invention |
| 104 | Dye-4 | Formula (AL-1) | Formula (DL-1) | Formula (L-2) | A | A | A | This invention |
| 105 | Dye-8 | Formula (AL-1) | Formula (DL-2) | Formula (L-1) | A | A | A | This invention |
| 106 | Dye-9 | Formula (AL-3) | Formula (DL-3) | Formula (L-1) | A | A | A | This invention |
| 107 | Dye-10 | Formula (AL-3) | Formula (DL-1) | Formula (L-1) | A | A | A | This invention |
| 108 | Dye-13 | Formula (AL-1) | Formula (DL-2) | Formula (L-3) | A | A | A | This invention |
| 109 | Dye-14 | Formula (AL-1) | Formula (DL-2) | Formula (L-3) | A | A | A | This invention |
| 110 | Dye-15 | Formula (AL-1) | Formula (DL-2) | Formula (L-3) | A | A | A | This invention |
| 111 | Dye-16 | Formula (AL-3) | Formula (DL-2) | Formula (L-3) | A | A | A | This invention |
| 112 | Dye-17 | Formula (AL-1) | Formula (DL-2) | Formula (L-3) | A | A | A | This invention |
| 113 | Dye-18 | Formula (AL-1) | Formula (DL-2) | Formula (L-3) | A | A | A | This invention |
| 114 | Dye-19 | Formula (AL-1) | Formula (DL-2) | Formula (L-3) | A | A | A | This invention |
| 115 | Dye-20 | Formula (AL-1) | Formula (DL-2) | Formula (L-3) | A | A | A | This invention |
| 116 | Dye-21 | Formula (AL) | Formula (DL-2) | Formula (L-3) | A | A | A | This invention |

TABLE 2-continued

| Sample No. | Metal complex dye | AL | LD | L | IPCE at 900 nm | IPCE at 950 nm | Thermal deterioration | Remarks |
|---|---|---|---|---|---|---|---|---|
| 117 | Dye-22 | Formula (AL) | Formula (DL-2) | Formula (L-3) | A | A | A | This invention |
| 118 | Dye-23 | Formula (AL-2) | Formula (DL-2) | Formula (L-3) | A | A | A | This invention |
| 119 | Dye-24 | Formula (AL-4) | Formula (DL-2) | Formula (L-3) | A | A | A | This invention |
| c01 | Comparative compound (1) | Formula (AL-1) | — | Formula (L-3) | C | C | C (Standard) | Comparative Example |
| c02 | Comparative compound (2) | Formula (AL-1) | — | Formula (L-3) | C (Standard) | C (Standard) | C | Comparative Example |
| c03 | Comparative compound (3) | — | — | Formula (L-1) | C | C | C | Comparative Example |

Comparative compound (1)

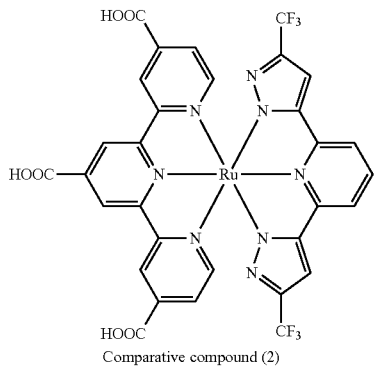

Comparative compound (2)

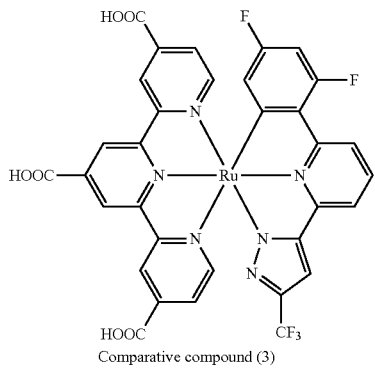

Comparative compound (3)

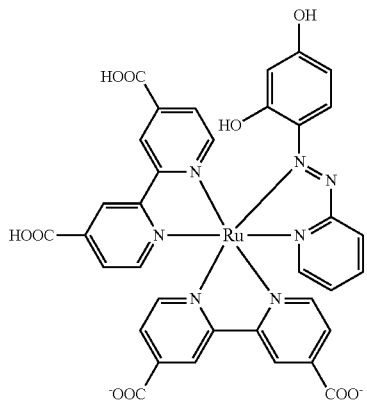

The above comparative compounds (1) to (3) are metal complex dyes as described below.

Comparative compound (1): Compound TF-1 described in US patent application publication No. 2012/0073660 specification Comparative compound (2): Compound TF-6 described in the above specification Comparative compound (3): Compound 31 described in International publication No. WO 91/16719 pamphlet As shown in the above Table 2, it can be confirmed that as compared with the comparative compounds, the sensitivity characteristics at 900 nn and at the long wavelength range of 950 nm, and durability are excellent.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Electrically-conductive support
2 Photoconductor layer
21 Dye
22 Semiconductor fine-particle
3 Charge-transfer layer
4 Counter electrode
5 Light-receiving electrode
6 Circuit
10 Photoelectric conversion element
100 System using dye-sensitized solar cell
M Electric motor (electric fan)
20 Dye-sensitized solar cell
40 Photoelectrode
41 Transparent electrode
42 Semiconductor electrode
43 Transparent electrically-conductive film
44 Substrate
45 Semiconductor layer
46 Light-scattering layer
CE Counter electrode
E Electrolyte
S Spacer

The invention claimed is:

1. A photoelectric conversion element, having an electrically conductive support, a photoconductor layer containing an electrolyte, a charge transfer layer containing an electrolyte, and a counter electrode, wherein the photoconductor layer contains semiconductor fine particles carrying a metal complex dye represented by the following Formula (I):

$$M(LD)(LA)\cdot(CI) \quad \text{Formula (I)}$$

wherein, in the formula, M represents a metal ion;
LD represents a tridentate ligand represented by any one of the following formulas (DL-1) to (DL-4);
LA represents a tridentate ligand represented by the following formula (AL); and
CI represents a counter ion necessary to neutralize an electric charge:

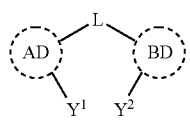

Formula (DL-1)

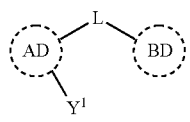

Formula (DL-2)

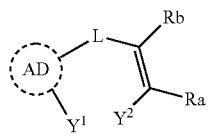

Formula (DL-3)

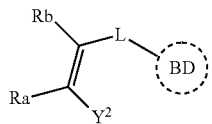

Formula (DL-4)

wherein, in the formulas, $Y^1$ and $Y^2$ each independently represent an oxygen atom, a sulfur atom, a substituted or unsubstituted nitrogen atom, or a substituted or unsubstituted phosphorus atom, each of which coordinates with the metal ion M; the ring AD and the ring BD each independently represents a hydrocarbon ring or a hetero ring; L represents a linking group represented by any one of the following formulas (L-1) to (L-4); and Ra and Rb each independently represent a substituent,

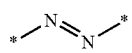

Formula (L-1)

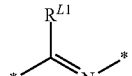

Formula (L-2)

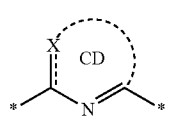

Formula (L-3)

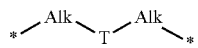

Formula (L-4)

wherein, in the formulas, $R^{L1}$ represents a hydrogen atom or a substituent; X represents a nitrogen atom or a carbon atom; the ring CD represents a nitrogen-containing hetero ring containing X; the bond between X and the carbon atom bonded with X and N may be a single bond or a double bond; the ring CD may have a substituent; T represents —O—, —S—, —NR$^{L2}$— or —PR$^{L3}$—; R$^{L2}$ and R$^{L3}$ each independently represent a hydrogen atom or a substituent; and Alk represents an alkylene group, which may have a substituent,

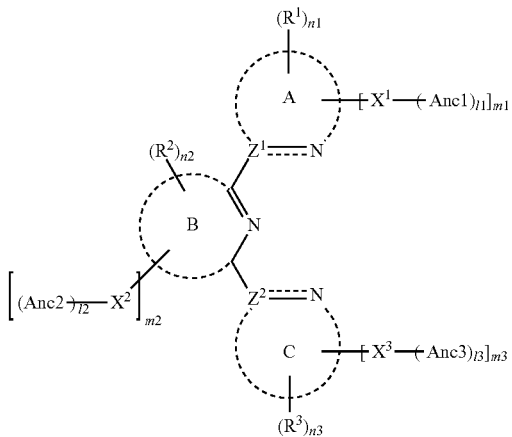

Formula (AL)

wherein, in the formulas, the ring A, the ring B, and the ring C each independently represent a nitrogen-containing aromatic hetero ring; wherein, the bond between $Z^1$ and N and the bond between $Z^2$ and N may be a single bond or a double bond; $Z^1$ and $Z^2$ each independently represent a carbon atom or a nitrogen atom;

Anc1 to Anc3 each independently represent —$CO_2H$, —$SO_3H$, —$PO_3H_2$, —OH, —SH or a salt thereof; $X^1$, $X^2$ and $X^3$ each independently represent a single bond or a linking group; l1 to l3 each independently represent an integer of 1 to 5; m1 and m3 each independently represent an integer of 0 to 4; m2 represent an integer of 0 to 3; a total of m1 to m3 is 1 or more;

$R^1$ to $R^3$ each independently represent a substituent other than Anc1 to Anc3; n1 and n3 each independently represent an integer of 0 to 2; and n2 represents 0 or 1.

2. The photoelectric conversion element according to claim 1, wherein M represents $Fe^{2+}$, $Ru^{2+}$ or $Os^{2+}$.

3. The photoelectric conversion element according to claim 1, wherein LD represents a tridentate ligand represented by formula (DL-1) or formula (DL-2); and L in formula (DL-1) or formula (DL-2) is a linking group represented by formula (L-1) or formula (L-3).

4. The photoelectric conversion element according to claim 1, wherein the ring CD in formula (L-3) is a pyridine ring, a pyrimidine ring, or a triazine ring.

5. The photoelectric conversion element according to claim 1, wherein the ring AD and the ring BD in formulas (DL-1) to (DL-4) is a benzene ring, a pyrazole ring, or a triazole ring.

6. The photoelectric conversion element according to claim 1, wherein L represents a linking group represented by formula (L-1) or a linking group represented by formula (L-3); and when L is a linking group represented by formula (L-1),
in formula (DL-1), the ring AD and the ring BD each independently represent a benzene ring, a pyrazole ring, or an imidazole ring; $Y^1$ and $Y^2$ each independently represent —$O^-$, —$S^-$, or —$NR^-$, herein R represents a hydrogen atom or a substituent;
in formula (DL-2), the ring AD represents a benzene ring, and the ring BD represents a benzene ring, a pyrazole ring, an imidazole ring, or a triazole ring; $Y^1$ represents —$O^-$, —$S^-$, or —$NR^-$, herein R represents a hydrogen atom or a substituent;
in formula (DL-3), the ring AD represents a benzene ring; and $Y^1$ and $Y^2$ each independently represent —$O^-$, —$S^-$, or —$NR^-$, herein R represents a hydrogen atom or a substituent; and when L is a linking group represented by formula (L-3),
in formula (DL-1), the ring AD and the ring BD each represent a benzene ring; $Y^1$ and $Y^2$ each independently represent —$O^-$, —$S^-$, or —$NR^-$, herein R represents a hydrogen atom or a substituent;
in formula (DL-2), the ring AD represents a benzene ring, the ring BD represents a benzene ring, a pyrazole ring, an imidazole ring, or a triazole ring; and $Y^1$ represents —$O^-$, —$S^-$, or —$NR^-$, herein R represents a hydrogen atom or a substituent.

7. The photoelectric conversion element according to claim 1, wherein the ring A, the ring B, and the ring C in the formula (AL) each represent a pyridine ring, a pyrimidine ring, or a thiazole ring.

8. The photoelectric conversion element according to claim 1, wherein the formula (AL) is the following formula (AL-1) or formula (AL-2):

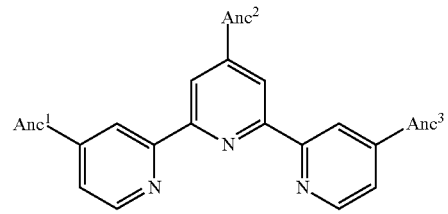

Formula (AL-1)

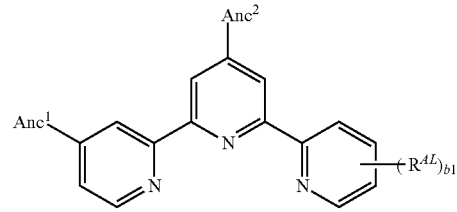

Formula (AL-2)

wherein, in the formulas, $Anc^1$ to $Anc^3$ each independently represent —$CO_2H$, —$SO_3H$, —$PO_3H_2$ or a salt thereof; $R^{AL}$ represents a substituent other than $Anc^1$ to $Anc^3$; and b1 represents an integer of 0 to 4.

9. The photoelectric conversion element according to claim 8, wherein the formula (AL) is the formula (AL-1).

10. The photoelectric conversion element according to claim 8, wherein the formula (AL) is the formula (AL-2).

11. The photoelectric conversion element according to claim 1, wherein the formula (AL) is the following formula (AL-3) or formula (AL-4):

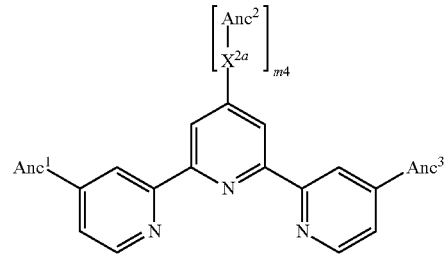

Formula (AL-3)

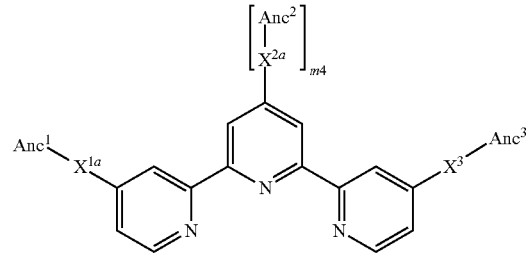

Formula (AL-4)

wherein, in the formulas, $Anc^1$ to $Anc^3$ each independently represent —$CO_2H$, —$SO_3H$, —$PO_3H_2$ or a salt thereof; $X^{2a}$ represents —O—, —S—, —NR'—, a divalent saturated aliphatic group, a divalent aromatic hydrocarbon ring group, a divalent non-aromatic hydrocarbon ring group, a divalent aromatic hetero ring group, a divalent non-aromatic hetero ring group, or a linking group formed by any combination of these;

wherein R' represents a hydrogen atom or a substituent; $X^{1a}$ represents a linking group; $X^3$ represents a single bond or a linking group; and m4 represents 0 or 1.

12. The photoelectric conversion element according to claim 1, wherein a co-adsorbent having one or more acidic groups is carried on the semiconductor fine-particles.

13. The photoelectric conversion element according to claim 12, wherein the co-adsorbent is represented by the following formula (CA):

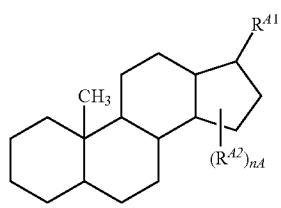

Formula (CA)

wherein, in the formula, $R^{A1}$ represents a substituent having an acidic group; $R^{A2}$ represents a substituent; and nA represents an integer of 0 or more.

14. A dye-sensitized solar cell, containing the photoelectric conversion element according to claim 1.

15. A metal complex dye, which is represented by the following formula (I):

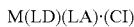

Formula (I)

wherein, in the formula, M represents a metal ion;
LD represents a tridentate ligand represented by any one of the following formulas (DL-1) to (DL-4);
LA represents a tridentate ligand represented by the following formula (AL); and
CI represents a counter ion necessary to neutralize an electric charge:

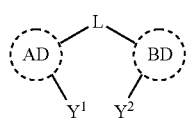

Formula (DL-1)

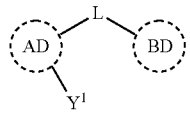

Formula (DL-2)

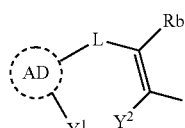

Formula (DL-3)

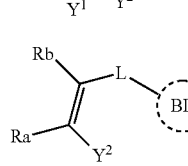

Formula (DL-4)

wherein, in the formulas, $Y^1$ and $Y^2$ each independently represent an oxygen atom, a sulfur atom, a substituted or unsubstituted nitrogen atom, or a substituted or unsubstituted phosphorus atom, each of which coordinates with a metal ion M; the ring AD and the ring BD each independently represents a hydrocarbon ring or a hetero ring; L represents a linking group represented by any one of the following formulas (L-1) to (L-4); and Ra and Rb each independently represent a substituent,

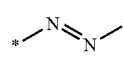

Formula (L-1)

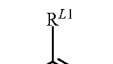

Formula (L-2)

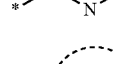

Formula (L-3)

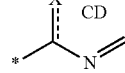

Formula (L-4)

wherein, in the formulas, $R^{L1}$ represents a hydrogen atom or a substituent; X represents a nitrogen atom or a carbon atom; the ring CD represents a nitrogen-containing hetero ring containing X; the bond between X and the carbon atom bonded with X and N may be a single bond or a double bond; the ring CD may have a substituent; T represents —O—, —S—, —$NR^{L2}$— or —$PR^{L3}$—; $R^{L2}$ and $R^{L3}$ each independently represent a hydrogen atom or a substituent; and Alk represents an alkylene group, which may have a substituent,

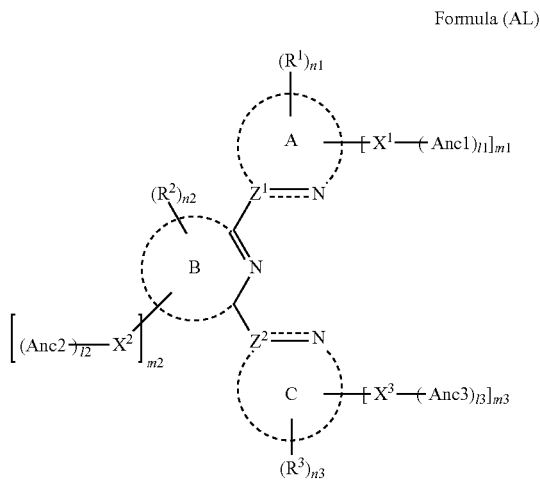

Formula (AL)

wherein, in the formula, the ring A, the ring B, and the ring C each independently represent a nitrogen-containing aromatic hetero ring; wherein, the bond between $Z^1$ and N and the bond between $Z^2$ and N may be a single bond or a double bond; $Z^1$ and $Z^2$ each independently represent a carbon atom or a nitrogen atom;
Anc1 to Anc3 each independently represent —$CO_2H$, —$SO_3H$, —$PO_3H_2$, —OH, —SH or a salt thereof; $X^1$, $X^2$ and $X^3$ each independently represent a single bond or a linking group; l1 to l3 each independently represent an integer of 1 to 5; m1 and m3 each independently represent an integer of 0 to 4; m2 represent an integer of 0 to 3; a total of m1 to m3 is 1 or more;
$R^1$ to $R^3$ each independently represent a substituent other than Anc1 to Anc3;

n1 and n3 each independently represent an integer of 0 to 2; and n2 represents 0 or 1.

16. The metal complex dye according to claim 15, wherein L represents a linking group represented by formula (L-1) or a linking group represented by formula (L-3); and when L is formula (L-1),
- in formula (DL-1), the ring AD and the ring BD each independently represent a benzene ring, a pyrazole ring, or an imidazole ring; $Y^1$ and $Y^2$ each independently represent —O$^-$, —S$^-$, or —NR$^-$, herein R represents a hydrogen atom or a substituent;
- in formula (DL-2), the ring AD represents a benzene ring, and the ring BD represents a benzene ring, a pyrazole ring, an imidazole ring, or a triazole ring; $Y^1$ represents —O$^-$, —S$^-$, or —NR$^-$, herein R represents a hydrogen atom or a substituent;
- in formula (DL-3), the ring AD represents a benzene ring; and $Y^1$ and $Y^2$ each independently represent —O$^-$, —S$^-$, or —NR$^-$, herein R represents a hydrogen atom or a substituent; and when L is formula (L-3),
- in formula (DL-1), the ring AD and the ring BD each represent a benzene ring; $Y^1$ and $Y^2$ each independently represent —O$^-$, —S$^-$, or —NR$^-$, herein R represents a hydrogen atom or a substituent;
- in formula (DL-2), the ring AD represents a benzene ring, and the ring BD represents a benzene ring, a pyrazole ring, an imidazole ring, or a triazole ring; and $Y^1$ represents —O$^-$, —S$^-$, or —NR$^-$, herein R represents a hydrogen atom or a substituent.

17. The metal complex dye according to claim 15, wherein the formula (AL) is any one of the following formulas (AL-1) to (AL-4):

Formula (AL-1)

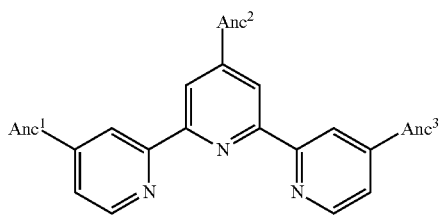

Formula (AL-2)

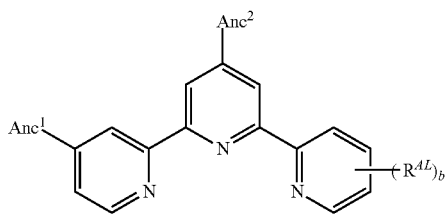

Formula (AL-3)

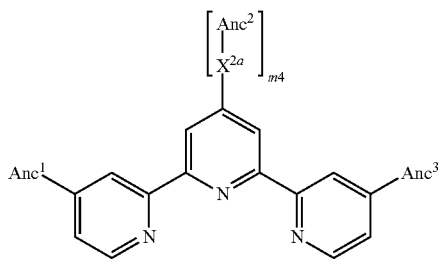

-continued

Formula (AL-4)

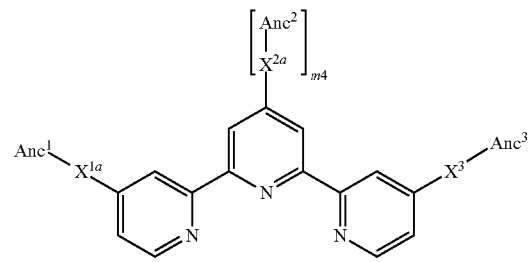

wherein, in the formulas, Anc$^1$ to Anc$^3$ each independently represent —CO$_2$H, —SO$_3$H, —PO$_3$H$_2$ or a salt thereof; R$^{AL}$ represents a substituent other than Anc$^1$ to Anc$^3$; b1 represents an integer of 0 to 4; X$^{2a}$ represents —O—, —S—, —NR'—, a divalent saturated aliphatic group, a divalent aromatic hydrocarbon ring group, a divalent non-aromatic hydrocarbon ring group, a divalent aromatic hetero ring group, a divalent non-aromatic hetero ring group, or a linking group formed by any combination of these; herein R' represents a hydrogen atom or a substituent; X$^{1a}$ represents a linking group; X$^3$ represents a single bond or a linking group; and m4 represents 0 or 1.

18. A dye solution, dissolved therein the metal complex dye according to claim 15.

19. The dye solution according to claim 18, wherein, in an organic solvent, the metal complex dye is contained in an amount of from 0.001 to 0.1% by mass, and water is limited to 0.1% by mass or less.

20. The dye solution according to claim 18, further containing a co-adsorbent.

21. The dye solution according to claim 20, wherein the co-adsorbent is represented by the following formula (CA):

Formula (CA)

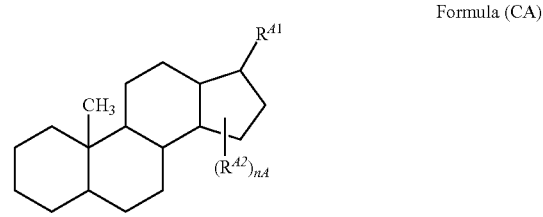

wherein, in the formula, R$^{A1}$ represents a substituent having an acidic group; R$^{A2}$ represents a substituent; and nA represents an integer of 0 or more.

22. A dye-adsorbed electrode for a dye-sensitized solar cell, having a photoconductor layer which is formed by applying a composition obtained from the dye solution according to claim 18 on an electrically-conductive support provided with a semiconductor, and then, curing the composition after being applied.

23. A method of producing a dye-sensitized solar cell, the method including assembling the dye-adsorbed electrode according to claim 22 and materials to be an electrolyte and a counter electrode.

* * * * *